United States Patent
Lee et al.

(10) Patent No.: US 11,974,498 B2
(45) Date of Patent: Apr. 30, 2024

(54) ORGANIC COMPOUND FOR ORGANIC LIGHT EMITTING DIODE AND AN ORGANIC LIGHT EMITTING DIODE INCLUDING THE SAME WITH HIGH EFFICIENCY

(71) Applicant: SFC CO., LTD., Cheongju-si (KR)

(72) Inventors: Seung-Soo Lee, Cheongju-si (KR); Tae Gyun Lee, Cheongju-si (KR); Sang-woo Park, Cheongju-si (KR)

(73) Assignee: SFC CO., LTD., Seoul (KR)

( * ) Notice: Subject to any disclaimer, the term of this patent is extended or adjusted under 35 U.S.C. 154(b) by 532 days.

(21) Appl. No.: 17/130,757

(22) Filed: Dec. 22, 2020

(65) Prior Publication Data

US 2021/0202862 A1  Jul. 1, 2021

(30) Foreign Application Priority Data

Dec. 23, 2019 (KR) .................. 10-2019-0173333
Dec. 16, 2020 (KR) .................. 10-2020-0176488

(51) Int. Cl.

| | |
|---|---|
| *C07D 307/93* | (2006.01) |
| *C09K 11/06* | (2006.01) |
| *H10K 85/60* | (2023.01) |
| *H10K 50/11* | (2023.01) |
| *H10K 50/15* | (2023.01) |
| *H10K 50/16* | (2023.01) |

(Continued)

(52) U.S. Cl.
CPC ......... *H10K 85/636* (2023.02); *C07D 307/93* (2013.01); *C09K 11/06* (2013.01); *H10K 85/633* (2023.02); *C09K 2211/1018* (2013.01); *H10K 50/11* (2023.02); *H10K 50/156* (2023.02); *H10K 50/16* (2023.02); *H10K 50/17* (2023.02); *H10K 50/171* (2023.02); *H10K 85/615* (2023.02); *H10K 85/626* (2023.02); *H10K 85/6574* (2023.02); *H10K 2101/10* (2023.02)

(58) Field of Classification Search
None
See application file for complete search history.

(56) References Cited

U.S. PATENT DOCUMENTS

| | | | |
|---|---|---|---|
| 10,950,814 B2* | 3/2021 | Park ................ | H10K 50/171 |
| 2017/0012214 A1* | 1/2017 | Pyo ................. | H10K 85/636 |

(Continued)

FOREIGN PATENT DOCUMENTS

| | | |
|---|---|---|
| KR | 101074193 B1 | 10/2011 |
| KR | 101455156 B1 | 10/2014 |

(Continued)

OTHER PUBLICATIONS

Machine translation of KR_20190134364-A, translation generated Jun. 2023, 15 pages. (Year: 2023).*

*Primary Examiner* — Robert S Loewe
(74) *Attorney, Agent, or Firm* — STIP Law Group, LLC

(57) ABSTRACT

Disclosed are a compound for an organic light-emitting device, and an organic light-emitting diode comprising the same and exhibiting high efficiency. More particularly, the compound has a specific structure represented by Chemical Formula A or B and is used as a material for a hole injection layer or a hole transport layer in an organic light-emitting diode to confer high efficiency on the organic light-emitting diode. Chemical Formulas A and B are as defined in the description.

13 Claims, 1 Drawing Sheet

(51) Int. Cl.
*H10K 50/17* (2023.01)
*H10K 101/10* (2023.01)

(56) References Cited

U.S. PATENT DOCUMENTS

2017/0331053 A1* 11/2017 Voges .................... H10K 85/30
2018/0093962 A1* 4/2018 Choi ...................... H10K 50/15

FOREIGN PATENT DOCUMENTS

| KR | 20180060619 A | | 6/2018 | |
|----|---------------|---|---------|---------|
| KR | 20190134364 A | * | 12/2019 | ............. C09K 11/06 |
| KR | 20200089891 A | | 7/2020 | |

\* cited by examiner

| 80 |
| 70 |
| 60 |
| 50 |
| 40 |
| 30 |
| 20 |
| 10 |

ORGANIC COMPOUND FOR ORGANIC LIGHT EMITTING DIODE AND AN ORGANIC LIGHT EMITTING DIODE INCLUDING THE SAME WITH HIGH EFFICIENCY

CROSS-REFERENCE TO RELATED APPLICATIONS

This application claims the priority of the Korean Patent Applications NO 10-2019-0173333 filed on Dec. 23, 2019 and NO 10-2020-0176488 filed on Dec. 16, 2020, in the Korean Intellectual Property Office, the disclosure of which is incorporated herein by reference.

BACKGROUND OF THE INVENTION

1. Field of the Invention

The present disclosure pertains to a compound for an organic light-emitting device, and an organic light-emitting diode comprising the same and exhibiting high efficiency. More particularly, the present disclosure pertains to a compound which has a specific structure and is used as a material for a hole injection layer or a hole transport layer in an organic light-emitting diode to confer high efficiency thereon, and an organic light-emitting diode comprising the same.

2. Description of the Prior Art

Organic light-emitting diodes (OLEDs), based on self-luminescence, are used to create digital displays with the advantage of having a wide viewing angle and being able to be made thinner and lighter than liquid crystal displays. In addition, an OLED display exhibits a very fast response time. Accordingly, OLEDs find applications in the full color display field or the illumination field.

In general, the term "organic light-emitting phenomenon" refers to a phenomenon in which electrical energy is converted to light energy by means of an organic material. An organic light-emitting diode using the organic light-emitting phenomenon has a structure usually including an anode, a cathode, and an organic material layer interposed therebetween.

In this regard, the organic material layer may have, for the most part, a multilayer structure consisting of different materials, for example, a hole injection layer, a hole transport layer, a light-emitting layer, an electron transport layer, and an electron injection layer in order to enhance the efficiency and stability of the organic light-emitting diode. In the organic light-emitting diode having such a structure, application of a voltage between the two electrodes injects a hole from the anode and an electron from the cathode to the organic layer. In the luminescent zone, the hole and the electron recombine to produce an exciton. When the exciton returns to the ground state from the excited state, the molecule of the organic layer emits light. Such an organic light-emitting diode is known to have characteristics such as self-luminescence, high luminance, high efficiency, low driving voltage, a wide viewing angle, high contrast, and high-speed response.

Materials used as organic layers in OLEDs may be divided into luminescent materials and charge transport materials, for example, a hole injection material, a hole transport material, an electron injection material, and an electron transport material and, as needed, further into an electron-blocking material or a hole-blocking material.

With regard to related arts pertaining to hole transport layers, reference may be made to Korean Patent No. 10-1074193 (issued Oct. 14, 2011), which describes an organic light-emitting diode using a carbazole structure fused with at least one benzene ring in a hole transport layer, and Korean Patent No. 10-1455156 (issued Oct. 27, 2014), which describes an organic light-emitting diode in which the HOMO energy level of an auxiliary light-emitting layer is set between those of a hole transport layer and a light-emitting layer.

In spite of enormous effort for fabricating organic light-emitting diodes, however, there is still continued need to develop novel organic light-emitting diodes having more effective properties, compared to those developed based on conventional technology.

PRIOR ART DOCUMENT

Korean Patent No. 10-1074193 (issued Oct. 14, 2011)
Korean Patent No. 10-1455156 (issued Oct. 27, 2014)

SUMMARY OF THE INVENTION

Therefore, the purpose of the present disclosure is to provide a compound having a novel structure for use in an organic light-emitting diode, and an organic light-emitting diode with high efficiency, in which the compound is employed as a material for a hole injection layer or a hole transport layer.

The present disclosure provides a compound, represented by the following Chemical Formula A or B, for use in an organic light-emitting diode:

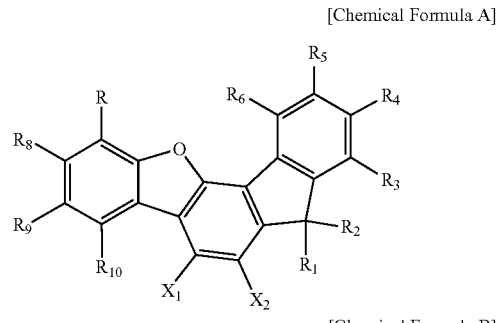

[Chemical Formula A]

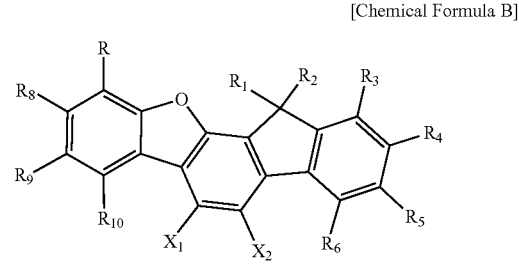

[Chemical Formula B]

wherein, $X_1$ and $X_2$, which may be the same or different, are each independently any one selected from a hydrogen atom, a deuterium atom, a substituted or unsubstituted alkyl of 1 to 30 carbon atoms, a substituted or unsubstituted cycloalkyl of 3 to 30 carbon atoms, a substituted or unsubstituted aryl of 6 to 50 carbon atoms, a substituted or unsubstituted heteroaryl of 2 to 50 carbon atoms, a substituted or unsubstituted heterocycloalkyl of 1 to 30 carbon atoms, a substituted or unsubstituted alkylsilyl of 1 to 30 carbon atoms, a substituted or unsubstituted arylsilyl of 6 to 30 carbon atoms, a cyano, a nitro, and a halogen, wherein at least one of $X_1$ and $X_2$ is any one selected from among a substituted or unsubstituted alkyl of 1 to 30 carbon atoms, a substituted or unsubstituted aryl of 6 to 50 carbon atoms, a substituted or unsubstituted heteroaryl of 2 to 50 carbon atoms, a substituted or unsubstituted cycloalkyl of 3 to 30 carbon atoms, a substituted or unsubstituted heterocycloaryl of 1 to 30 carbon atoms, a substituted or unsubstituted alkylsilyl of 1 to 30 carbon atoms, and a substituted or unsubstituted arylsilyl of 6 to 30 carbon atoms; and $R_1$ to $R_{10}$, which may be the same or different, are each independently any one selected from among a hydrogen atom, a deuterium atom, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted heterocycloaryl of 1 to carbon atoms, a substituted or unsubstituted alkoxy of 1 to 30 carbon atoms, a substituted or unsubstituted aryloxy of 6 to 30 carbon atoms, a substituted or unsubstituted alkyl thioxy of 1 to 30 carbon atoms, a substituted or unsubstituted aryl thioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted aryl of 6 to 50 carbon atoms, a substituted or unsubstituted heteroaryl of 2 to 50 carbon atoms, a substituted or unsubstituted alkylsilyl of 1 to 30 carbon atoms, a substituted or unsubstituted arylsilyl of 6 to 30 carbon atoms, a cyano, a nitro, and a halogen, wherein one or two of $R_3$ to $R_{10}$ are substituents represented by the following Structural Formula A, under which when two of $R_3$ to $R_{10}$ are substituents represented by Structural Formula A, the two substituents may be the same or different:

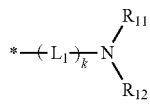

[Structural Formula A]

wherein, the linker $L_1$ is any one selected from among a single bond, a substituted or unsubstituted arylene of 6 to 30 carbon atoms, and a substituted or unsubstituted heteroarylene of 1 to 30 carbon atoms, k is an integer of 1 to 3, under which when k is 2 or greater, the corresponding $L_1$'s may be the same or different, $R_{11}$ and $R_{12}$, which may be the same or different, are each independently any one selected from a substituted or unsubstituted aryl of 6 to 50 carbon atoms, a substituted or unsubstituted cycloalkyl of 3 to 30 carbon atoms, a substituted or unsubstituted heterocycloaryl of 1 to 30 carbon atoms, a substituted or unsubstituted heteroaryl of 2 to 50 carbon atoms, "*" denotes a bonding site between any one of $R_3$ to $R_{10}$ and a carbon atom of the benzene rings in the scaffold;

$R_1$ and $R_2$ may be connected to each other to form a mono- or polycyclic aliphatic or aromatic ring which may bear at least one heteroatom selected from among N, O, P, Si, S, Ge, Se, and Te as a ring member;

wherein the term "substituted" in the expression "substituted or unsubstituted" used for [Chemical Formula A] and [Chemical Formula B] means having at least one substituent selected from the group consisting of a deuterium atom, a cyano, a halogen, a hydroxy, a nitro, an alkyl of 1 to 24 carbon atoms, a halogenated alkyl of 1 to 24 carbon atoms, an alkenyl of 1 to 24 carbon atoms, an alkynyl of 1 to 24 carbon atoms, a heteroalkyl of 1 to 24 carbon atoms, an aryl of 6 to 24 carbon atoms, an arylalkyl of 6 to 24 carbon atoms, a heteroaryl of 2 to 24 carbon atoms, a heteroarylalkyl of 2 to 24 carbon atoms, an alkoxy of 1 to 24 carbon atoms, an alkylamino of 1 to 24 carbon atoms, an arylamino of 1 to 24 carbon atoms, a heteroarylamino of 1 to 24 carbon atoms, an alkylsilyl of 1 to 24 carbon atoms, an arylsilyl of 1 to 24 carbon atoms, and an aryloxy of 1 to 24 carbon atoms.

BRIEF DESCRIPTION OF THE DRAWINGS

The above and other aspects, features and advantages of the present disclosure will be more apparent from the following detailed description taken in conjunction with the accompanying drawings, in which:

FIG. 1 is a schematic view of an organic light-emitting diode according to an embodiment of the present disclosure.

DETAILED DESCRIPTION OF THE EXEMPLARY EMBODIMENTS

Hereinafter, exemplary embodiments which can be easily implemented by those skilled in the art will be described with reference to the accompanying drawings. In each drawing of the present disclosure, sizes or scales of components may be enlarged or reduced than their actual sizes or scales for better illustration, and known components are not depicted therein to clearly show features of the present disclosure. Therefore, the present disclosure is not limited to the drawings. When describing the principle of the embodiments of the present disclosure in detail, details of well-known functions and features may be omitted to avoid unnecessarily obscuring the presented embodiments.

In drawings, for convenience of description, sizes of components may be exaggerated for clarity. For example, since sizes and thicknesses of components in drawings are arbitrarily shown for convenience of description, the sizes and thicknesses are not limited thereto. Furthermore, throughout the description, the terms "on" and "over" are used to refer to the relative positioning, and mean not only that one component or layer is directly disposed on another component or layer but also that one component or layer is indirectly disposed on another component or layer with a further component or layer being interposed therebetween. Also, spatially relative terms, such as "below", "beneath", "lower", and "between", may be used herein for ease of description to refer to the relative positioning.

Throughout the specification, unless explicitly described to the contrary, the word "comprise" and variations such as "comprises" or "comprising" will be understood to imply the inclusion of stated elements but not the exclusion of any other elements. Also, throughout the specification, the term "on" means to be located above or below the object portion, and does not necessarily mean that the object is located on the upper side with respect to the gravitational direction.

The present disclosure provides a compound for an organic light-emitting diode, represented by the following Chemical Formula A or B:

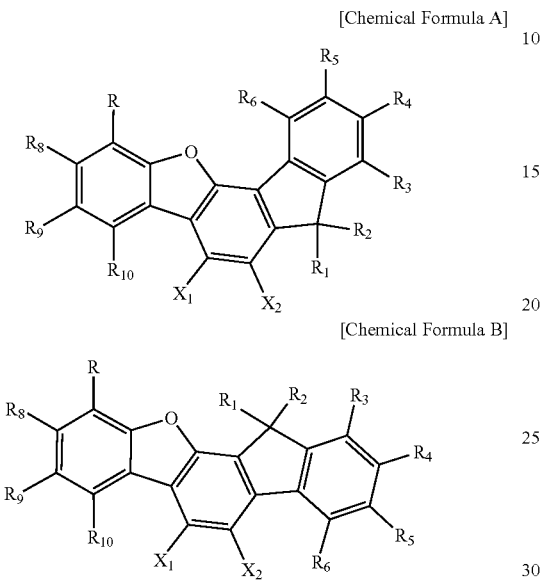

[Chemical Formula A]

[Chemical Formula B]

wherein, $X_1$ and $X_2$, which may be the same or different, are each independently any one selected from a hydrogen atom, a deuterium atom, a substituted or unsubstituted alkyl of 1 to 30 carbon atoms, a substituted or unsubstituted cycloalkyl of 3 to 30 carbon atoms, a substituted or unsubstituted aryl of 6 to 50 carbon atoms, a substituted or unsubstituted heteroaryl of 2 to 50 carbon atoms, a substituted or unsubstituted heterocycloalkyl of 1 to 30 carbon atoms, a substituted or unsubstituted alkylsilyl of 1 to 30 carbon atoms, a substituted or unsubstituted arylsilyl of 6 to 30 carbon atoms, a cyano, a nitro, and a halogen, wherein at least one of $X_1$ and $X_2$ is any one selected from among a substituted or unsubstituted alkyl of 1 to 30 carbon atoms, a substituted or unsubstituted aryl of 6 to 50 carbon atoms, a substituted or unsubstituted heteroaryl of 2 to 50 carbon atoms, a substituted or unsubstituted cycloalkyl of 3 to 30 carbon atoms, a substituted or unsubstituted heterocycloaryl of 1 to 30 carbon atoms, a substituted or unsubstituted alkylsilyl of 1 to 30 carbon atoms, and a substituted or unsubstituted arylsilyl of 6 to 30 carbon atoms; and $R_1$ to $R_{10}$, which may be the same or different, are each independently any one selected from among a hydrogen atom, a deuterium atom, a substituted or unsubstituted alkyl of 1 to 30 carbon atoms, a substituted or unsubstituted alkenyl of 2 to 30 carbon atoms, a substituted or unsubstituted alkynyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted heterocycloaryl of 1 carbon atoms, a substituted or unsubstituted alkoxy of 1 to 30 carbon atoms, a substituted or unsubstituted aryloxy of 6 to 30 carbon atoms, a substituted or unsubstituted alkyl thioxy of 1 to 30 carbon atoms, a substituted or unsubstituted aryl thioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted aryl of 6 to 50 carbon atoms, a substituted or unsubstituted heteroaryl of 2 to 50 carbon atoms, a substituted or unsubstituted alkylsilyl of 1 to 30 carbon atoms, a substituted or unsubstituted arylsilyl of 6 to 30 carbon atoms, a cyano, a nitro, and a halogen, wherein one or two of $R_3$ to $R_{10}$ are substituents represented by the following Structural Formula A, under which when two of $R_3$ to $R_{10}$ are substituents represented by Structural Formula A, the two substituents may be the same or different:

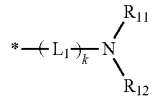

[Structural Formula A]

wherein, the linker $L_1$ is any one selected from among a single bond, a substituted or unsubstituted arylene of 6 to 30 carbon atoms, and a substituted or unsubstituted heteroarylene of 1 to 30 carbon atoms, k is an integer of 1 to 3, under which when k is 2 or greater, the corresponding $L_1$'s may be the same or different, $R_{11}$ and $R_{12}$, which may be the same or different, are each independently any one selected from a substituted or unsubstituted aryl of 6 to 50 carbon atoms, a substituted or unsubstituted cycloalkyl of 3 to 30 carbon atoms, a substituted or unsubstituted heterocycloaryl of 1 to 30 carbon atoms, a substituted or unsubstituted heteroaryl of 2 to 50 carbon atoms, "*" denotes a bonding site between any one of $R_3$ to $R_{10}$ and a carbon atom of the benzene rings in the scaffold;

$R_1$ and $R_2$ may be connected to each other to form a mono- or polycyclic aliphatic or aromatic ring which may bear at least one heteroatom selected from among N, O, P, Si, S, Ge, Se, and Te as a ring member;

wherein the term "substituted" in the expression "substituted or unsubstituted" used for [Chemical Formula A] and [Chemical Formula B] means having at least one substituent selected from the group consisting of a deuterium atom, a cyano, a halogen, a hydroxy, a nitro, an alkyl of 1 to 24 carbon atoms, a halogenated alkyl of 1 to 24 carbon atoms, an alkenyl of 1 to 24 carbon atoms, an alkynyl of 1 to 24 carbon atoms, a heteroalkyl of 1 to 24 carbon atoms, an aryl of 6 to 24 carbon atoms, an arylalkyl of 6 to 24 carbon atoms, a heteroaryl of 2 to 24 carbon atoms, a heteroarylalkyl of 2 to 24 carbon atoms, an alkoxy of 1 to 24 carbon atoms, an alkylamino of 1 to 24 carbon atoms, an arylamino of 1 to 24 carbon atoms, a heteroarylamino of 1 to 24 carbon atoms, an alkylsilyl of 1 to 24 carbon atoms, an arylsilyl of 1 to 24 carbon atoms, and an aryloxy of 1 to 24 carbon atoms.

The expression indicating the number of carbon atoms, such as "a substituted or unsubstituted alkyl of 1 to 30 carbon atoms", "a substituted or unsubstituted aryl of 5 to 50 carbon atoms", etc. means the total number of carbon atoms of, for example, the alkyl or aryl radical or moiety alone, exclusive of the number of carbon atoms of substituents attached thereto. For instance, a phenyl group with a butyl at the para position falls within the scope of an aryl of 6 carbon atoms, even though it is substituted with a butyl radical of 4 carbon atoms.

As used herein, the term "aryl" means an organic radical derived from an aromatic hydrocarbon by removing one hydrogen that is bonded to the aromatic hydrocarbon. It may be a single or fused aromatic system. Further, the aromatic system may include a fused ring that is formed by adjacent substituents on the aryl radical.

Examples of the aryl include phenyl, o-biphenyl, m-biphenyl, p-biphenyl, o-terphenyl, m-terphenyl, p-terphenyl, naphthyl, anthryl, phenanthryl, pyrenyl, indenyl, fluorenyl, tetrahydronaphthyl, perylenyl, chrysenyl, naphthacenyl, and fluoranthenyl, but are not limited thereto. At least one hydrogen atom of the aryl may be substituted by a deuterium atom, a halogen atom, a hydroxy, a nitro, a cyano, a silyl, an amino (—NH$_2$, —NH(R), —N(R') (R'') wherein R' and R'' are each independently an alkyl of 1 to 10 carbon atoms, in this case, called "alkylamino"), an amidino, a hydrazine, a hydrazone, a carboxyl, a sulfonic acid, a phosphoric acid, an alkyl of 1 to 24 carbon atoms, a halogenated alkyl of 1 to 24 carbon atoms, an alkenyl of 1 to 24 carbon atoms, an alkynyl of 1 to 24 carbon atoms, a heteroalkyl of 1 to 24 carbon atoms, an aryl of 6 to 24 carbon atoms, an arylalkyl of 6 to 24 carbon atoms, a heteroaryl of 2 to 24 carbon atoms, or a heteroarylalkyl of 2 to 24 carbon atoms.

The heteroaryl substituent used in the compound of the present disclosure refers to a hetero aromatic radical of 2 to 50 carbon atoms, preferably 2 to 24 carbon atoms, bearing 1, 2, or 3 heteroatoms selected from among N, O, P, Se, Te, Si, Ge, and S. In the aromatic radical, two or more rings may be fused. One or more hydrogen atoms on the heteroaryl may be substituted by the same substituents as on the aryl.

As used herein, the term "heteroaromatic ring" refers to an aromatic hydrocarbon ring bearing at least one heteroatom as a ring member. Preferably, a heteroaromatic ring may bear as ring members one to three identical or different heteroatoms selected from among N, O, P, Si, S, Ge, Se, and Te.

Examples of the alkyl substituent useful in the present disclosure include methyl, ethyl, propyl, isopropyl, isobutyl, sec-butyl, tert-butyl, pentyl, iso-amyl, and hexyl. At least one hydrogen atom of the alkyl may be substituted by the same substituent as in the aryl.

Representative among examples of the cycloalkyl substituent useful in the present disclosure are cyclopropyl, cyclobutyl, cyclopentyl, cyclohexyl, adamantyl, and the like. At least one hydrogen atom of the cycloalkyl may be substituted by the same substituents as in the aryl.

Examples of the alkoxy substituent useful in the present disclosure include methoxy, ethoxy, propoxy, isobutyloxy, sec-butyloxy, pentyloxy, iso-amyloxy, hexyloxy, and the like. At least one hydrogen atom of the alkoxy may be substituted by the same substituent as in the aryl.

Examples of the silyl useful in the present disclosure include trimethylsilyl, triethylsilyl, triphenylsilyl, trimethoxysilyl, dimethoxyphenylsilyl, diphenylmethylsilyl, diphenylvinylsilyl, methylcyclobutylsilyl, dimethylfurylsilyl, and the like. One or more hydrogen atoms of the silyl may be substituted by the same substituent as in the aryl.

The compound, represented by Chemical Formula A or B, for an organic light-emitting diode according to the present disclosure is technically characterized by an indenodibenzofuran structure based on the polycyclic fused ring "'6-membered ring'-'5-membered ring bearing an oxygen atom'-'6-membered ring'-'5-membered ring bearing a carbon atom having $R_1$ and $R_2$ bonded thereto'-'6-membered ring'", in which the carbon atom having both $R_1$ and $R_2$ bonded thereto and one carbon member of the benzene ring having substituents $R_3$ to $R_6$ are respectively bonded to two carbon members of the benzene ring, one carbon member being bonded to the carbon atom adjacent to the oxygen atom and another carbon member being adjacent to the one carbon member in the dibenzofuran moiety, wherein an amine group represented by Structural Formula A

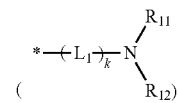

is bonded to one or two carbon members on the outer 6-membered rings of the indenodibenzofuran ring structure; and at least one of two carbon atoms in the central 6-membered aromatic ring moiety of the indenodibenzofuran structure has a substituent bonded thereto, the substituent being selected from among a substituted or unsubstituted alkyl of 1 to 30 carbon atoms, a substituted or unsubstituted aryl of 6 to 50 carbon atoms, a substituted or unsubstituted heteroaryl of 2 to 50 carbon atoms, a substituted or unsubstituted cycloalkyl of 3 to 30 carbon atoms, a substituted or unsubstituted heterocycloaryl of 1 to 30 carbon atoms, a substituted or unsubstituted alkylsilyl of 1 to 30 carbon atoms, and a substituted or unsubstituted arylsilyl of 6 to 30 carbon atoms. In the scaffold of the indenodibenzofuran ring having the amine group bonded thereto, the intramolecular electron distribution shifts from localization to delocalization due to the substituent, such as an aryl, a heteroaryl, etc., added to the central 6-membered aromatic hydrocarbon ring in the scaffold. Characterized by the structure, the compound is inferred to become stable and have a prolonged lifetime, and as such, can make a contribution to the development of an organic light-emitting diode exhibiting high efficiency and long lifetime characteristics.

In an embodiment, the substituents $R_1$ and $R_2$ in Chemical Formulas A and B, which may be the same or different, are each independently any one selected from among an alkyl of 1 to 6 carbon atoms and an aryl of 6 to 18 carbon atoms. Preferably, the substituents $R_1$ and $R_2$, which may be the same or different, are each independently any one selected from among methyl and phenyl.

In an embodiment, one of the substituents $X_1$ and $X_2$ may be selected from among a substituted or unsubstituted alkyl of 1 to 30 carbon atoms, a substituted or unsubstituted aryl of 6 to 50 carbon atoms, a substituted or unsubstituted heteroaryl of 2 to 50 carbon atoms, and a substituted or unsubstituted cycloalkyl of 3 to 30 carbon atoms while the other may be a hydrogen atom or a deuterium atom.

In an alternative embodiment, at least one of the substituents $X_1$ and $X_2$ may be a substituted or unsubstituted alkyl of 1 to 12 carbon atoms, a substituted or unsubstituted cycloalkyl of 3 to 18 carbon atoms, a substituted or unsubstituted aryl of 6 to 18 carbon atoms, or a substituted or unsubstituted heteroaryl of 2 to 20 carbon atoms. Preferably, one of the substituents $X_1$ and $X_2$ may be a substituted or unsubstituted aryl of 6 to 18 carbon atoms or a substituted or unsubstituted heteroaryl of 3 to 20 carbon atoms while the other may be a hydrogen atom or a deuterium atom.

In an embodiment of the present disclosure, only one of the substituents $R_3$ to $R_{10}$ in Chemical Formulas A and B may be a substituent represented by Structural Formula A. In this context, $R_7$ may be the substituent represented by the following Structural Formula A:

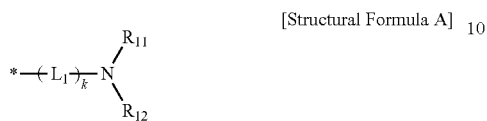

[Structural Formula A]

wherein, $R_{11}$ and $R_{12}$, which may be the same or different, are each independently any one selected from among a substituted or unsubstituted aryl of 6 to 18 carbon atoms, and a substituted or unsubstituted heteroaryl of 2 to 20 carbon atoms, and $L_1$ and k are as defined above.

Concrete examples of the compound represented by Chemical Formula A or Chemical Formula B include the following [Compound 1] to [Compound 54]:

[Compound 1]

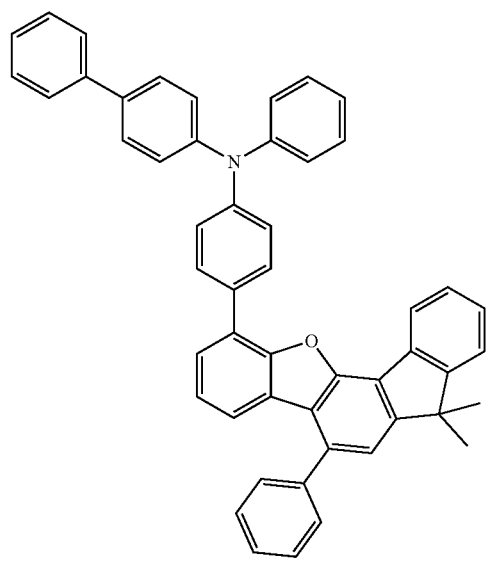

[Compound 2]

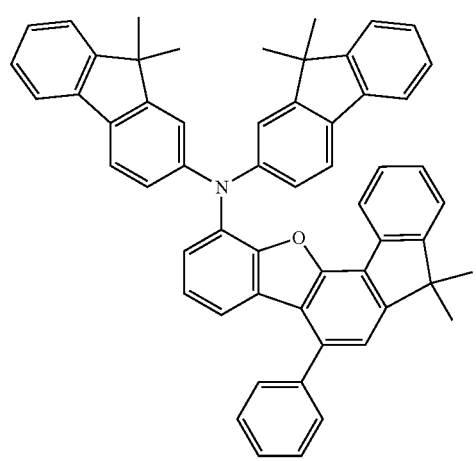

[Compound 3]

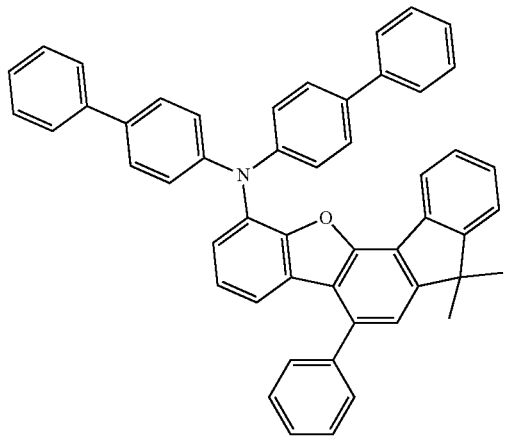

[Compound 4]

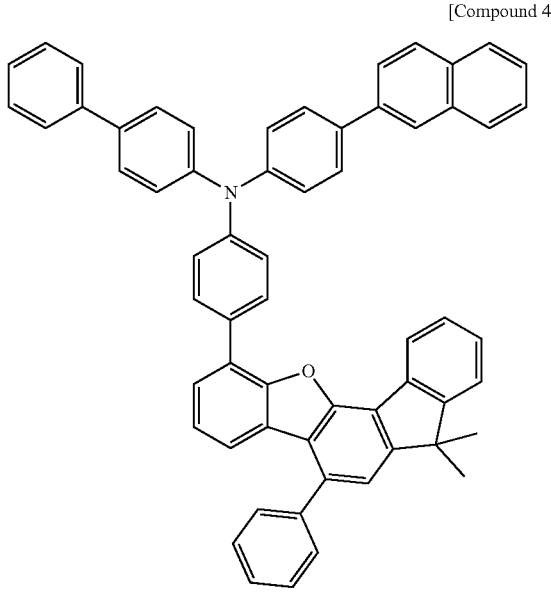

[Compound 5]

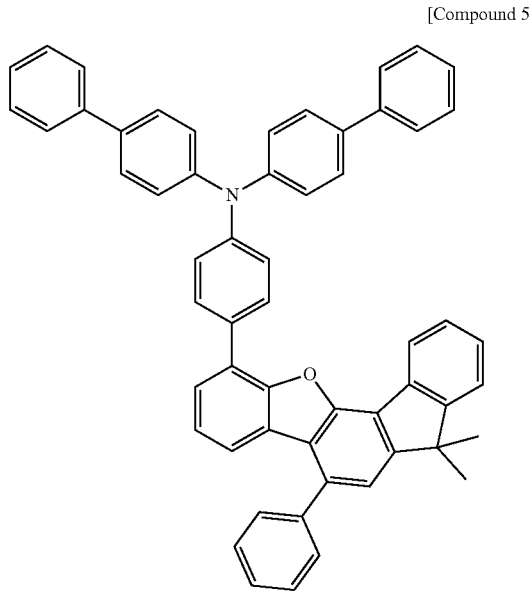

[Compound 6]
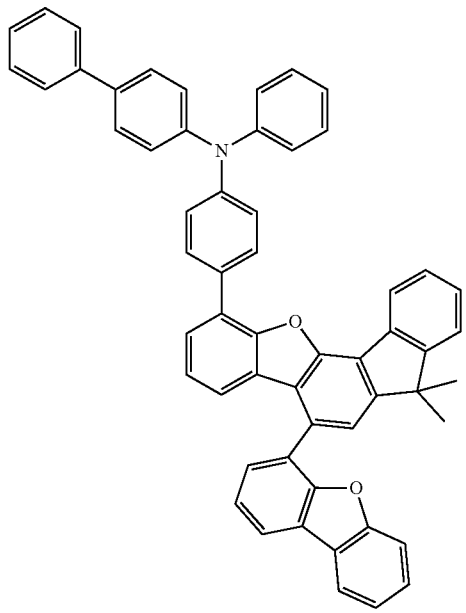
[Compound 8]
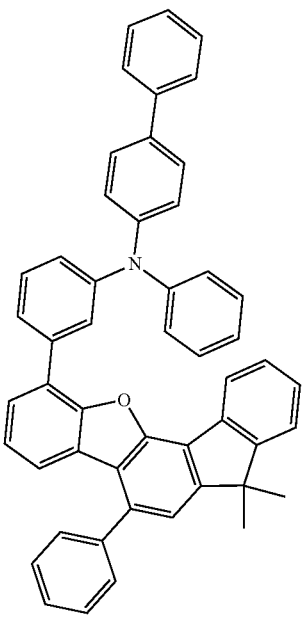
[Compound 7]
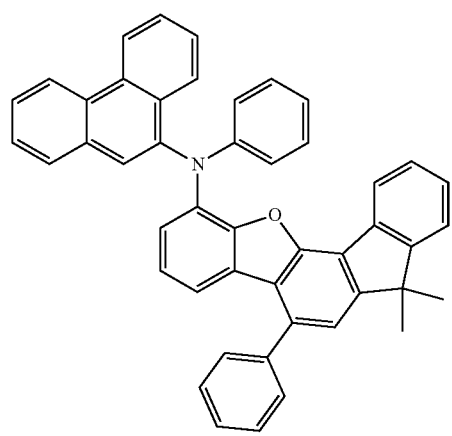
[Compound 9]
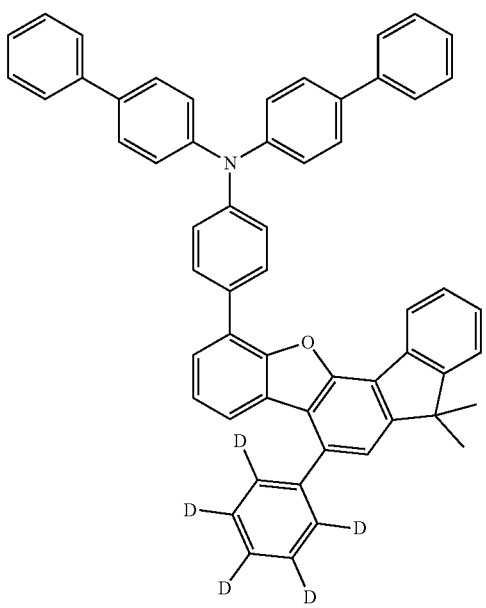

[Compound 10]
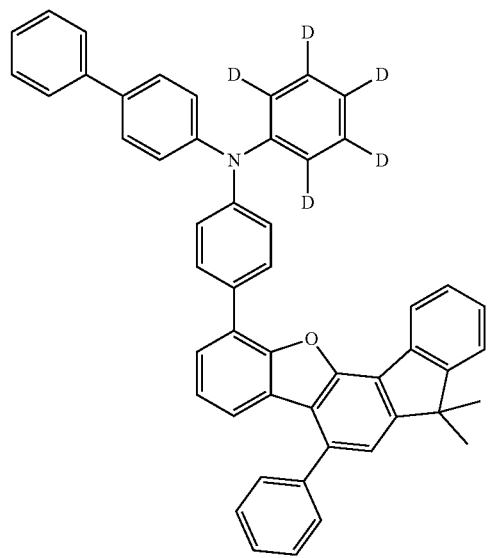
[Compound 11]
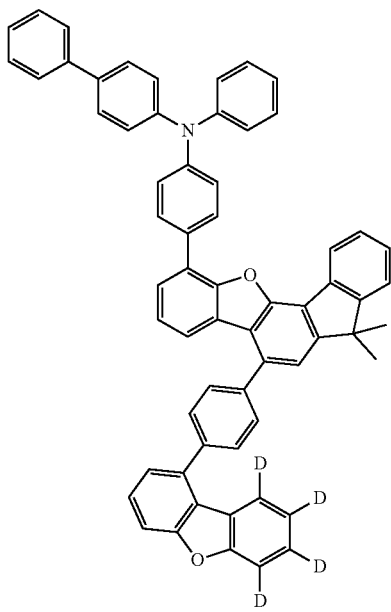
[Compound 12]
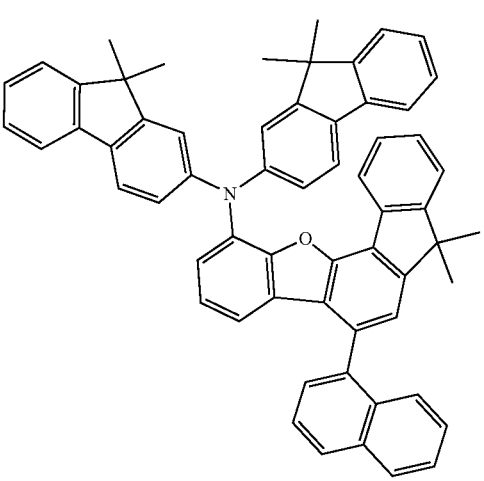
[Compound 13]

[Compound 14]
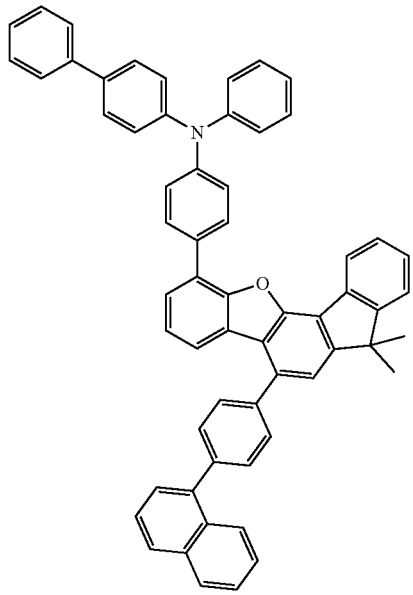
[Compound 15]
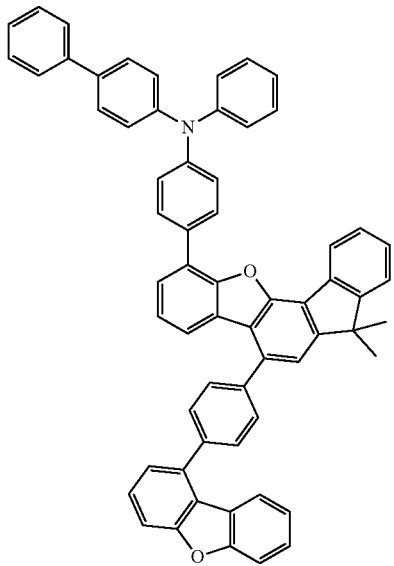
[Compound 16]
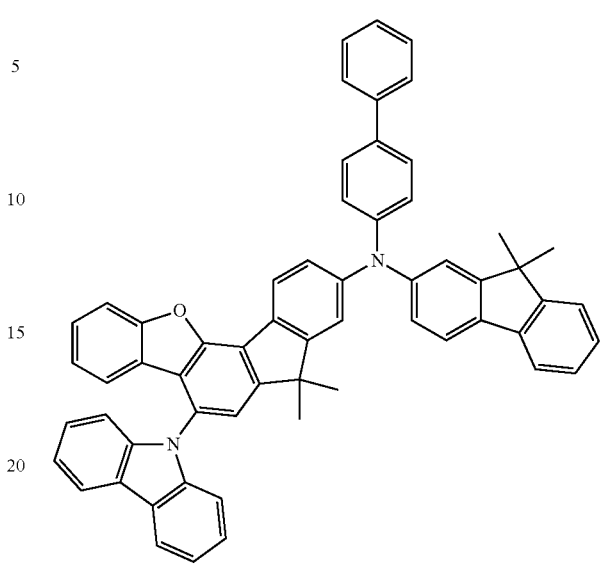
[Compound 17]
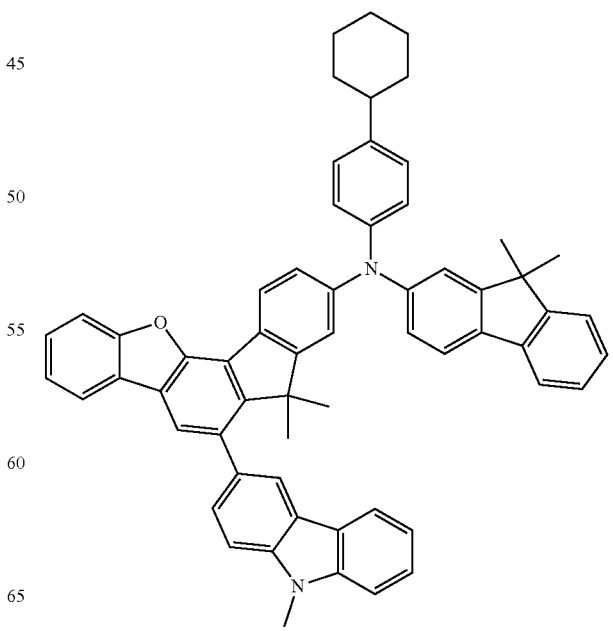

[Compound 18]
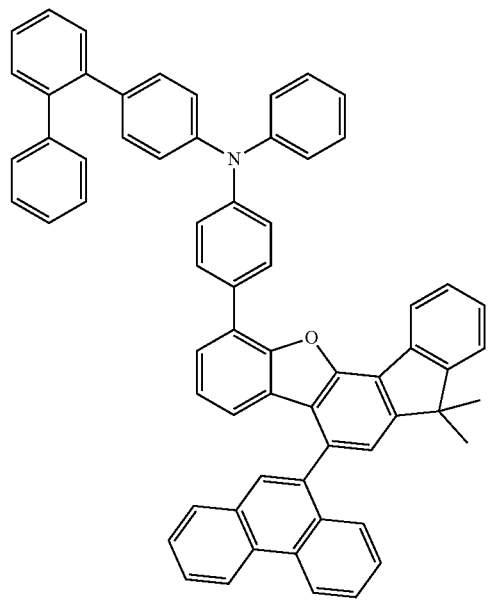
[Compound 19]
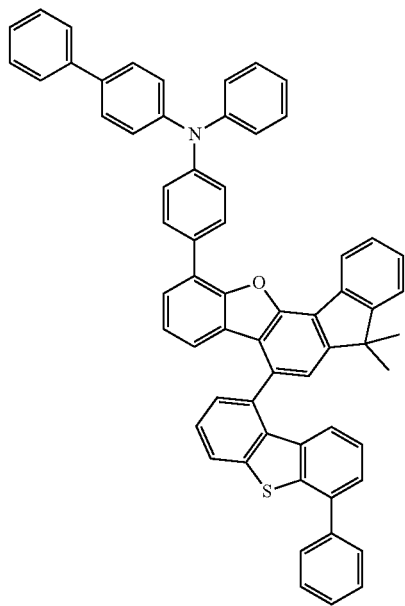
[Compound 20]
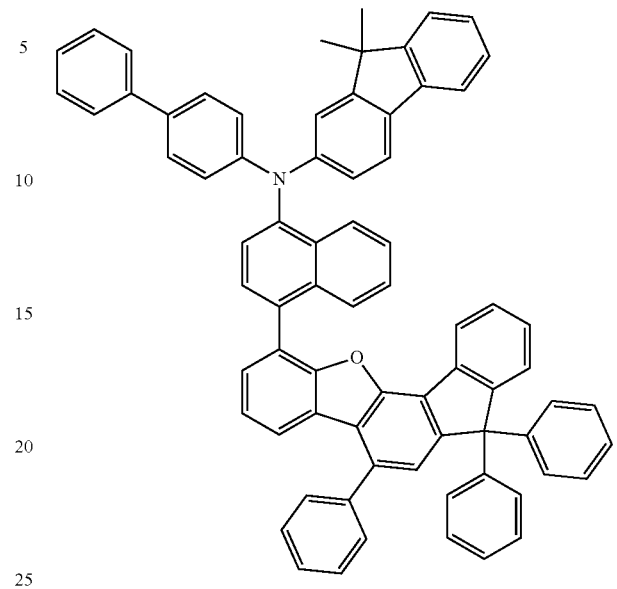
[Compound 21]
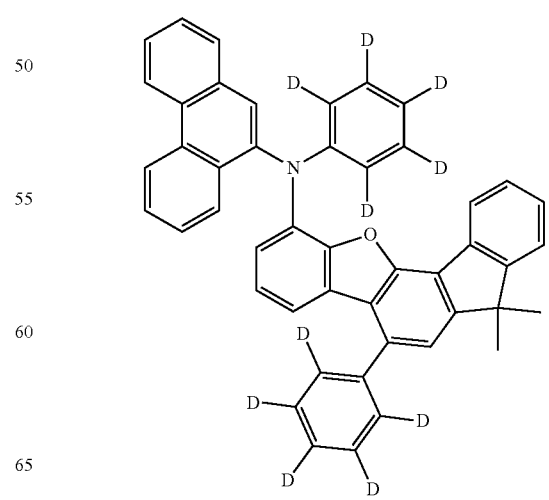

[Compound 22]
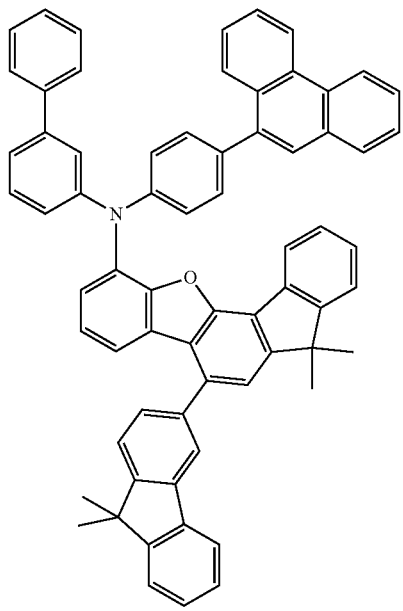
[Compound 23]
[Compound 24]
[Compound 25]
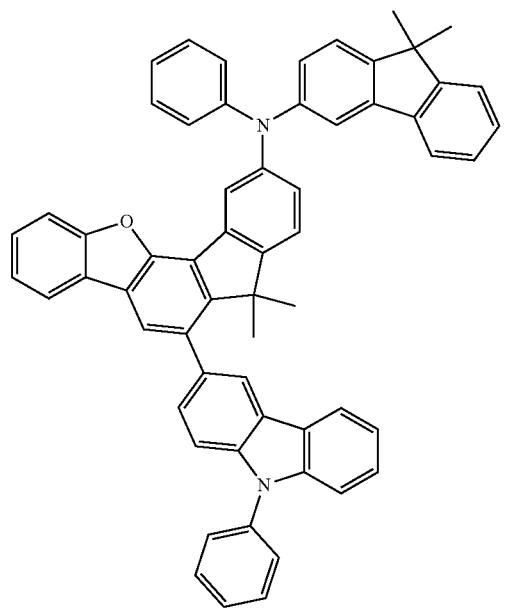
[Compound 26]
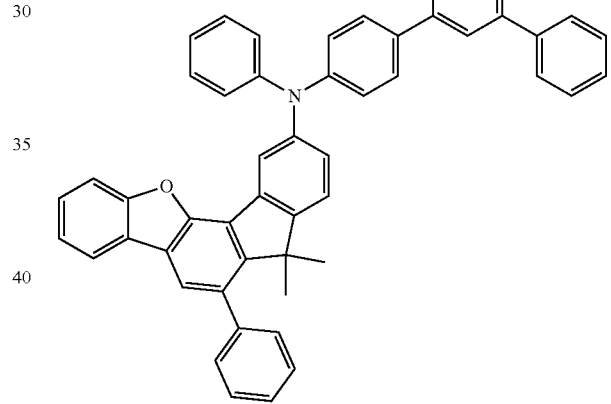
[Compound 27]
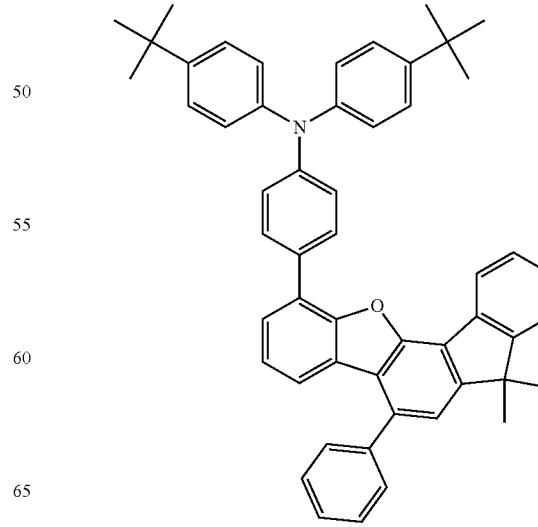

[Compound 28]
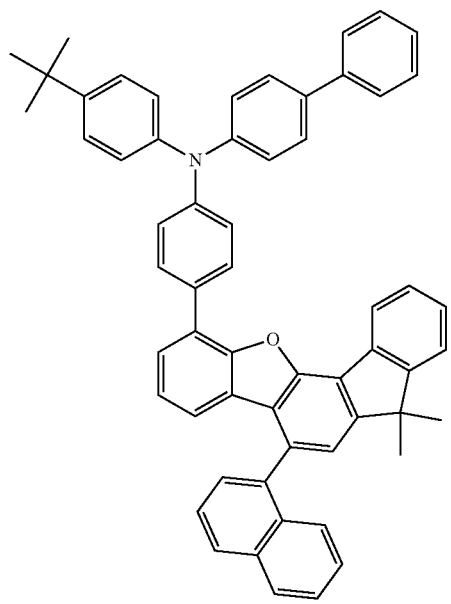
[Compound 30]
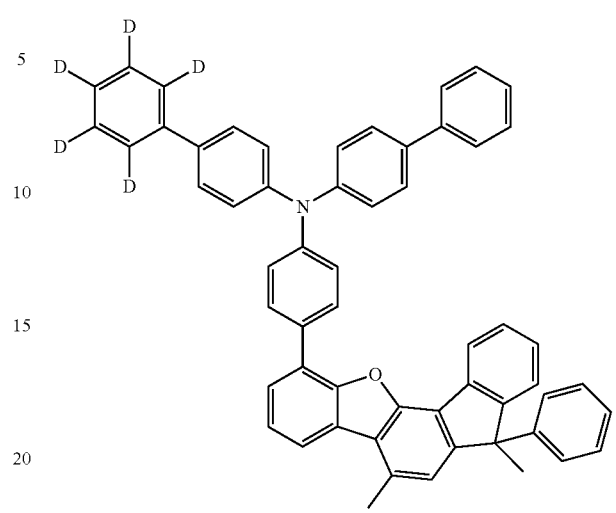
[Compound 31]
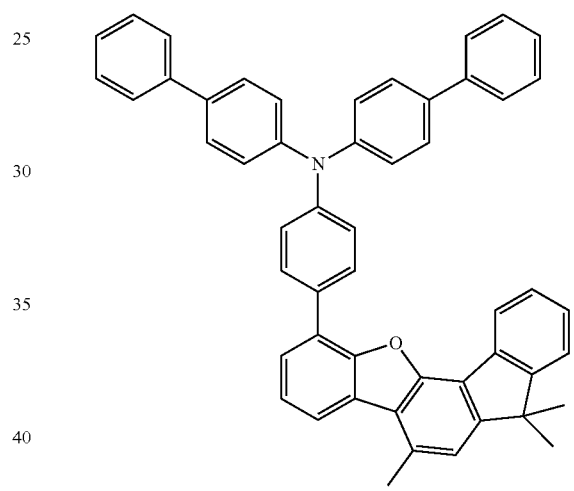
[Compound 29]
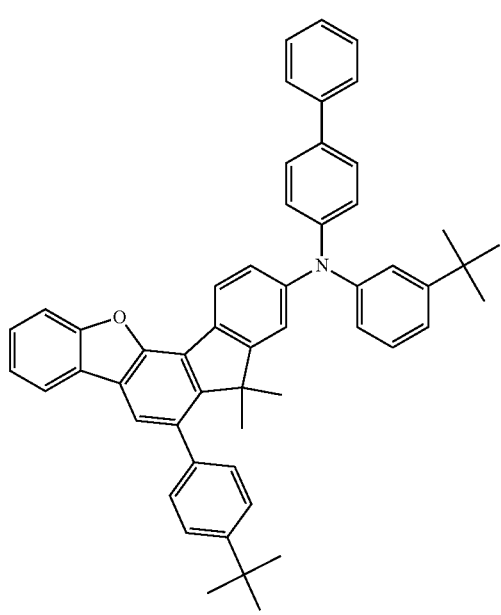
[Compound 32]
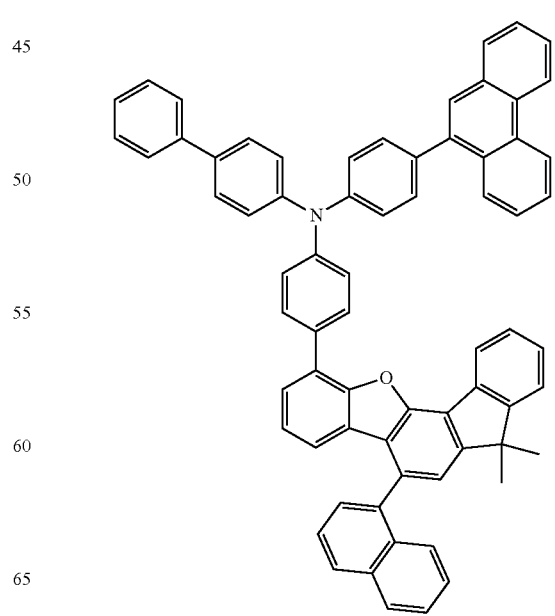

[Compound 33]
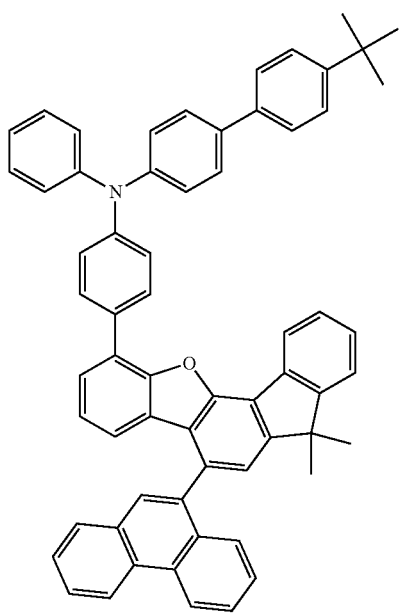
[Compound 34]
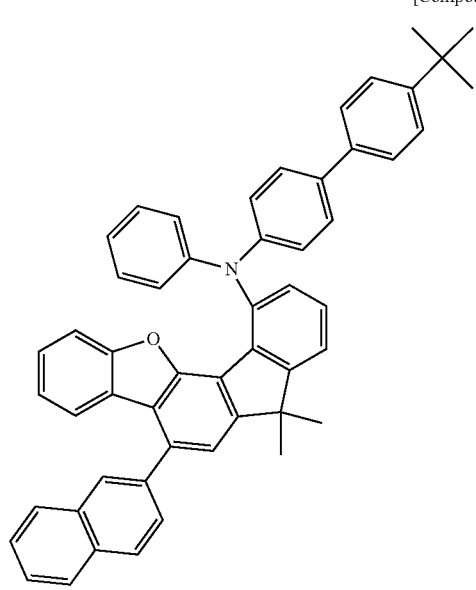
[Compound 35]
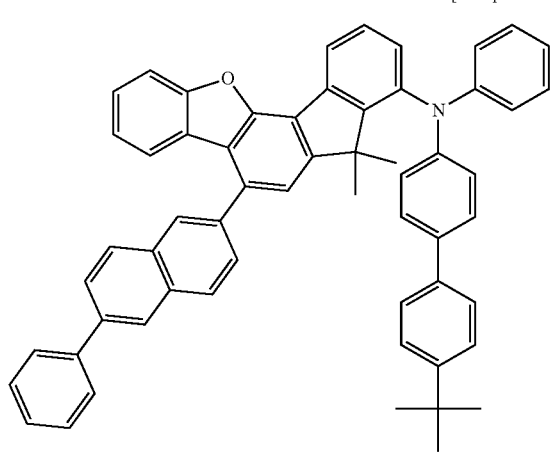
[Compound 36]
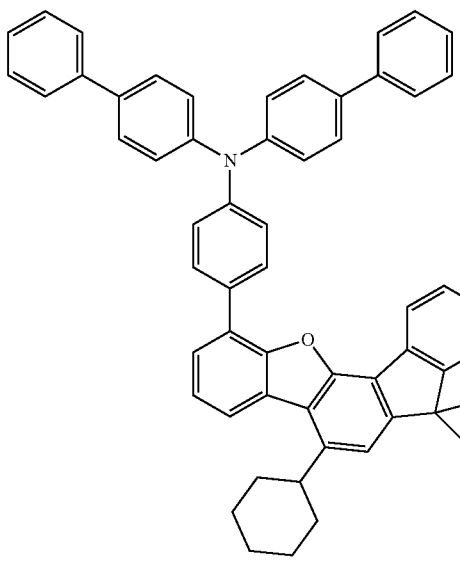
[Compound 37]
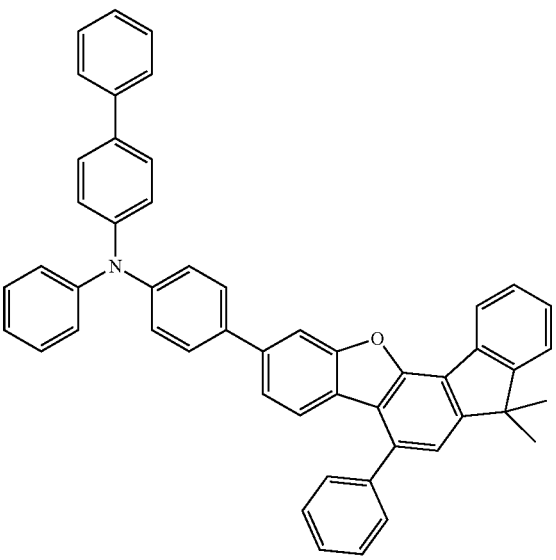
[Compound 38]
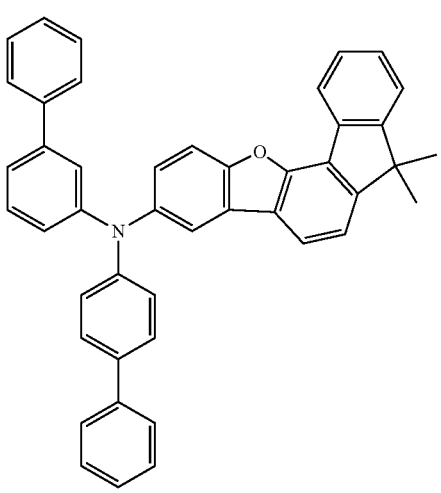

[Compound 39]
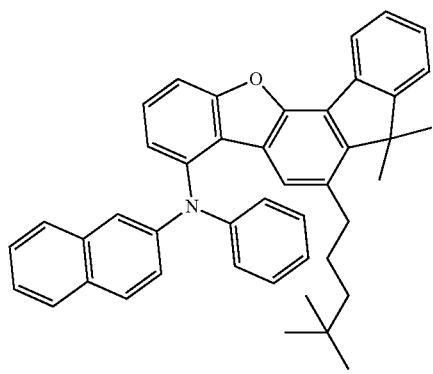
[Compound 42]
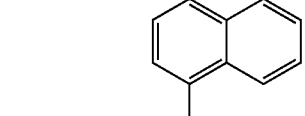
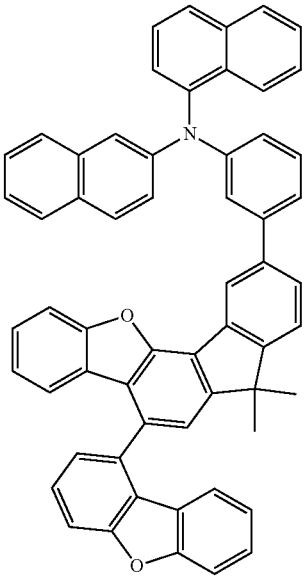
[Compound 40]
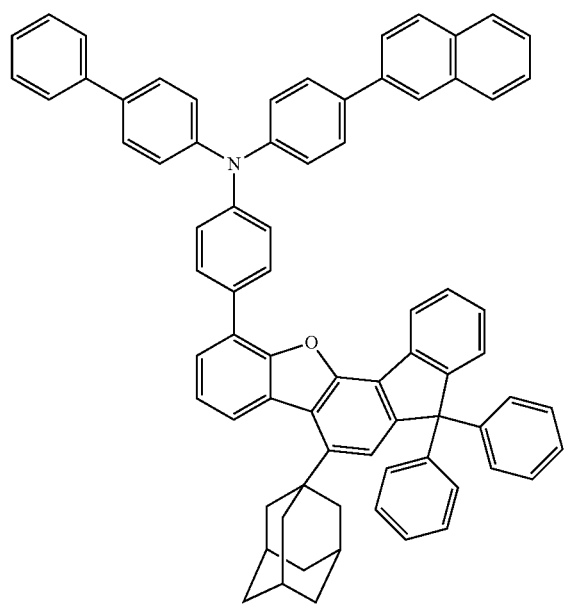
[Compound 43]
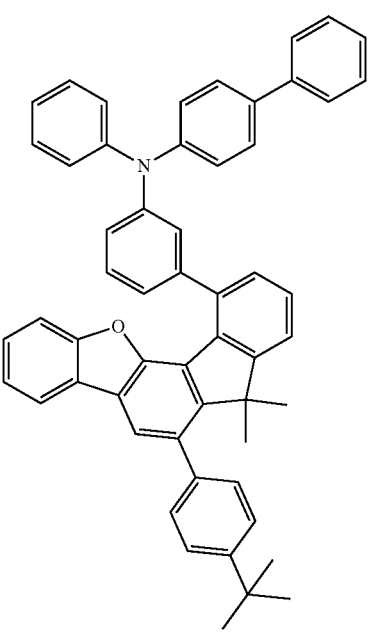
[Compound 41]
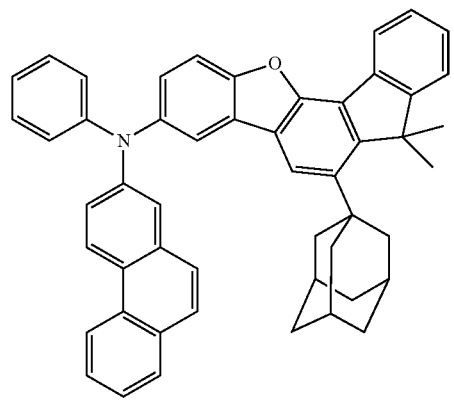

[Compound 44]
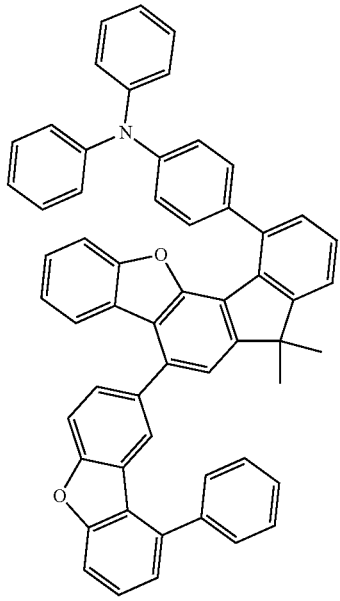
[Compound 45]
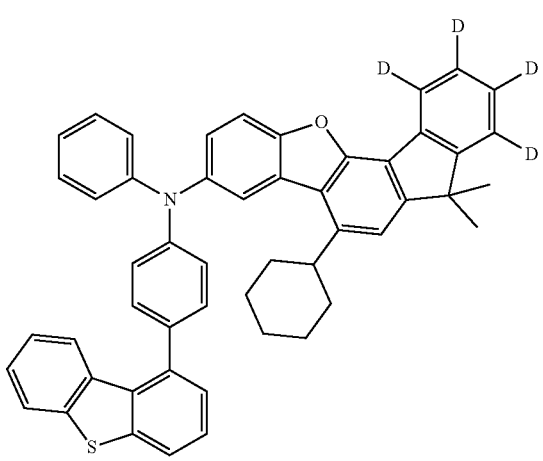
[Compound 46]
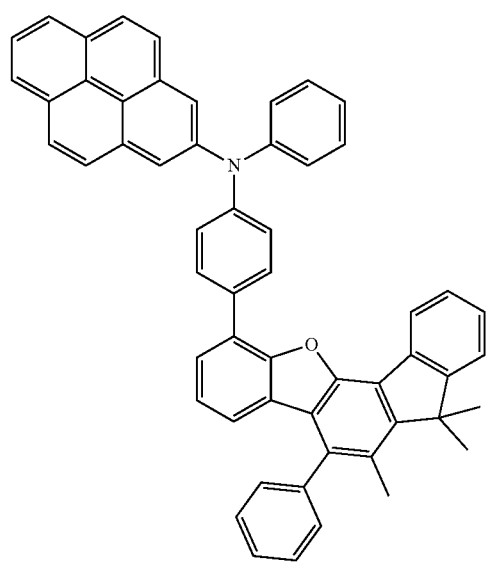
[Compound 47]
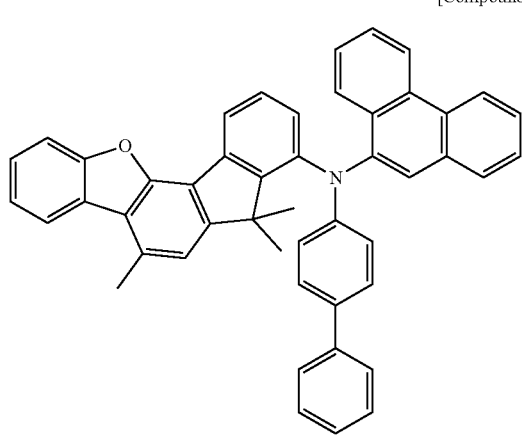
[Compound 48]
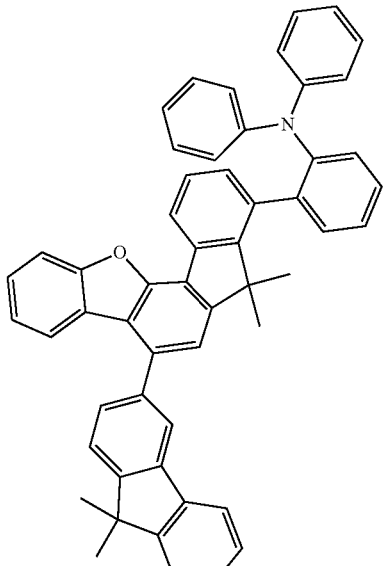
[Compound 49]
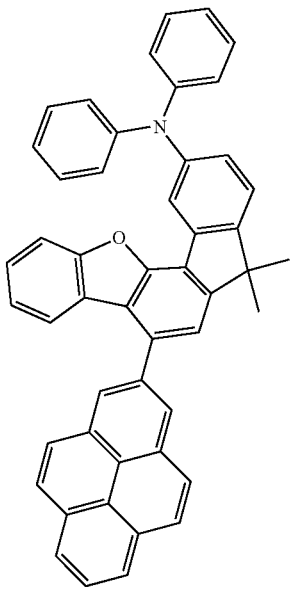

-continued

[Compound 50]
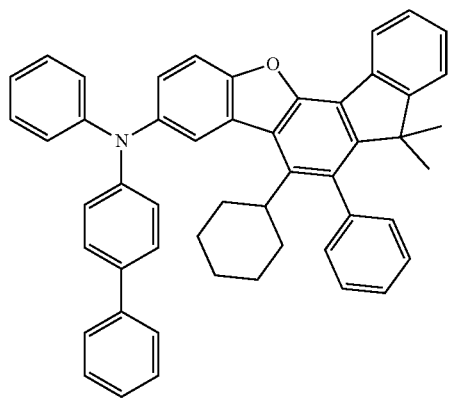

[Compound 51]
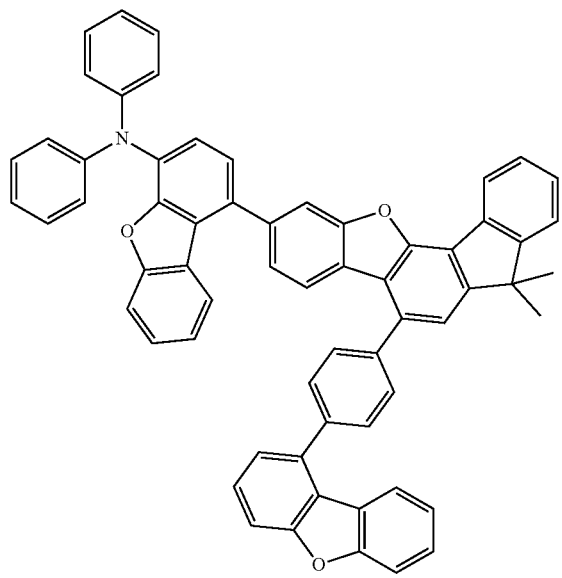

[Compound 52]
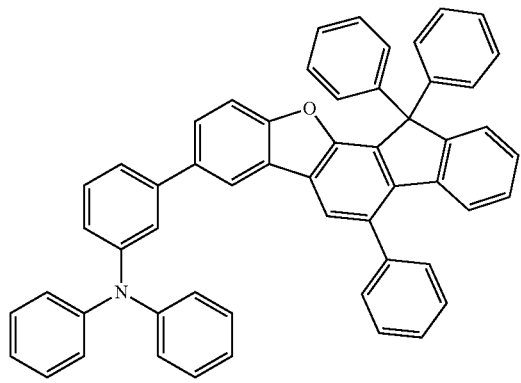

-continued

[Compound 53]
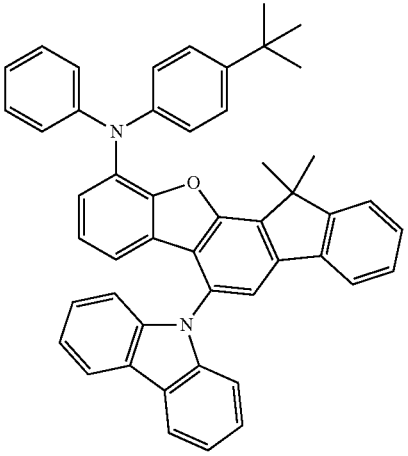

[Compound 54]

In a more particular embodiment, the present disclosure provides an organic light-emitting diode comprising a first electrode; a second electrode facing the first electrode; and an organic layer interposed between the first electrode and the second electrode, wherein the organic layer comprises at least one of the organic light-emitting compounds represented by Chemical Formula A or B. Having such a structural characteristic, the organic light-emitting diode according to the present disclosure can exhibit high efficiency and/or a long lifetime.

In the present disclosure, the phrase "(an organic layer) includes at least one organic compound" may be construed to mean that "(an organic layer) may include a single organic compound species or two or more different species of organic compounds falling within the scope of the present disclosure".

In a particular embodiment of the present disclosure, the organic light-emitting diode comprises the first electrode as an anode, the second electrode as a cathode, and an organic layer interposed between the anode and the cathode, wherein the organic layer includes a hole transport layer or a hole injection layer for which the light-emitting compound according to the present disclosure may be used, and the organic layer may further include at least one selected from among a light-emitting layer, a functional layer capable of both hole injection and hole transport, an electron transport layer, and an electron injection layer.

That is, the organic light-emitting diode according to the present disclosure may employ at least one of the organic light-emitting compounds represented by Chemical Formula A or Chemical Formula B as a material for the hole transport layer or the hole injection layer.

More particularly, the organic light-emitting diode according to the present disclosure comprises: an anode as a first electrode, a cathode as a second electrode, and a hole transport layer and a light-emitting layer disposed between the anode and the cathode, the hole transport layer including a first hole transport layer and a second hole transport layer disposed between the first hole transport layer and the light-emitting layer and employing materials that differ from the first hole transport layer to the second hole transport layer, wherein the organic light-emitting compound according to the present disclosure is used in the second hole transport layer.

In more particular embodiments of the present disclosure, the organic light-emitting diode may comprise: an anode as a first electrode; a cathode as a second electrode; a light-emitting layer between the anode and the cathode; a hole injection layer, a first hole transport layer, and a second hole transport layer in that order between the anode and the light-emitting layer; and an electron transport layer and an electron injection layer in that order between the light-emitting layer and the cathode.

According to an embodiment, the light-emitting layer in the organic light-emitting diode of the present disclosure comprises a host and a dopant, wherein the host may include an anthracene derivative represented by the following Chemical Formula C, but without limitations thereto:

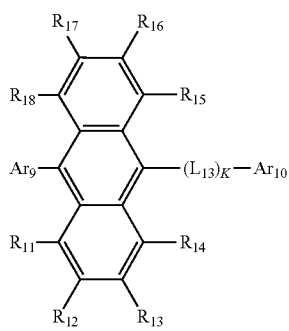

[Chemical Formula C]

wherein, substituents $R_{11}$ to $R_{18}$, which may be the same or different, are each independently any one selected from, a hydrogen atom, a deuterium atom, a substituted or unsubstituted alkyl of 1 to 30 carbon atoms, an alkenyl of 2 to 24 carbon atoms, an alkynyl of 2 to 24 carbon atoms, a substituted or unsubstituted aryl of 6 to 50 carbon atoms, a substituted or unsubstituted cycloalkyl of 3 to 30 carbon atoms, a substituted or unsubstituted heterocycloaryl of 1 to carbon atoms, a substituted or unsubstituted heteroaryl of 2 to 50 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted aryl thioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a nitro, a cyano, and a halogen;

substituents $Ar_9$ and $Ar_{10}$, which may the same or different, are each independently any one selected from among a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms, and a substituted or unsubstituted heteroaryl of 2 to 50 carbon atoms;

linker $L_{13}$ is a single bond or any one selected from among a substituted or unsubstituted arylene of 6 to 20 carbon atoms, and a substituted or unsubstituted heteroarylene of 2 to 20 carbon atoms, k is an integer of 1 to 3, under which when k is 2 or greater, the corresponding $L_{13}$'s are the same or different.

In a more concrete host compound represented by Chemical Formula C, $Ar_9$ may be a substituent represented by the following Chemical Formula C-1:

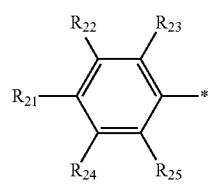

[Chemical Formula C-1]

wherein substituents $R_{21}$ to $R_{25}$, which may the same or different, are as defined above for $R_1$ to $R_{10}$, and may form a saturated or unsaturated ring between adjacent radicals thereof. In this case, the linker $L_{13}$ may be a single bond or a substituted or unsubstituted arylene of 6 to 20 carbon atoms, and k is an integer of 1 or 2, wherein when k is 2, the corresponding $L_{13}$'s may be the same or different.

In an embodiment, the anthracene derivative may be any one selected from compounds represented by the following [Chemical Formula 22] to [Chemical Formula 60], but without limitations thereto:

<Chemical Formula 22>

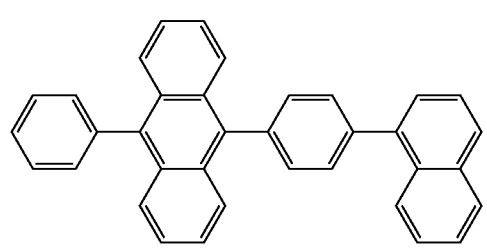

<Chemical Formula 23>

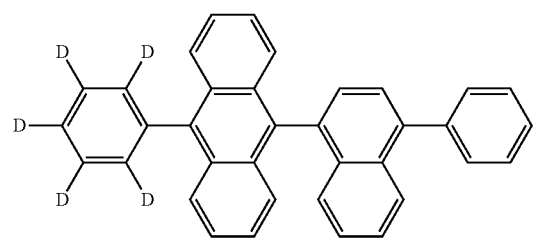

<Chemical Formula 24>
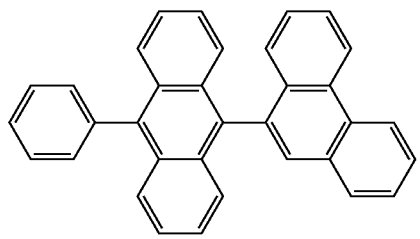
<Chemical Formula 25>
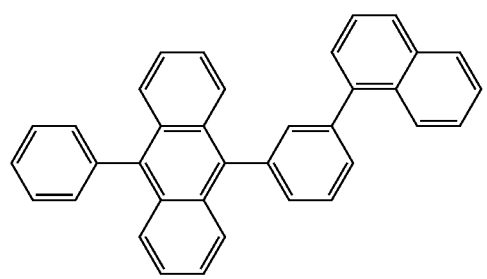
<Chemical Formula 26>
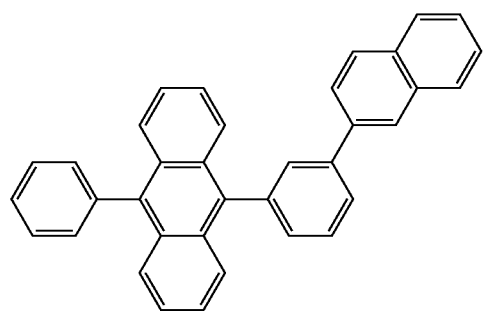
<Chemical Formula 27>
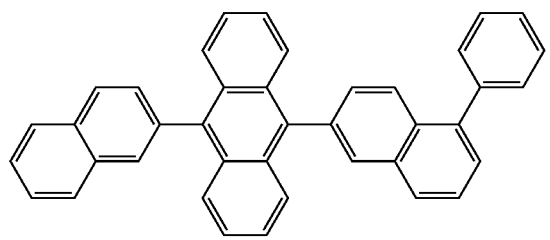
<Chemical Formula 28>
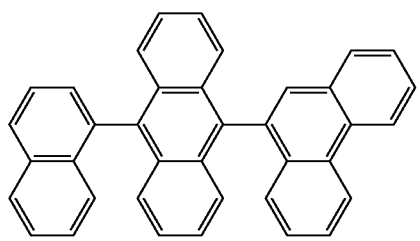
<Chemical Formula 29>
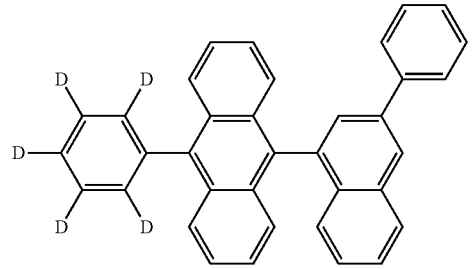
<Chemical Formula 30>
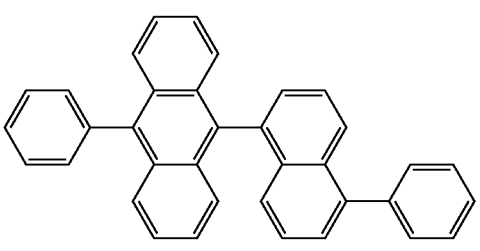
<Chemical Formula 31>
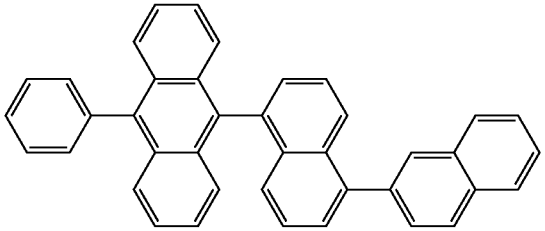
<Chemical Formula 32>
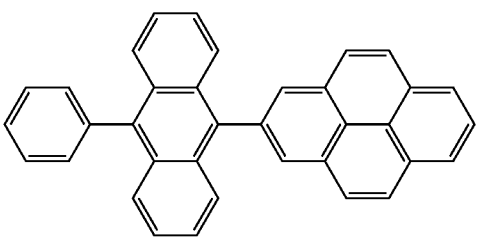
<Chemical Formula 33>
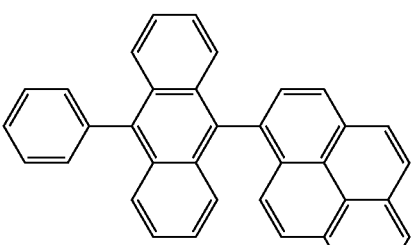
<Chemical Formula 34>
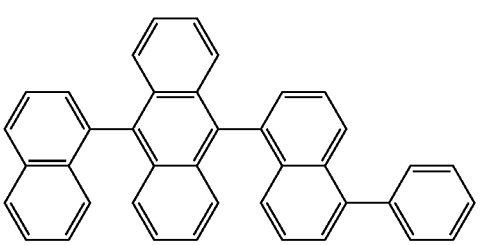

<Chemical Formula 35>
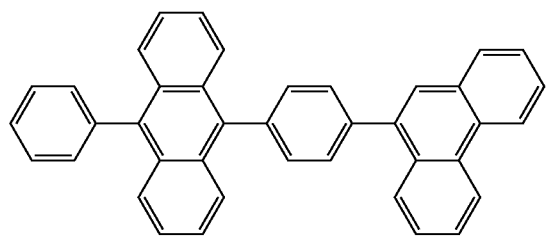
<Chemical Formula 36>
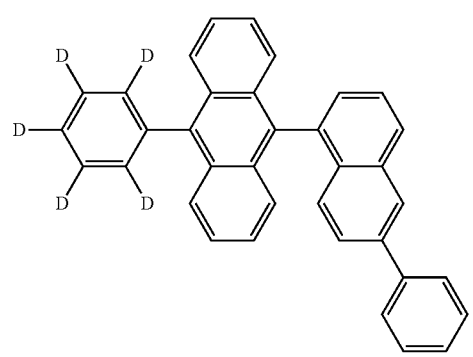
<Chemical Formula 37>
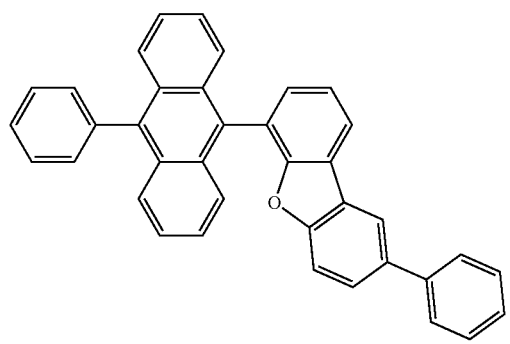
<Chemical Formula 38>
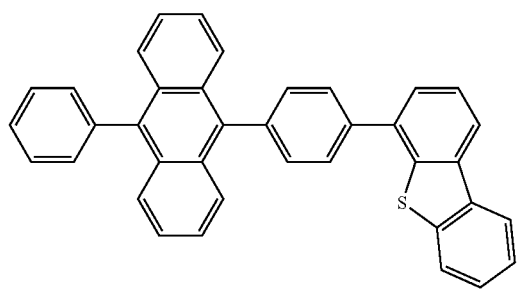
<Chemical Formula 39>
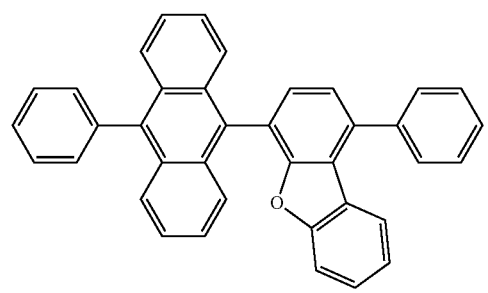
<Chemical Formula 40>
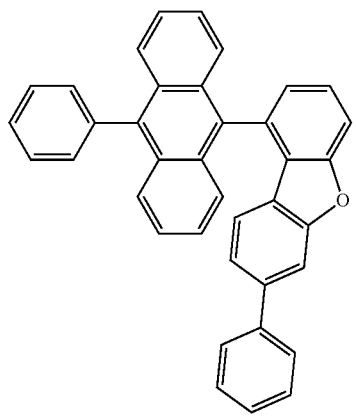
<Chemical Formula 41>
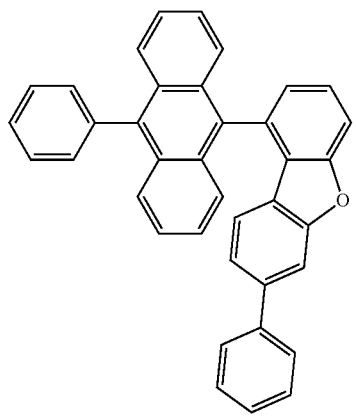
<Chemical Formula 42>
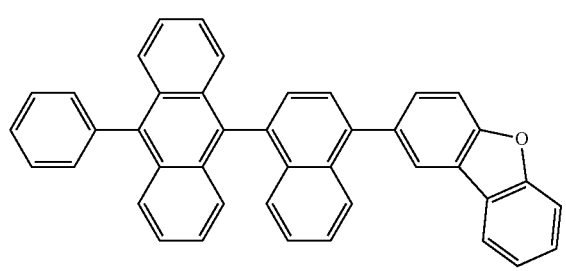

<Chemical Formula 43>
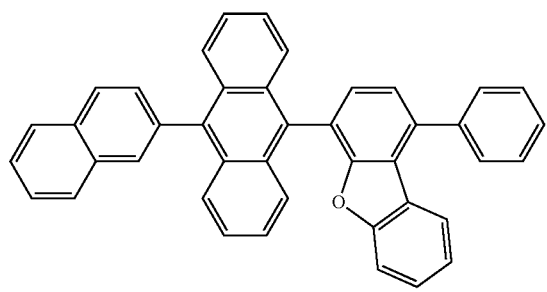
<Chemical Formula 44>
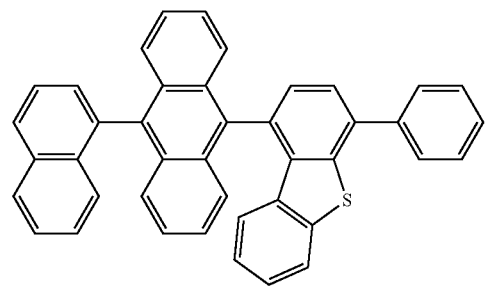
<Chemical Formula 45>
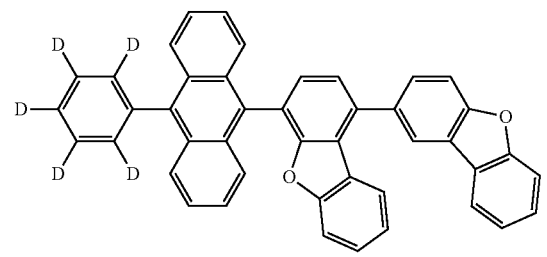
<Chemical Formula 46>
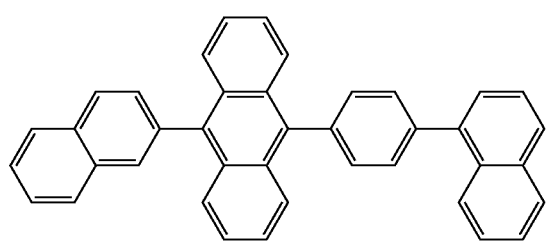
<Chemical Formula 47>
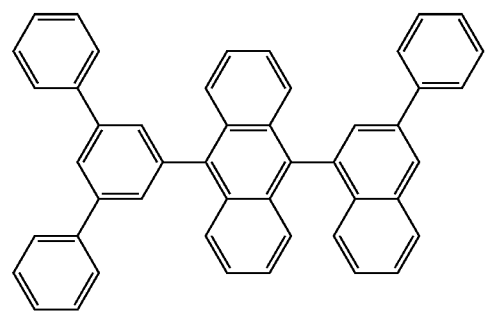
<Chemical Formula 48>
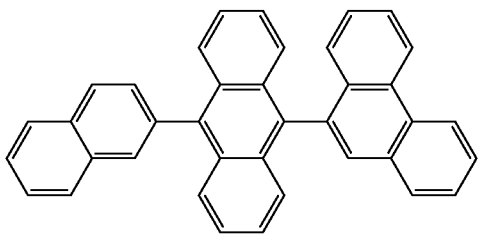
<Chemical Formula 49>
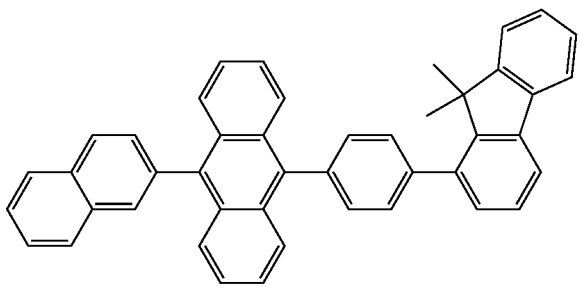
<Chemical Formula 50>
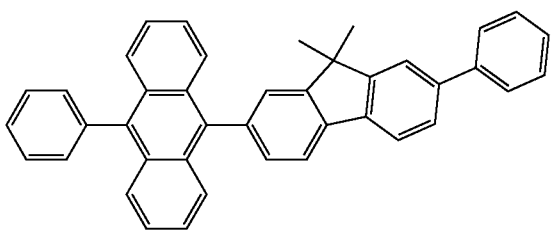
<Chemical Formula 51>
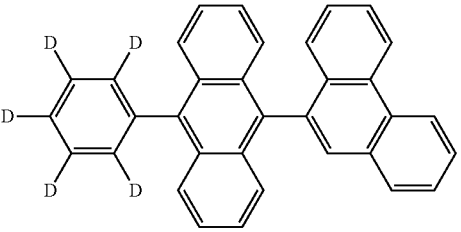
<Chemical Formula 52>
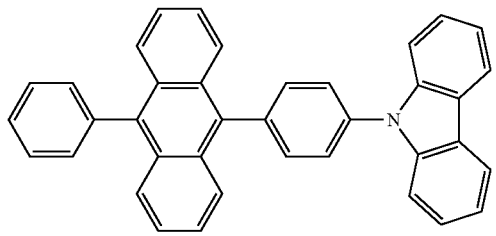
<Chemical Formula 53>
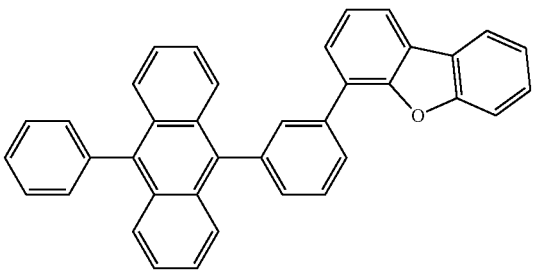

<Chemical Formula 54>
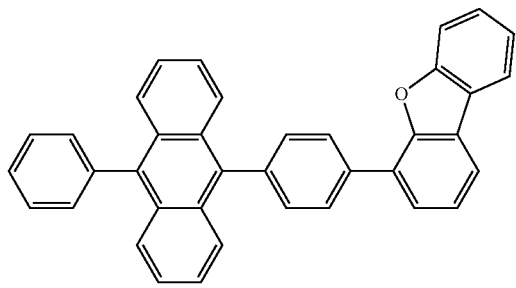
<Chemical Formula 55>
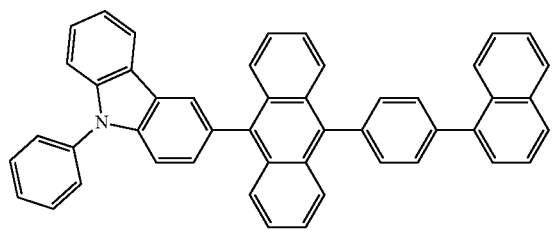
<Chemical Formula 56>
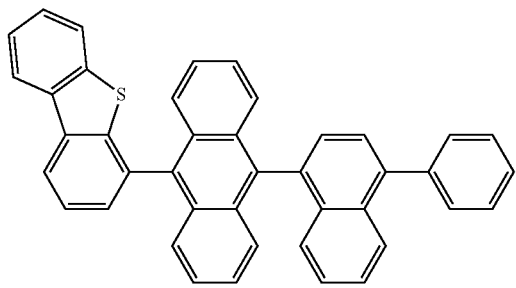
<Chemical Formula 57>
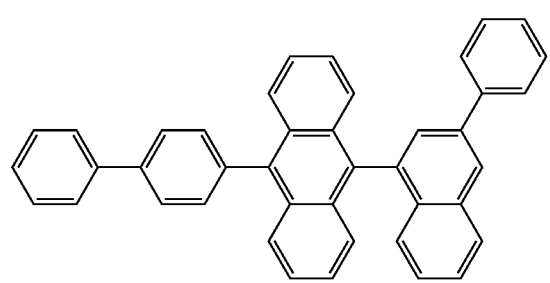
<Chemical Formula 58>
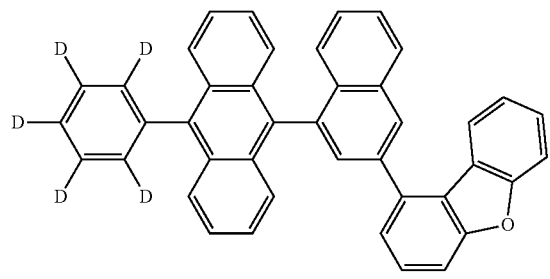
<Chemical Formula 59>
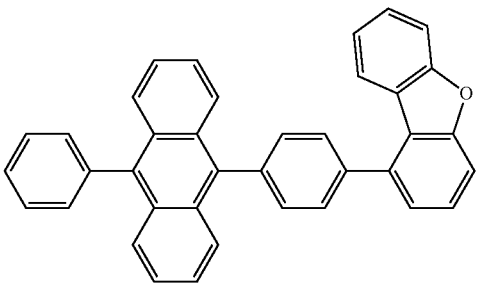
<Chemical Formula 60>
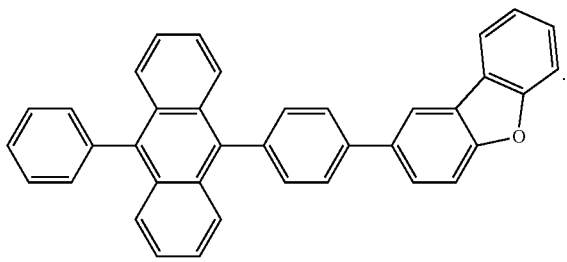
In addition, the dopant compound used in the light-emitting layer may include at least one of the compounds represented by the following Chemical Formulas D1 to D5:
[Chemical Formula D1]
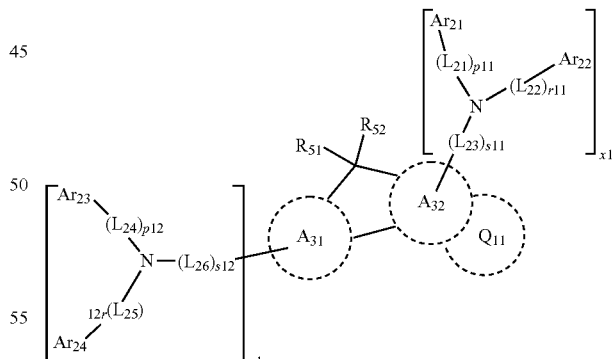
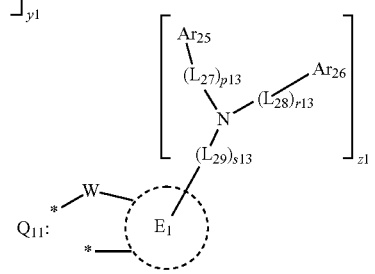

-continued

[Chemical Formula D2]

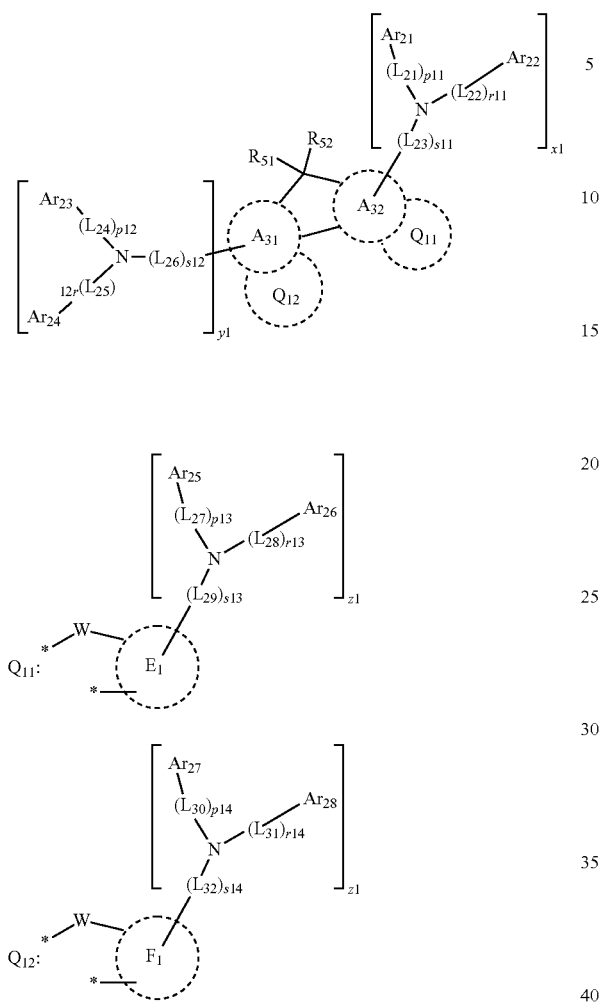

wherein,

A$_{31}$, A$_{32}$, E$_1$, and F$_1$, which may be the same or different, are each independently any one selected from a substituted or unsubstituted aromatic hydrocarbon ring of 6 to 50 carbon atoms, and a substituted or unsubstituted heteroaromatic ring of 2 to 40 carbon atoms, wherein two adjacent carbon atoms within the aromatic ring of A$_{31}$ and two adjacent carbon atoms within the aromatic ring of A$_{32}$ form a 5-membered ring with a carbon atom connected to both substituents R$_{51}$ and R$_{52}$, thus establishing a fused ring structure;

linkers L$_{21}$ to L$_{32}$, which may be the same or different, are each independently any one selected from a single bond, a substituted or unsubstituted alkylene of 1 to 60 carbon atoms, a substituted or unsubstituted alkenylene of 2 to 60 carbon atoms, a substituted or unsubstituted akynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atom, and a substituted or unsubstituted heteroarylene of 2 to 60 carbon atoms; W is any one selected from among N—R$_{53}$, CR$_{54}$R$_{55}$, SiR$_{56}$R$_{57}$, GeR$_{58}$R$_{59}$, O, S, and Se;

substituents R$_{51}$ to R$_{59}$ and Ar$_{21}$ to Ar$_{28}$, which may be the same or different, are each independently any one selected from a hydrogen atom, a deuterium atom, a substituted or unsubstituted alkyl of 1 to carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted aryl thioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted alkylsilyl of 1 to 30 carbon atoms, a substituted or unsubstituted arylsilyl of 5 to 30 carbon atoms, a substituted or unsubstituted alkyl germanium of 1 to carbon atoms, a substituted or unsubstituted aryl germanium of 1 to 30 carbon atoms, a cyano, a nitro, and a halogen, wherein R$_{51}$ and R$_{52}$ may be connected to each other to form a mono- or polycyclic aliphatic or aromatic ring which may bear at least one heteroatom selected from among N, O, P, Si, S, Ge, Se, and Te as a ring member;

p11 to p14, r1 to r14, and s11 to s14 are each independently an integer of 1 to 3, under which when any of them is 2 or greater, the corresponding linkers L$_{21}$ to L$_{32}$ may be the same or different;

x1 is an integer of 1 or 2;

y1 and z1, which may be the same or different, are each independently an integer of 0 to 3;

a connection may be made between Ar$_{21}$ and Ar$_{22}$, between Ar$_{23}$ and Ar$_{24}$, between Ar$_{25}$ and Ar$_{26}$, and between Ar$_{27}$ and Ar$_{28}$ to form respective rings; and two adjacent carbon atoms of the A$_{32}$ ring moiety of Chemical Formula D1 may occupy respective positions * of Structural Formula Qui to form a fused ring, and two adjacent carbon atoms of the A$_{31}$ ring moiety of Chemical Formula D2 may occupy respective positions * of Structural Formula Q$_{12}$ to form a fused ring and two adjacent carbon atoms of the A$_{32}$ ring moiety of Chemical Formula D2 may occupy respective positions * of structural Formula Qui to form a fused ring;

[Chemical Formula D3]

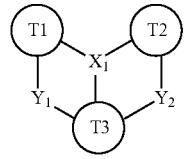

wherein,

X$_1$ is any one selected from the group consisting of B, P, and P=O;

T1 to T3, which may be the same or different, are each independently a substituted or unsubstituted aromatic hydrocarbon ring of 6 to 50 carbon atoms, or a substituted or unsubstituted heteroaromatic ring of 2 to 40 carbon atoms;

Y₁ is any one selected from among N—R61, CR62R63, O, S, and SiR64R65; and

Y2 is any one selected from among N—R66, CR66R68, O, S, and SiR69R70;

wherein R61 to R70 which may be the same or different, are each independently selected from among a hydrogen atom, a deuterium atom, a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted heteroaryl of 2 to 50 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted aryl thioxy of 5 to 30 carbon atoms, a substituted or unsubstituted alkylamine of 1 to 30 carbon atoms, a substituted or unsubstituted arylamine of 5 to 30 carbon atoms, a substituted or unsubstituted alkylsilyl of 1 to 30 carbon atoms, a substituted or unsubstituted arylsilyl of 5 to 30 carbon atoms, a cyano, and a halogen wherein R61 to R70 may each be linked to at least one of T₁ to T₃ to further form a mono- or polycyclic aliphatic or aromatic ring;

[Chemical Formula D4]

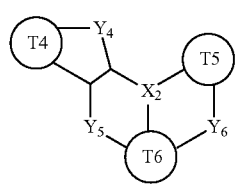

[Chemical Formula D5]

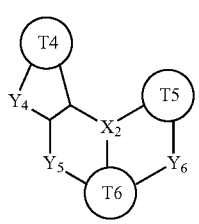

wherein,

X₂ is any one selected from among B, P, and P=O;

T4 to T6 are as defined for T1 to T3 in [Chemical Formula D3]; and

Y₄ to Y₆ are as defined for Y1 to Y₂ in [Chemical Formula D3];

wherein the term "substituted" in the expression "substituted or unsubstituted" used for [Chemical Formula D1] to [Chemical Formula D5] means having at least one substituent selected from the group consisting of a deuterium atom, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a heteroarylamino of 1 to 24 carbon atoms, an alkylsilyl of 1 to 24 carbon atoms, an arylsilyl of 6 to 24 carbon atoms, and an aryloxy of 6 to 24 carbon atoms.

In the boron compounds, represented by Chemical Formulas D3 to chemical Formula D5, for use as the dopant compound according to the present disclosure, the aromatic hydrocarbon rings or the heteroaromatic rings of T1 to T6 may have a deuterium atom, an alkyl of 1 to 24 carbon atoms, an aryl of 6 to 24 carbon atoms, an alkylamino of 1 to 24 carbon atoms, or an arylamino of 6 to 24 carbon atoms as a substituent thereon, wherein the alkyl group or aryl group in the alkylamino of 1 to 24 carbon atoms and the arylamino of 6 to 24 carbon atoms may be connected to each other, and preferably may have an alkyl of 1 to 12 carbon atoms, an aryl of 6 to 18 carbon atoms, an alkylamino of 1 to 12 carbon atoms, or an arylamino of 6 to 18 carbon atoms as a substituent thereon, wherein the alkyl group or aryl group in the alkylamino of 1 to 12 carbon atoms and the arylamino of 6 to 18 carbon atoms may be connected to each other.

In addition, concrete examples of the dopant compounds represented by Chemical Formulas D1 to D2 include compounds represented by Chemical Formula d1 to Chemical Formula d239:

<Chemical Formula d1>

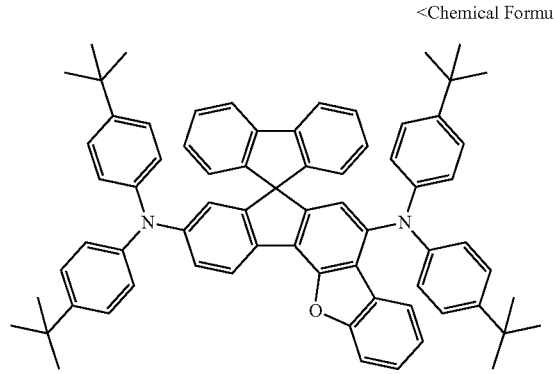

<Chemical Formula d2>

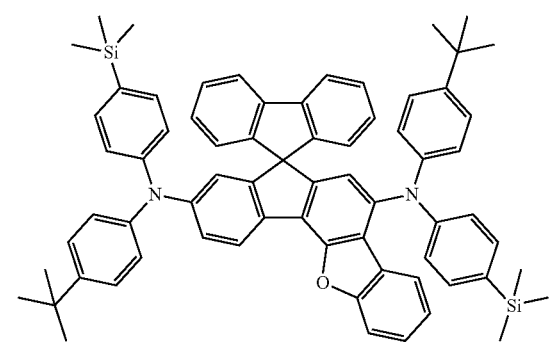

-continued
<Chemical Formula d3>
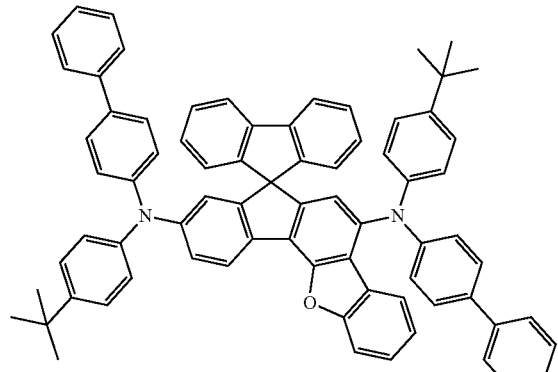
<Chemical Formula d4>
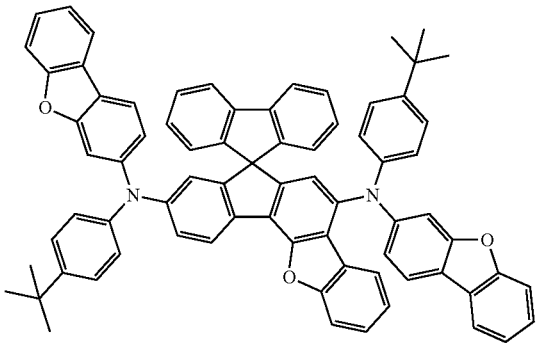
<Chemical Formula d5>
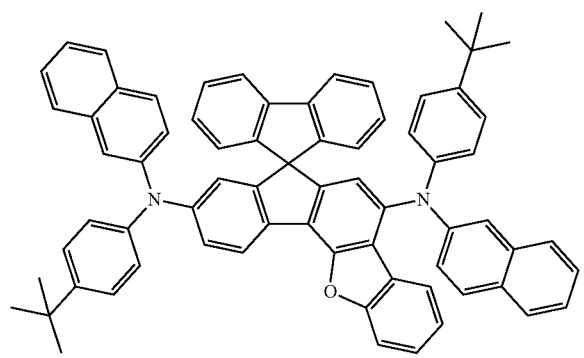
<Chemical Formula d6>
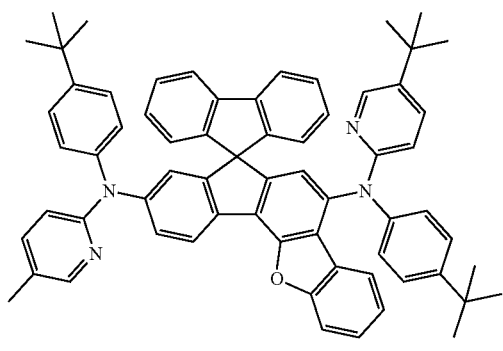
<Chemical Formula d7>
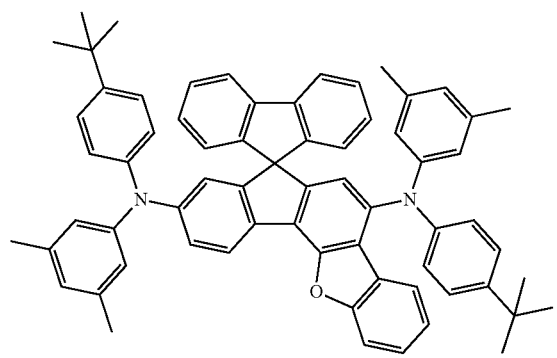
<Chemical Formula d8>
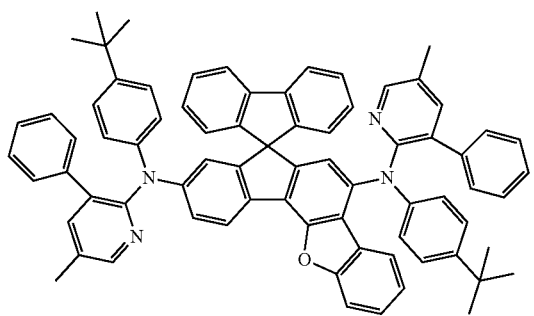
<Chemical Formula d9>
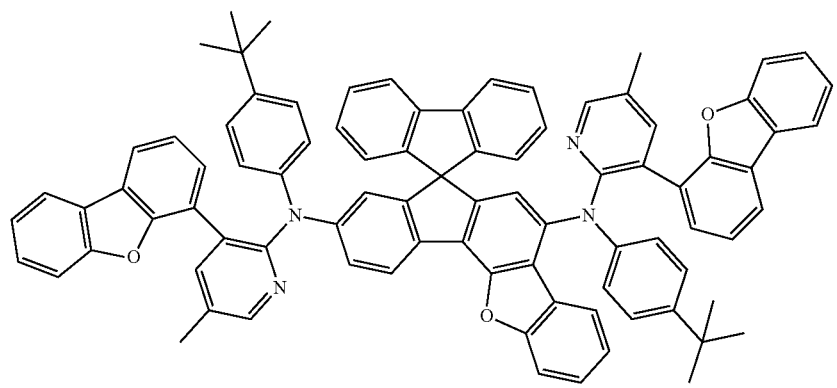

-continued
<Chemical Formula d10>
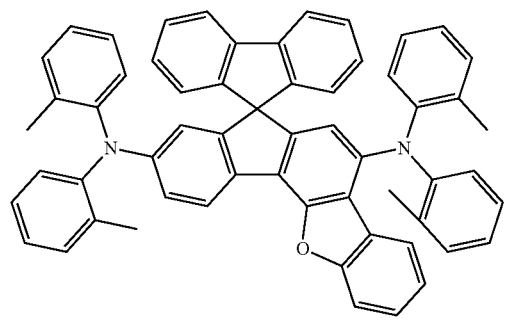
<Chemical Formula d11>
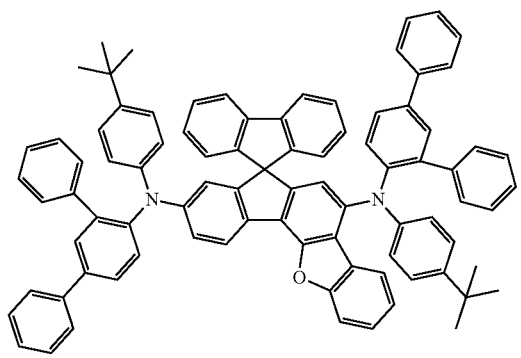
<Chemical Formula d12>
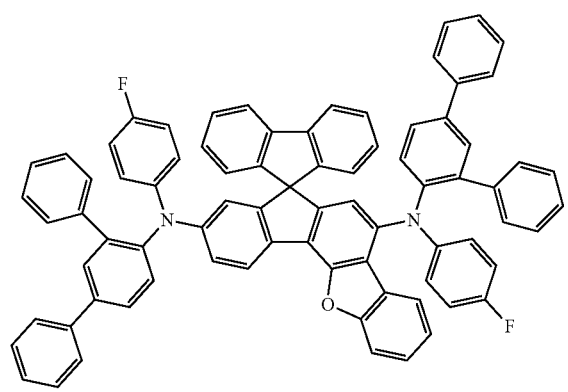
<Chemical Formula d13>
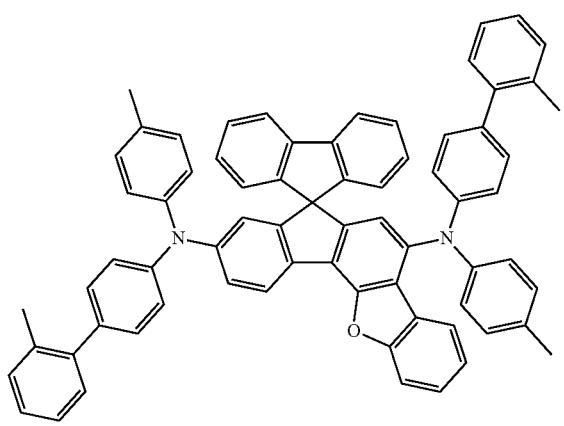
<Chemical Formula d14>
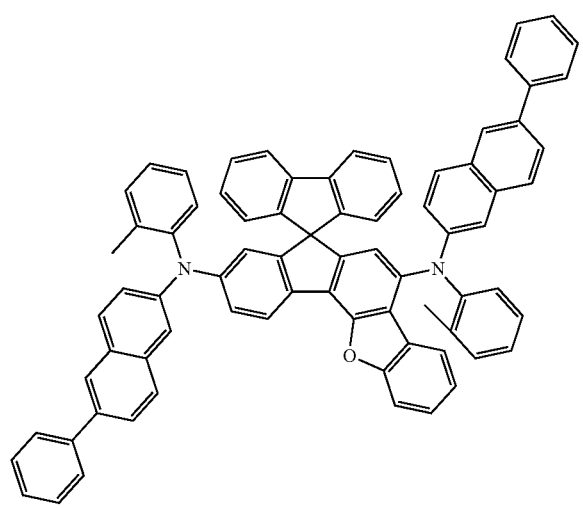
<Chemical Formula d15>
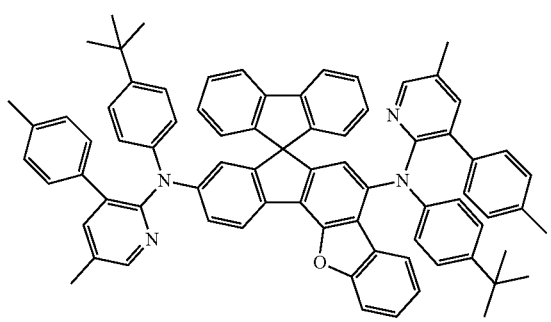

<Chemical Formula d16>
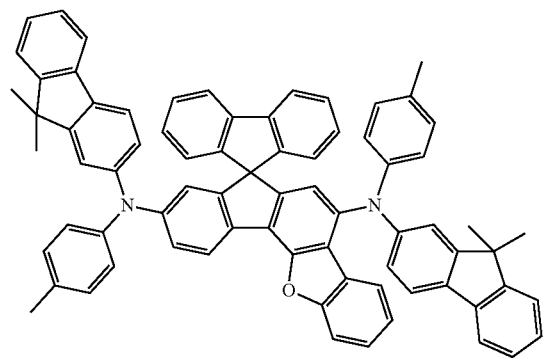
<Chemical Formula d17>
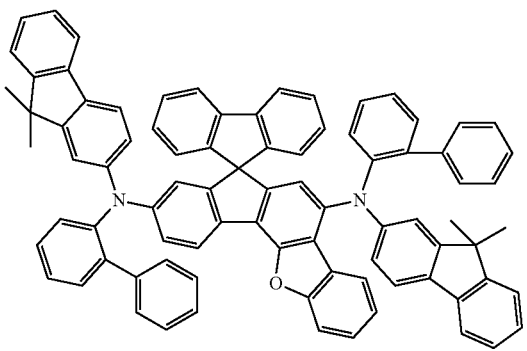
<Chemical Formula d18>
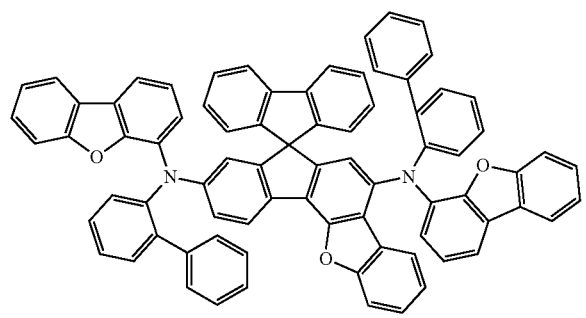
<Chemical Formula d19>
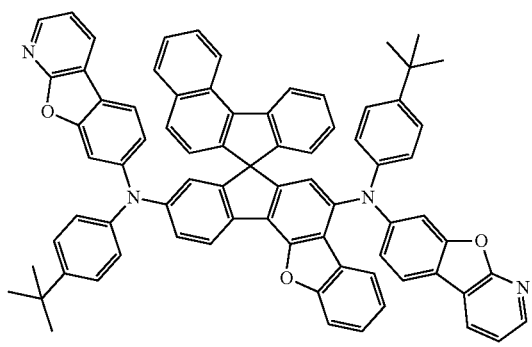
<Chemical Formula d20>
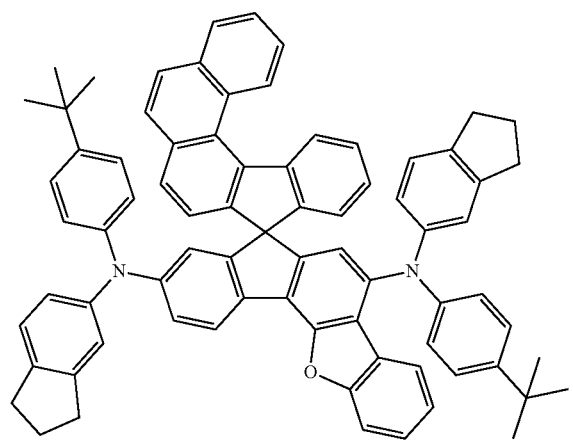
<Chemical Formula d21>
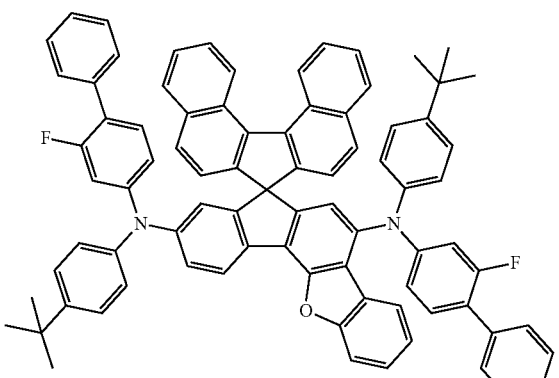
<Chemical Formula d22>
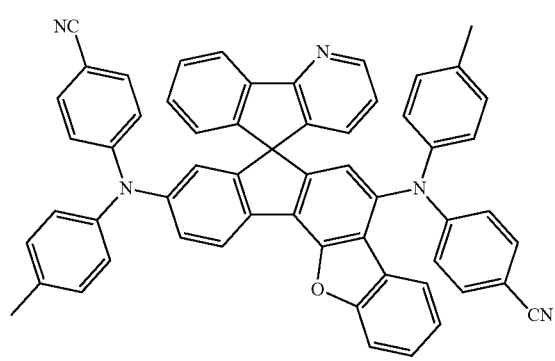

-continued
<Chemical Formula d23>
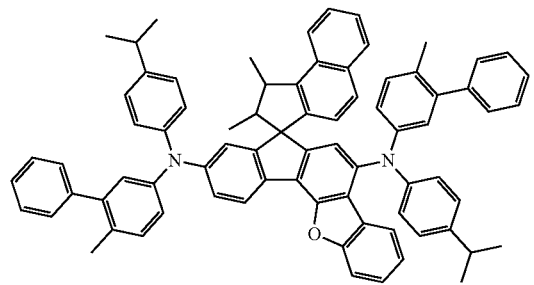
<Chemical Formula d24>
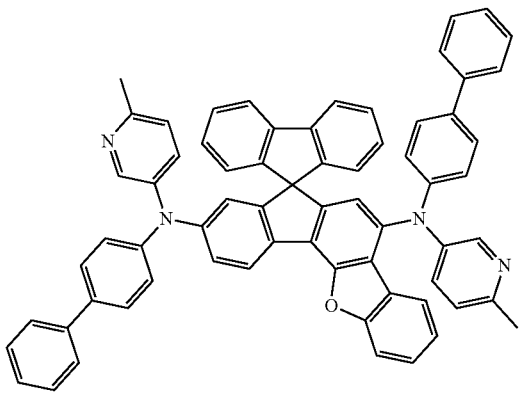
<Chemical Formula d25>
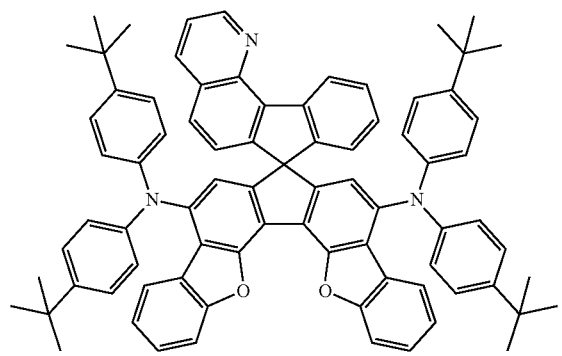
<Chemical Formula d26>
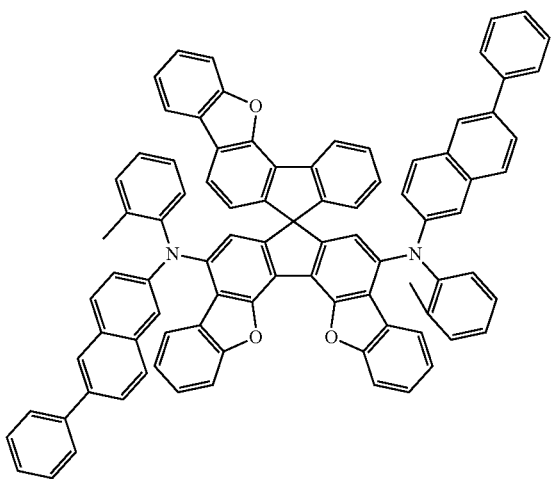
<Chemical Formula d27>
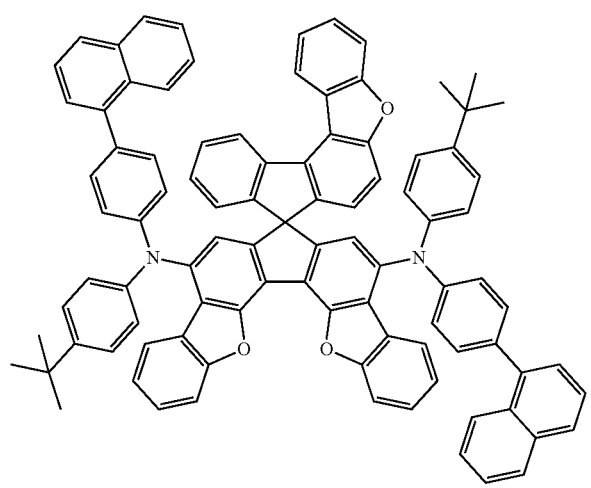

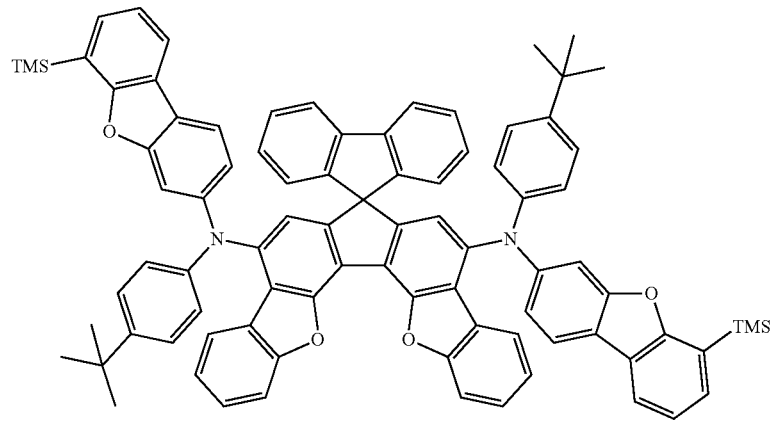
<Chemical Formula d28>
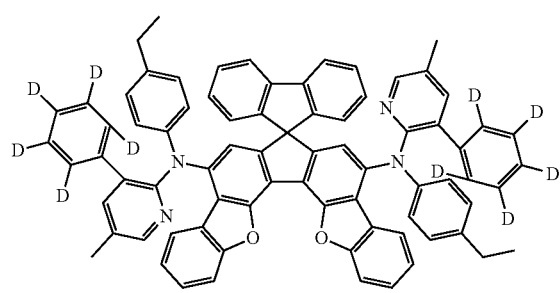
<Chemical Formula d29>
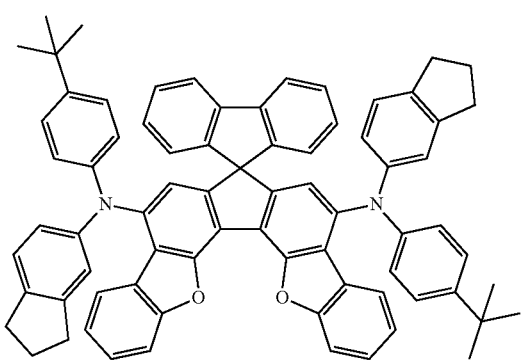
<Chemical Formula d30>
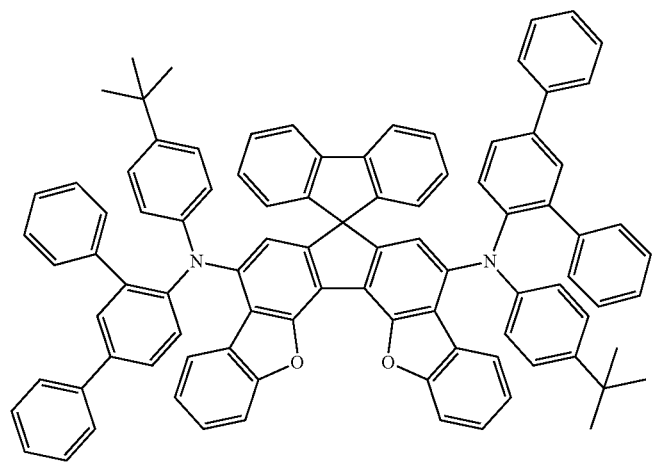
<Chemical Formula d31>
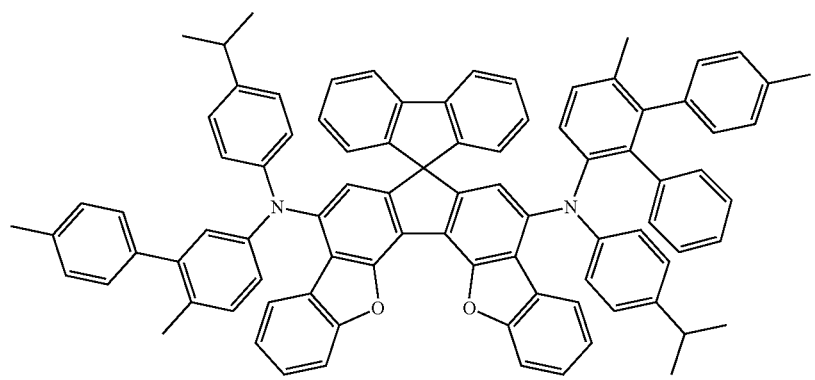
<Chemical Formula d32>

<Chemical Formula d33>
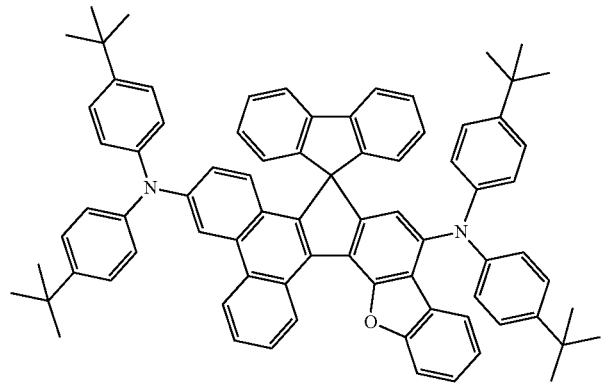
<Chemical Formula d34>
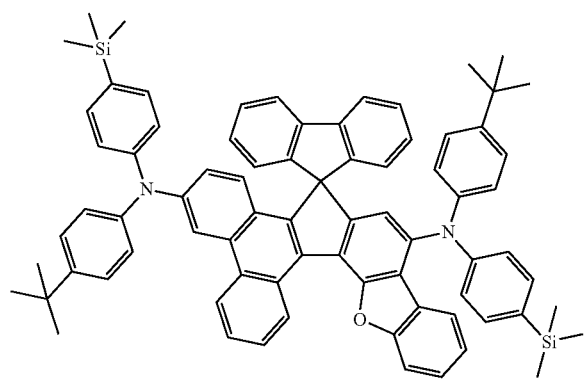
<Chemical Formula d35>
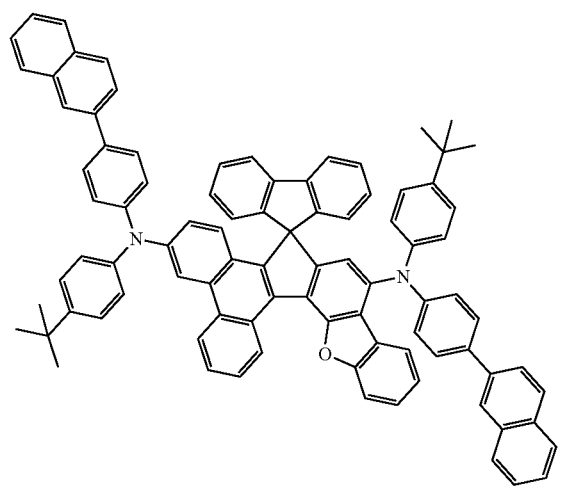
<Chemical Formula d36>
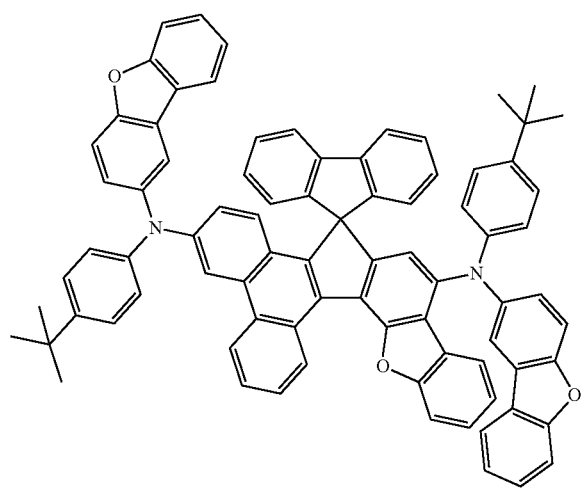
<Chemical Formula d37>
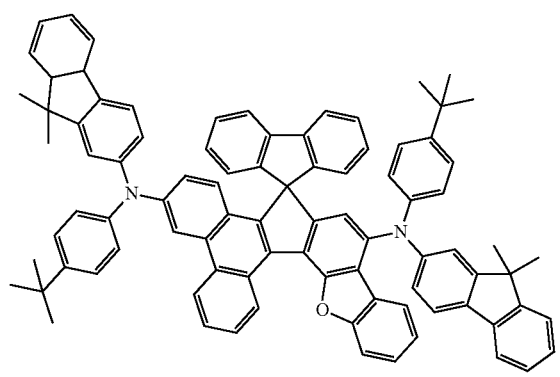

-continued
<Chemical Formula d38>
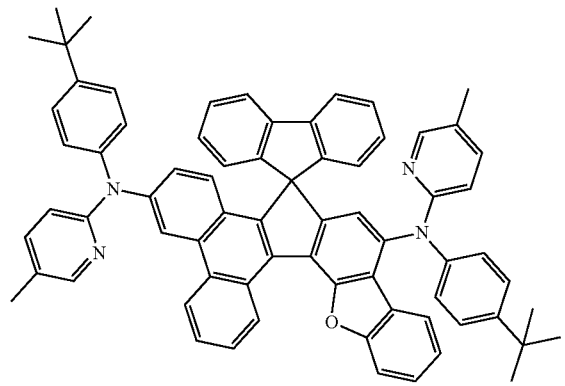
<Chemical Formula d39>
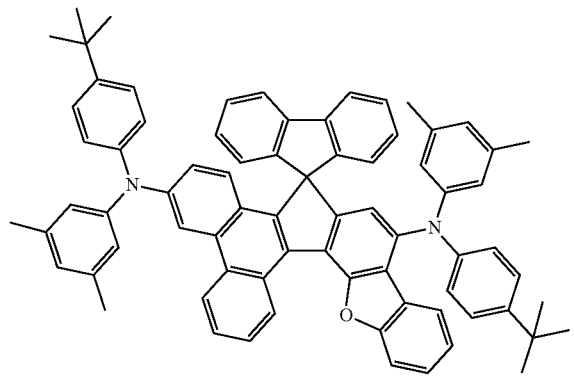
<Chemical Formula d40>
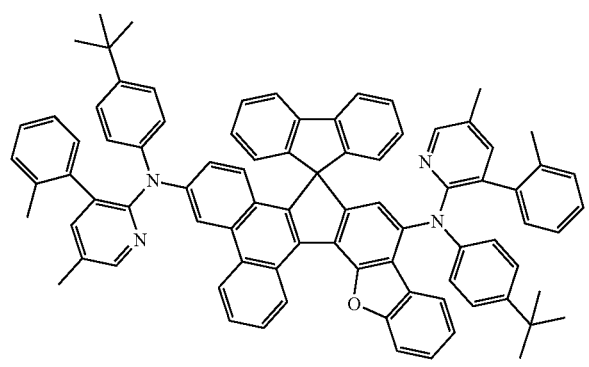
<Chemical Formula d41>
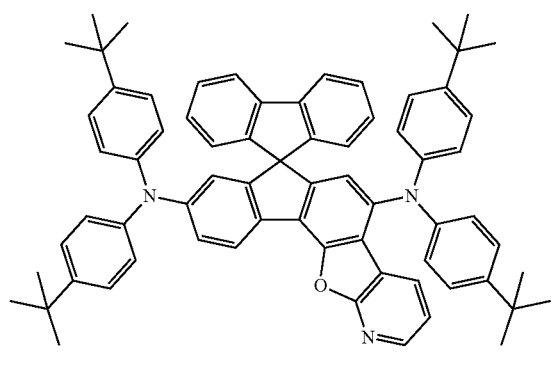
<Chemical Formula d42>
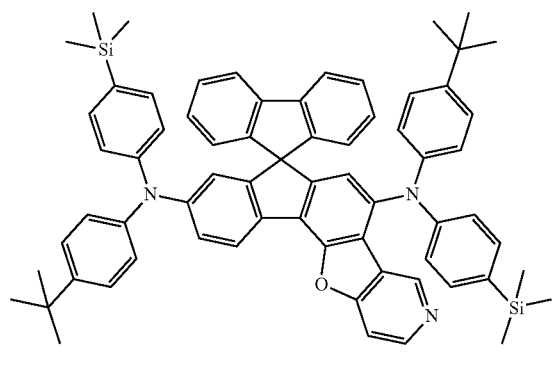
<Chemical Formula d43>
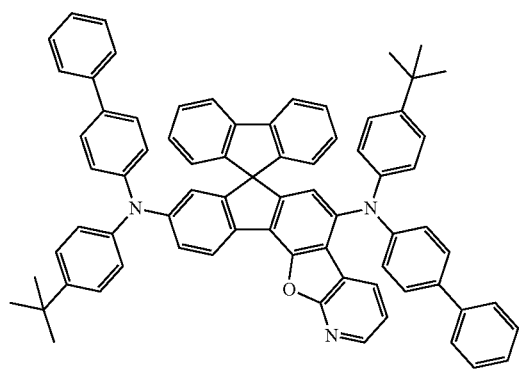
<Chemical Formula d44>
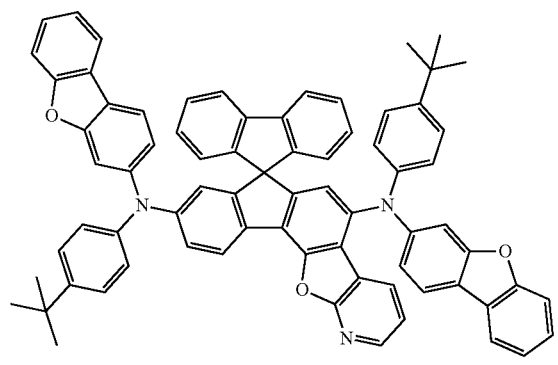
<Chemical Formula d45>
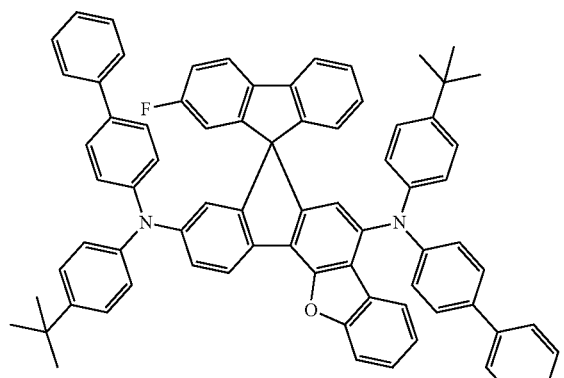

-continued
<Chemical Formula d46>
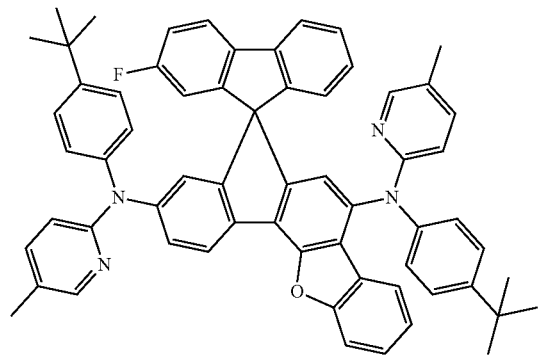
<Chemical Formula d47>
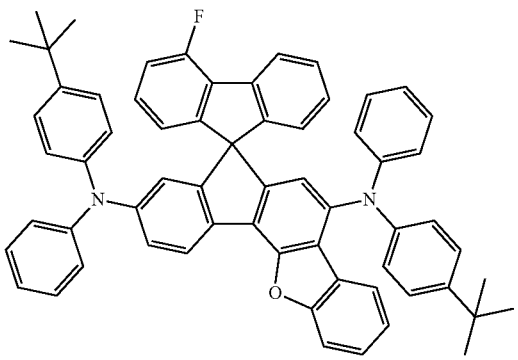
<Chemical Formula d48>
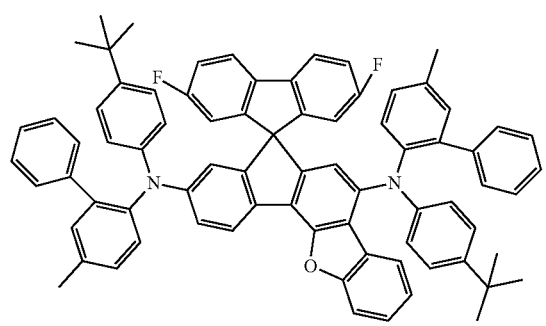
<Chemical Formula d49>
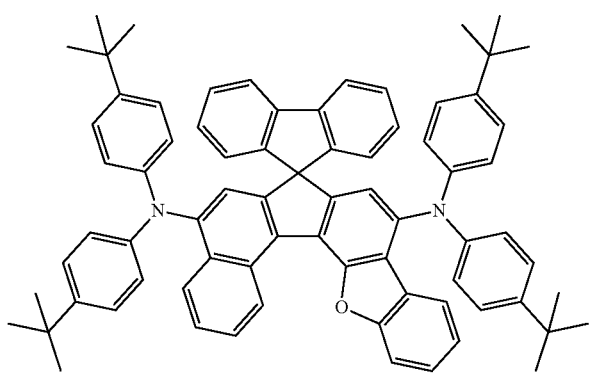
<Chemical Formula d50>
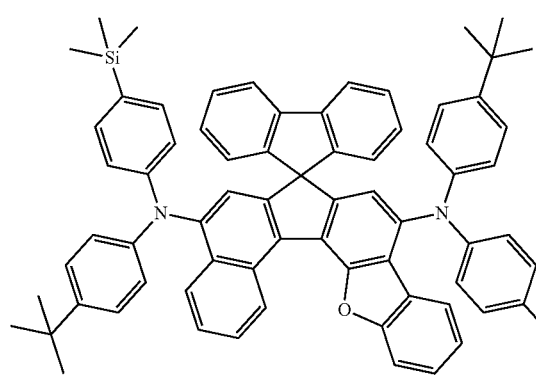
<Chemical Formula d51>
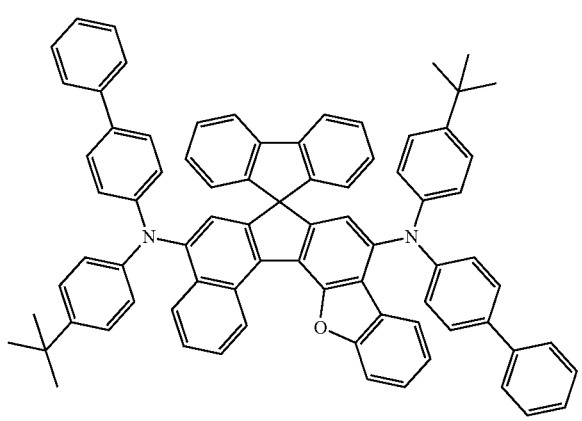
<Chemical Formula d52>
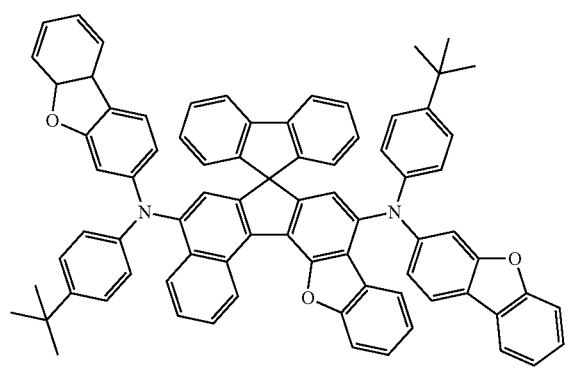
<Chemical Formula d53>
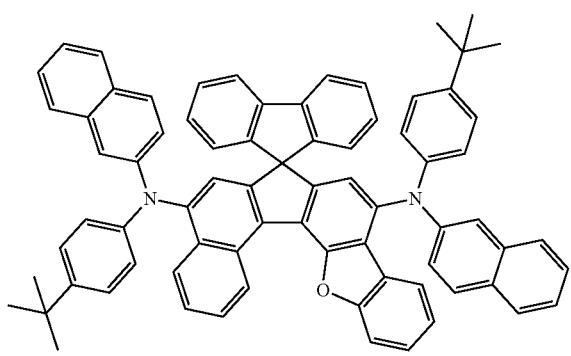

-continued
<Chemial Formula d54>
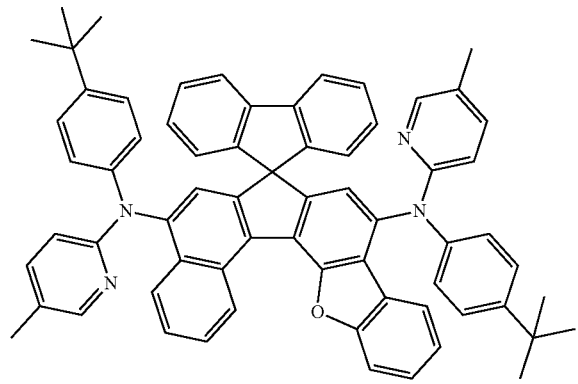
<Chemical Formula d55>
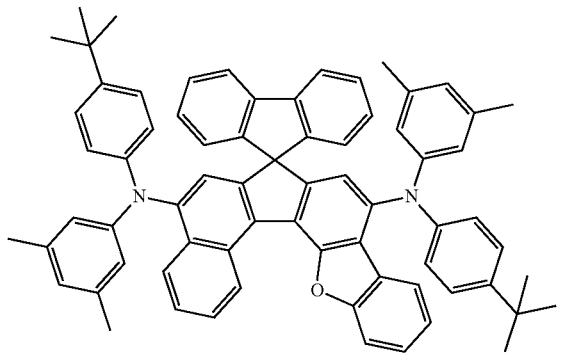
<Chemical Formula d56>
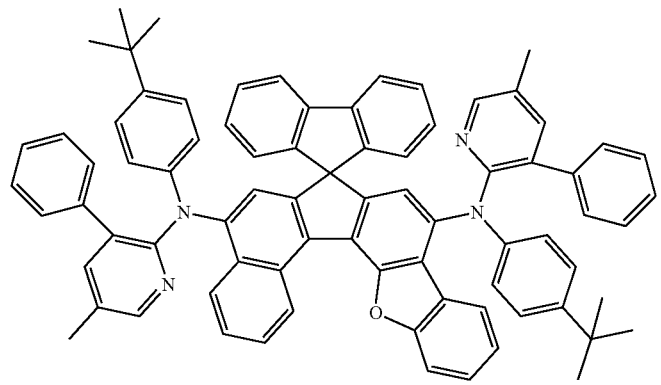
<Chemical Formula d57>
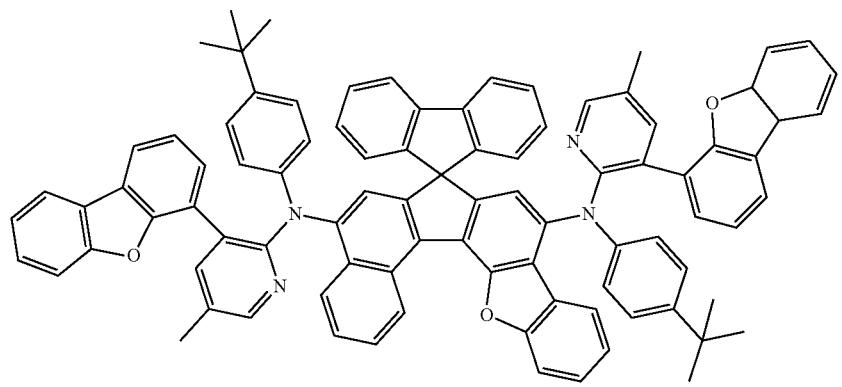
<Chemical Formula d58>
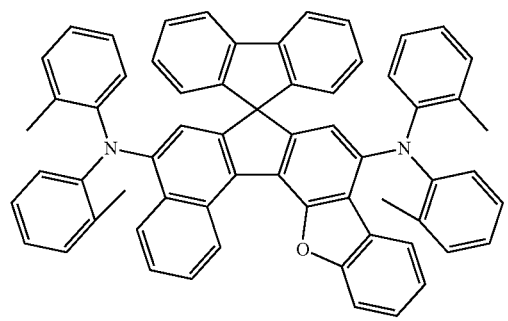
<Chemical Formula d59>
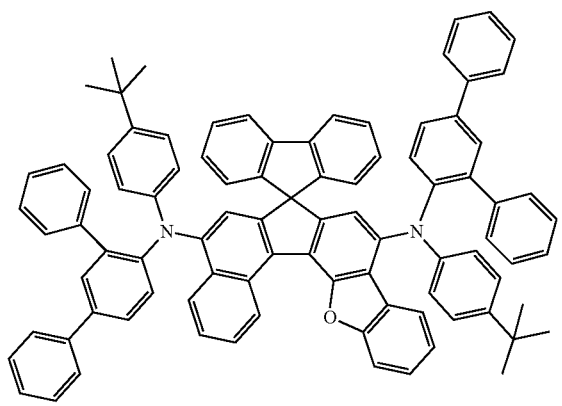

-continued
<Chemical Formula d60>
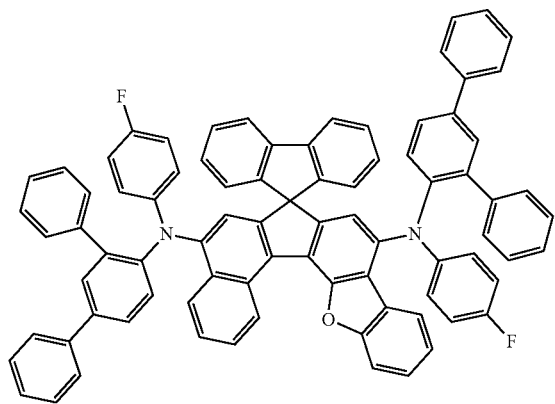
<Chemical Formula d61>
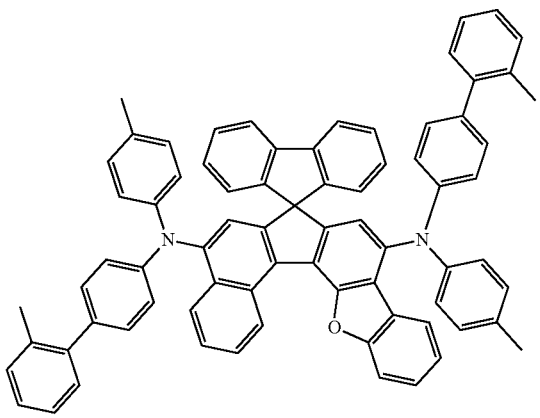
<Chemical Formula d62>
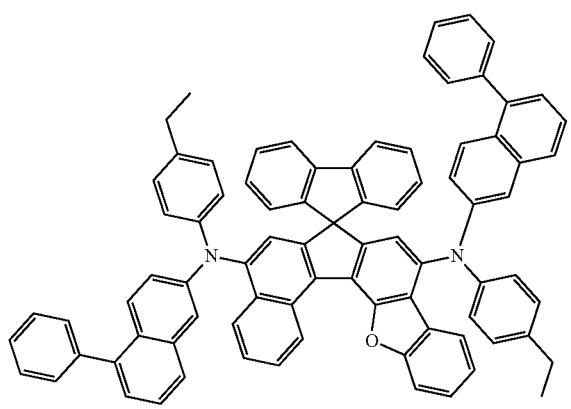
<Chemical Formula d63>
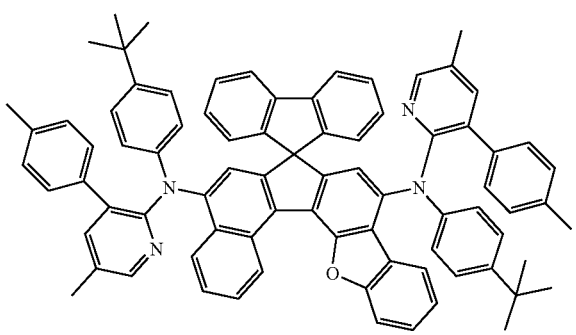
<Chemcial Formula d64>
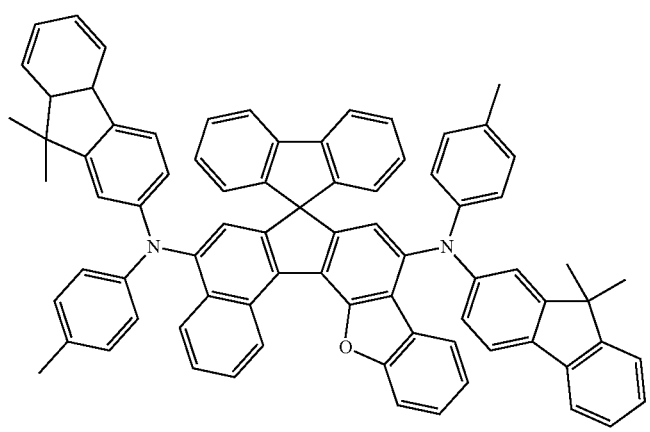

<Chemical Formula d65>
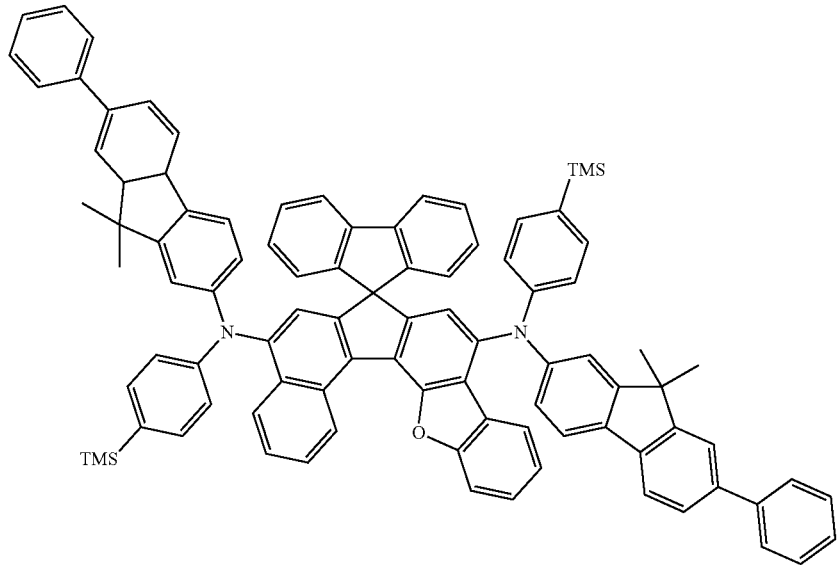
<Chemical Formula d66>   <Chemical Formula d67>
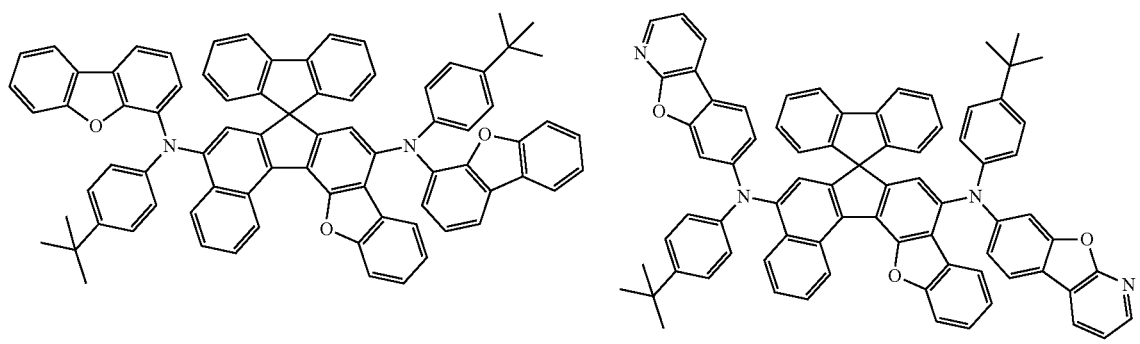
<Chemical Formula d68>   <Chemical Formula d69>
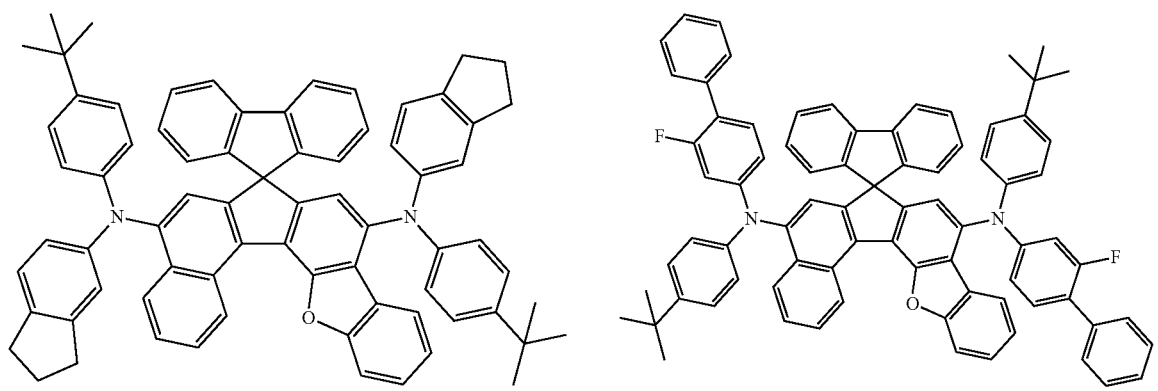

-continued
<Chemical Formula d70>
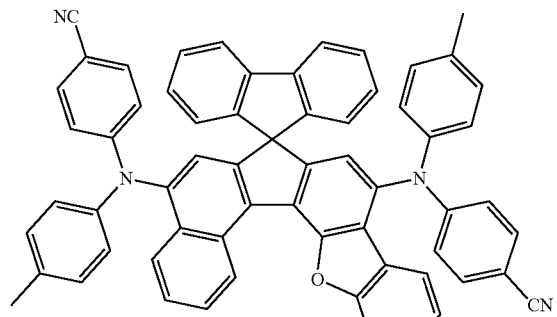
<Chemical Formula d71>
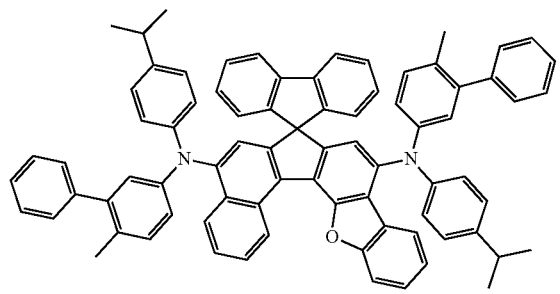
<Chemical Formula d72>
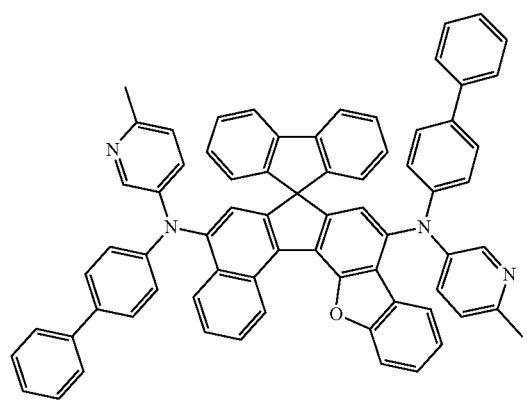
<Chemical Formula d73>
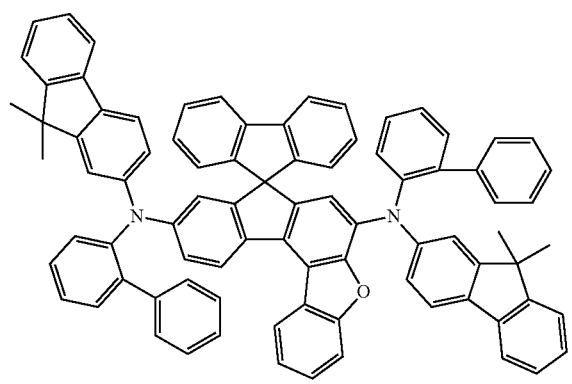
<Chemical Formula d74>
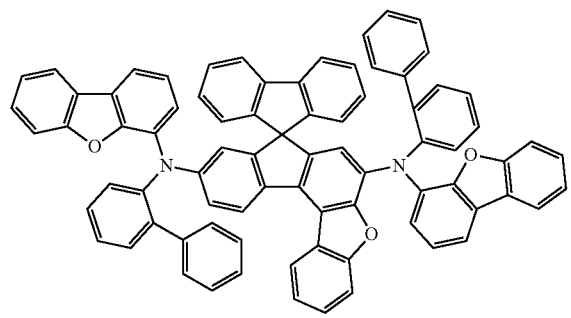
<Chemical Formula d75>
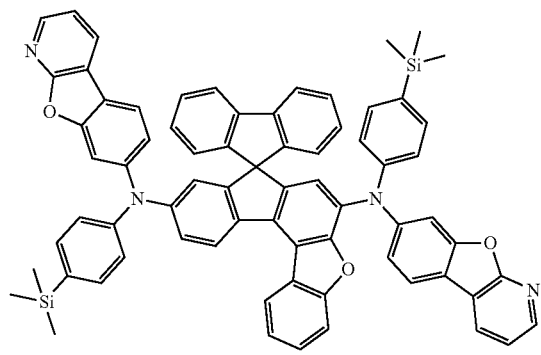
<Chemical Formula d76>
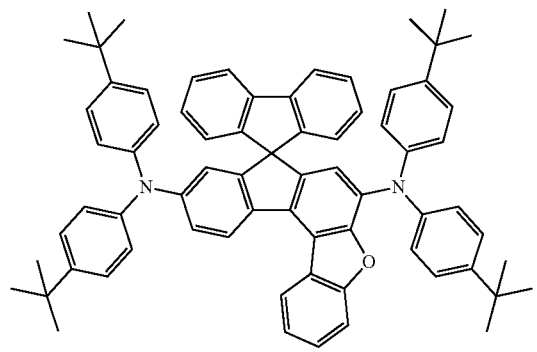
<Chemical Formula d77>
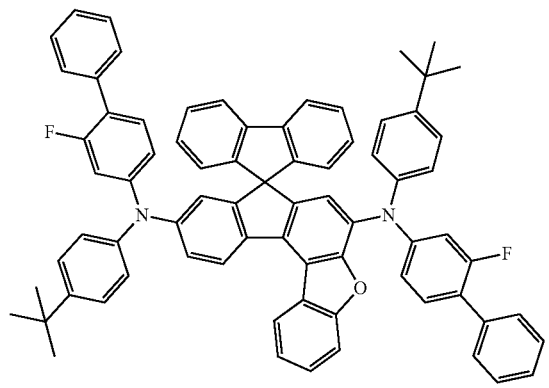

-continued
<Chemical Formula d78>
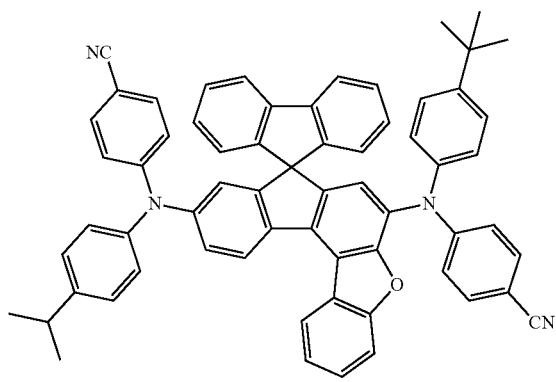
<Chemical Formula d79>
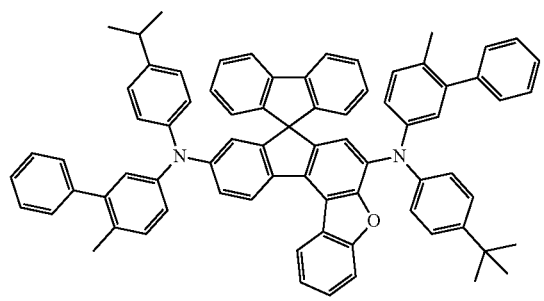
<Chemical Formula d80>
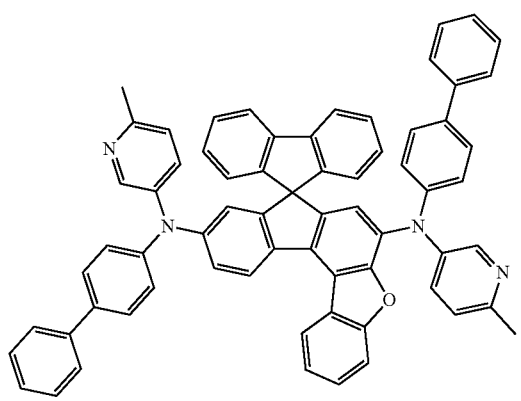
<Chemical Formula d81>
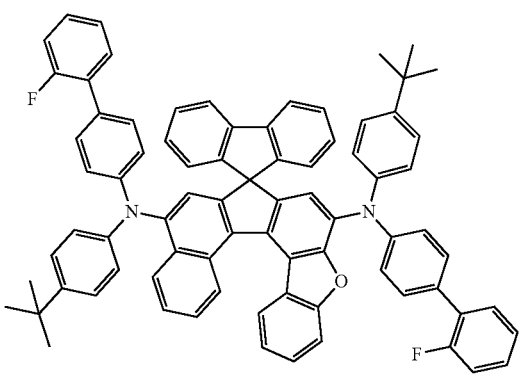
<Chemical Formula d82>
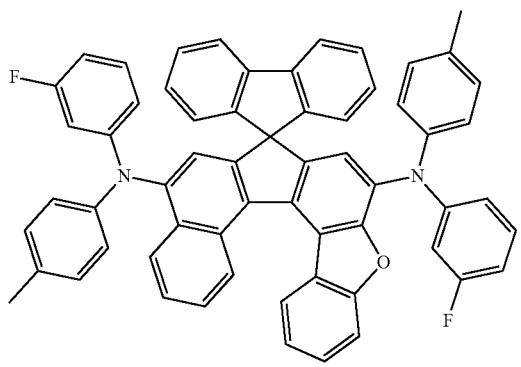
<Chemical Formula d83>
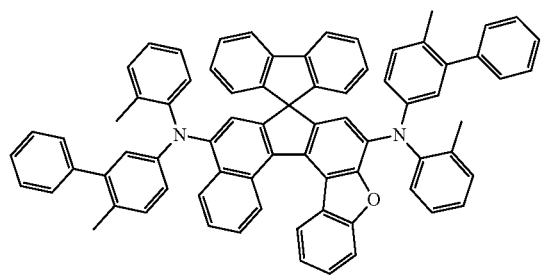
<Chemical Formula d84>
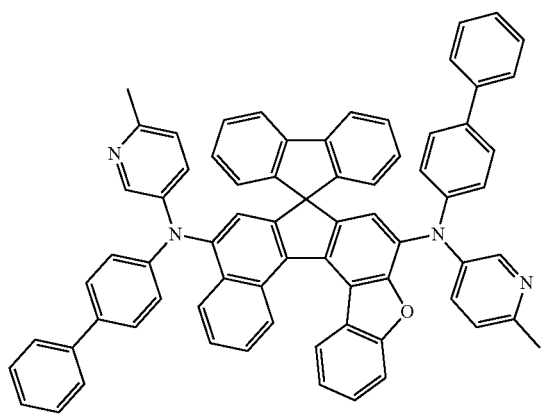
<Chemical Formula d85>
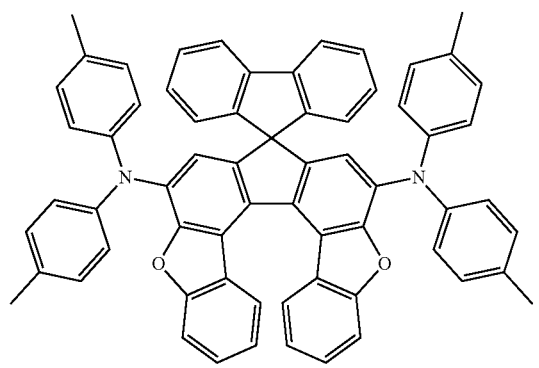

<Chemical Formula d86>
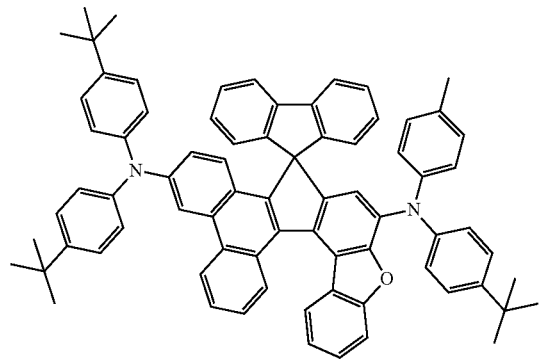
<Chemical Formula d87>
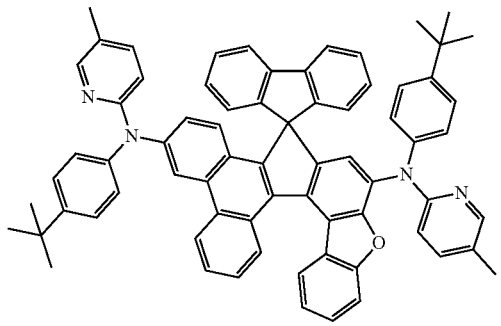
<Chemical Formula d88>
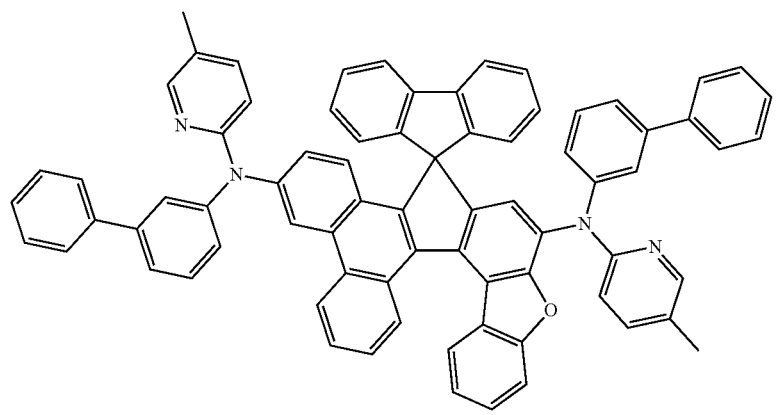
<Chemical Formula d89>
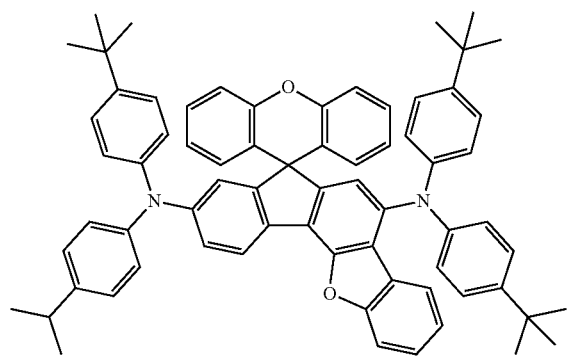
<Chemical Formula d90>
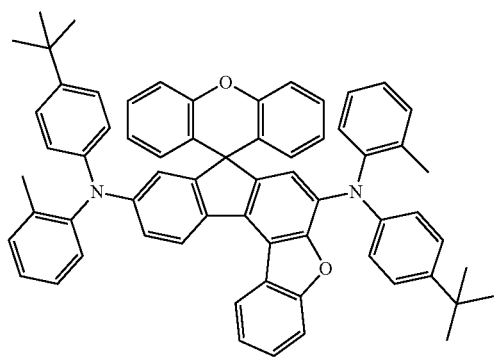
<Chemical Formula d91>
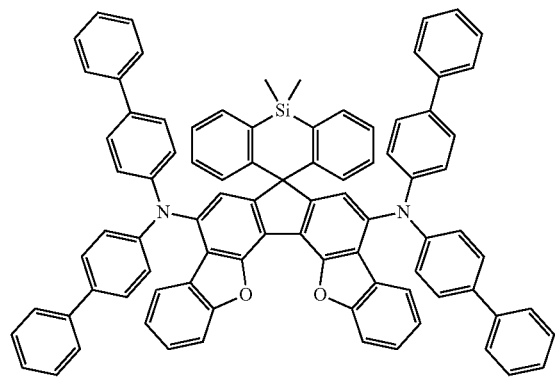
<Chemical Formula d92>
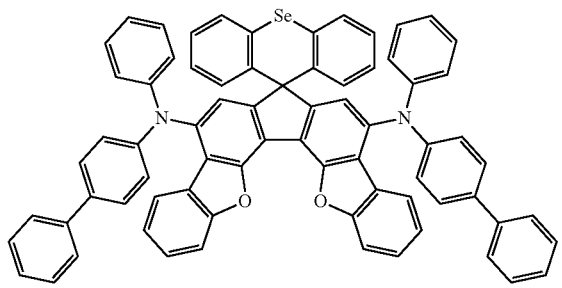

<Chemical Formula d93>
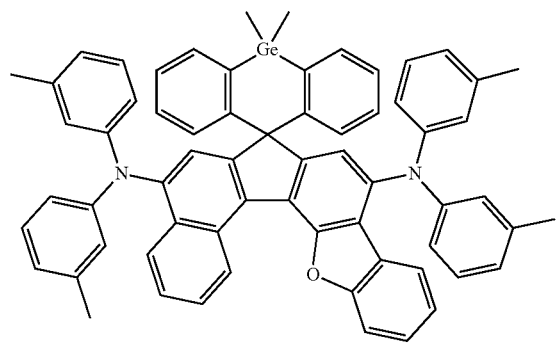
<Chemical Formula d94>
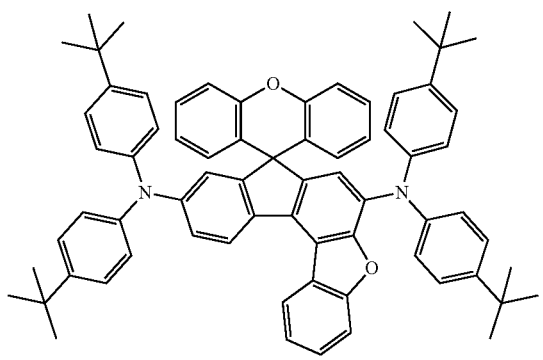
<Chemical Formula d95>
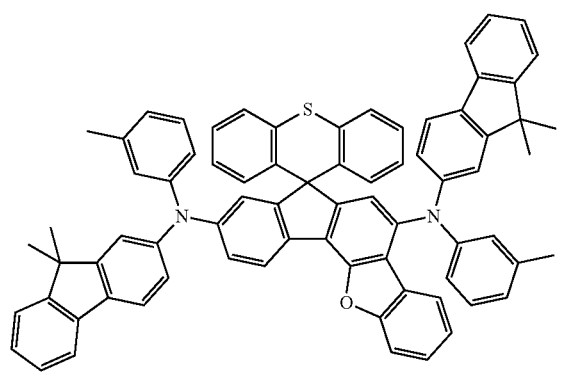
<Chemical Formula d96>
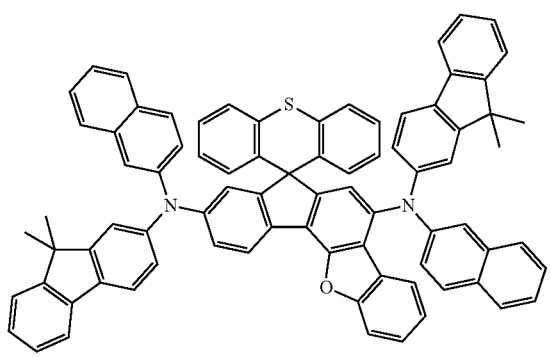
<Chemical Formula d97>
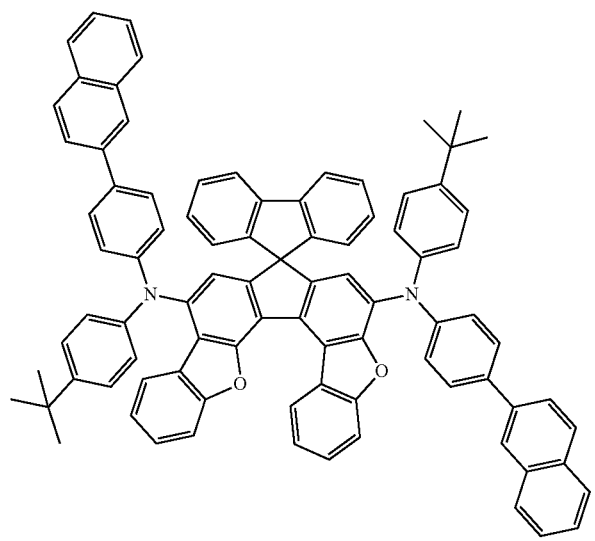
<Chemical Formula d98>
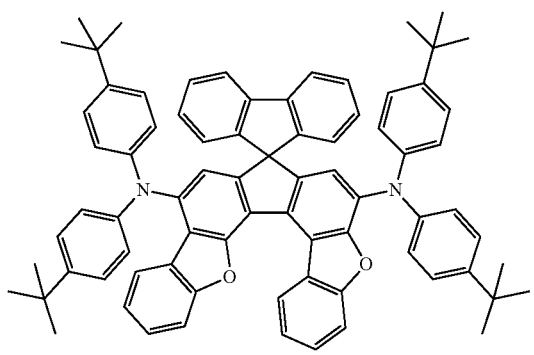

<Chemical Formula d99>
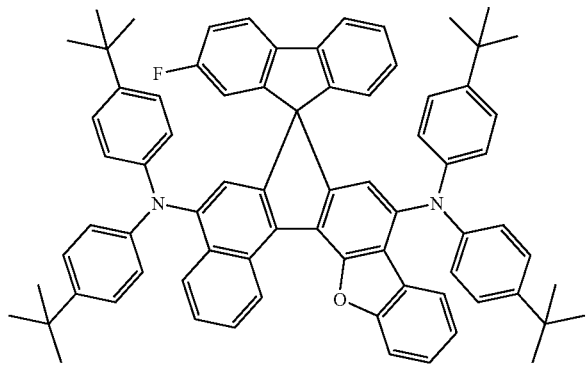
<Chemical Formula d100>
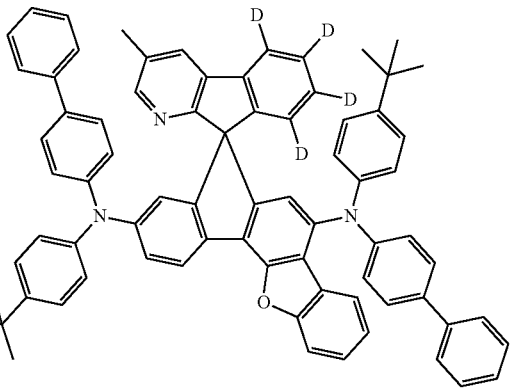
<Chemical Formula d101>
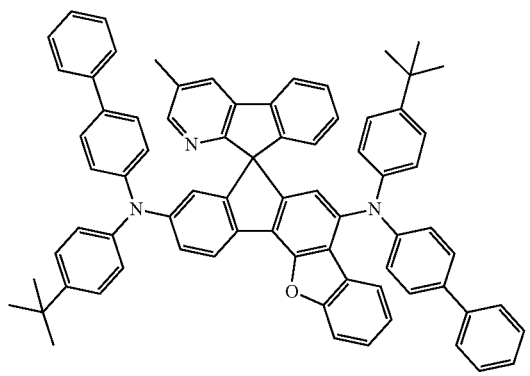
<Chemical Formula d102>
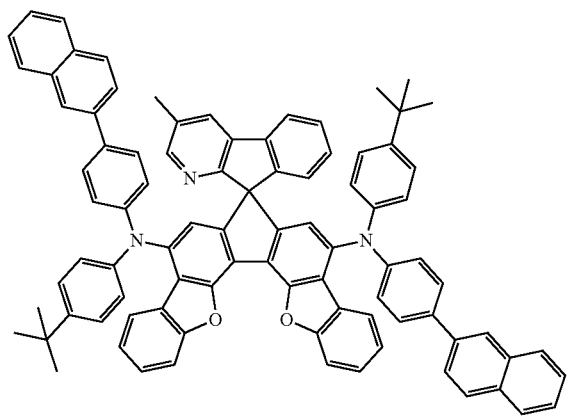
<Chemical Formula d103>
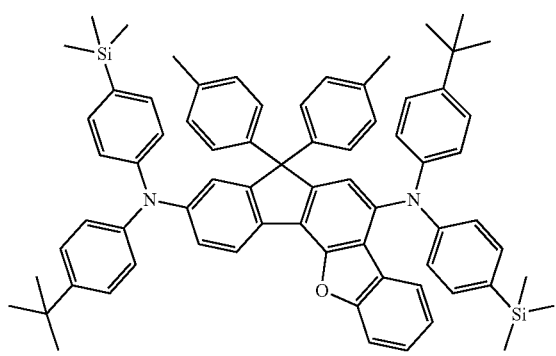
<Chemical Formula d104>
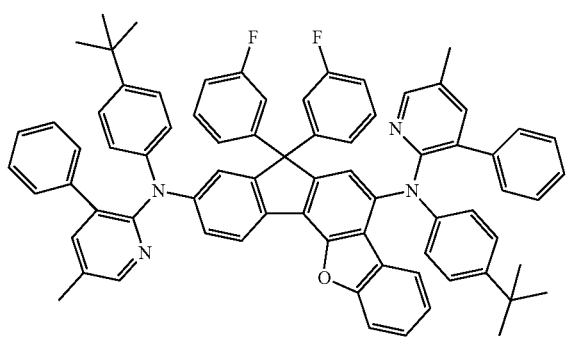
<Chemical Formula d105>
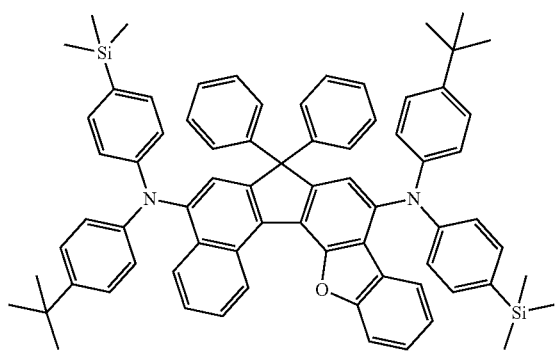
<Chemical Formula d106>
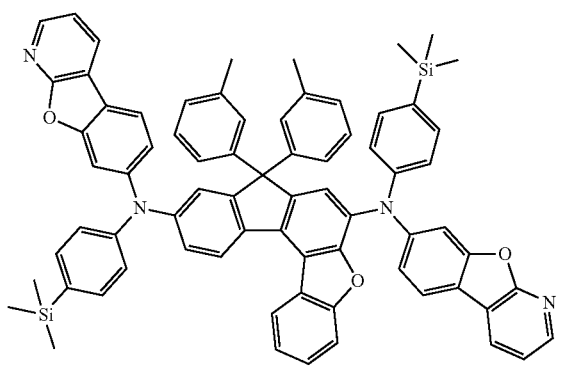

<Chemical Formula d107>
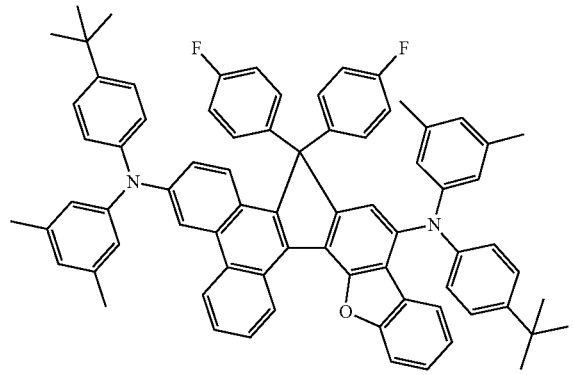
<Chemical Formula d108>
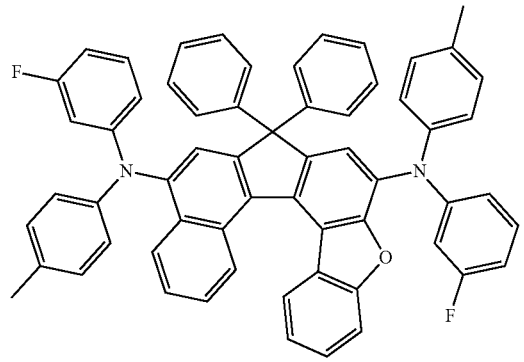
<Chemical Formula d109>
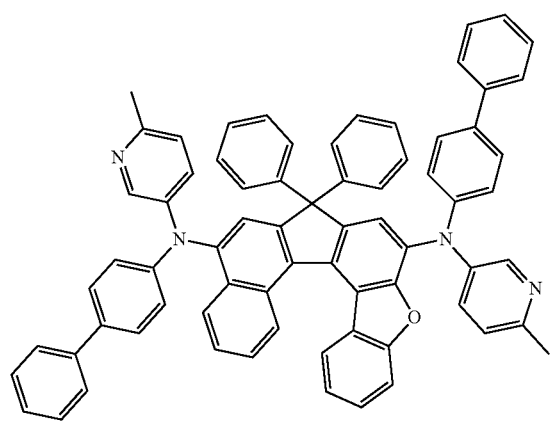
<Chemical Formula d110>
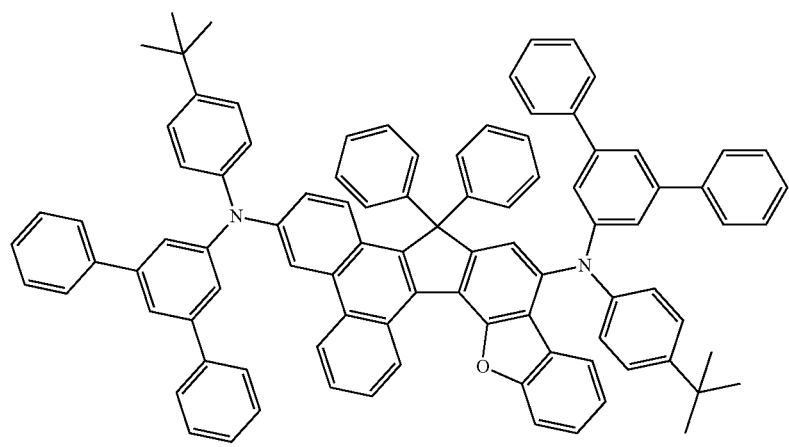

-continued
<Chemical Formula d111>
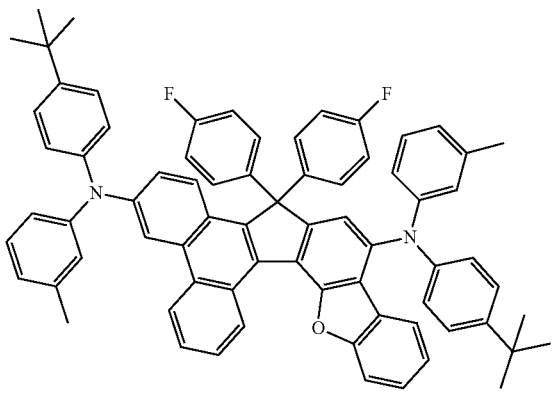
<Chemical Formula d112>
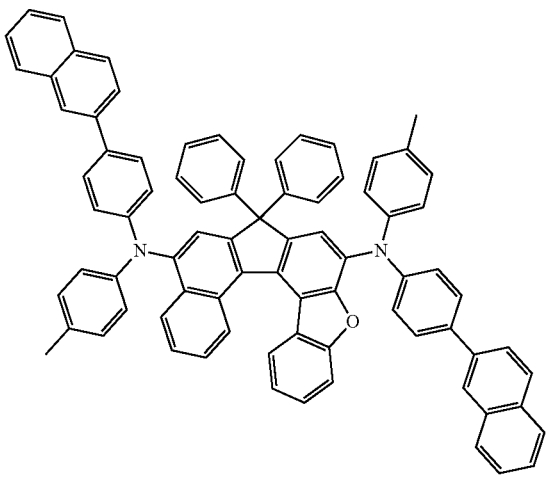
<Chemical Formula d113>
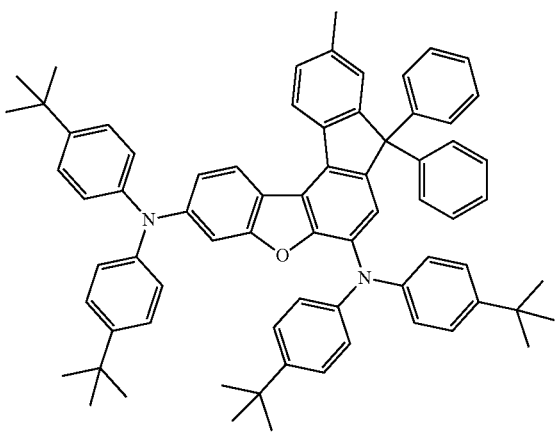
<Chemical Formula d114>
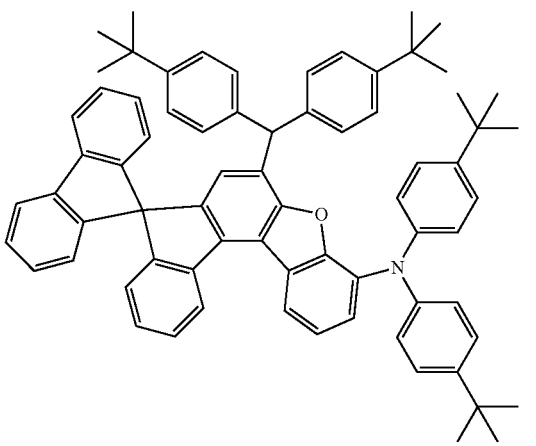
<Chemical Formula d115>
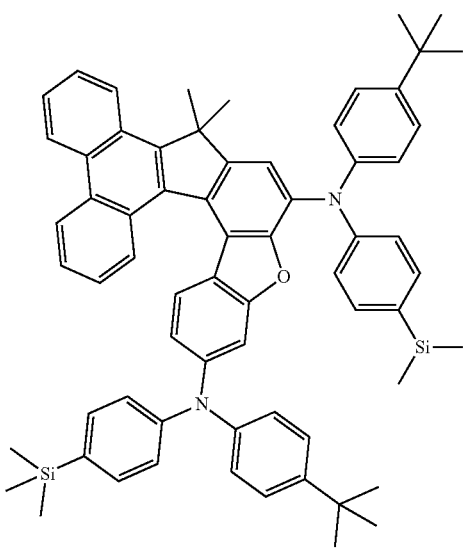
<Chemical Formula d116>
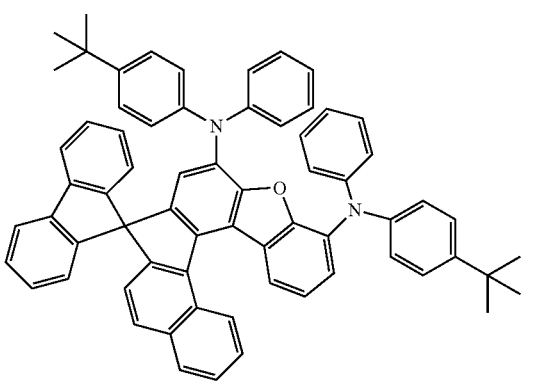

-continued
<Chemical Formula d117>
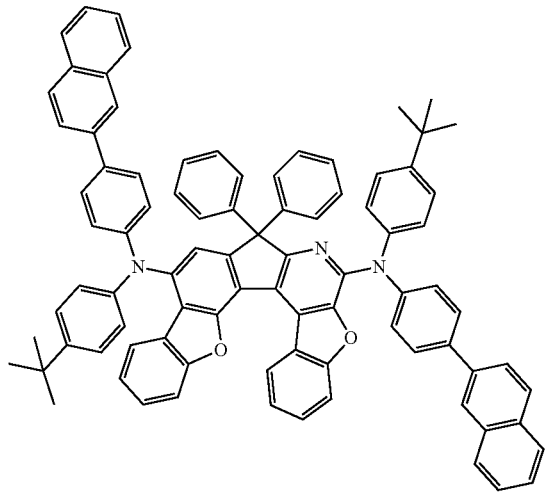
<Chemical Formula d118>
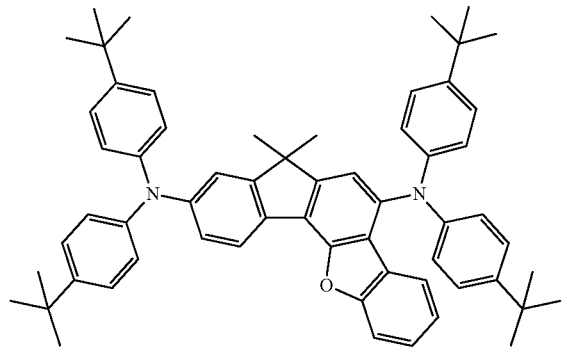
<Chemical Formula d119>
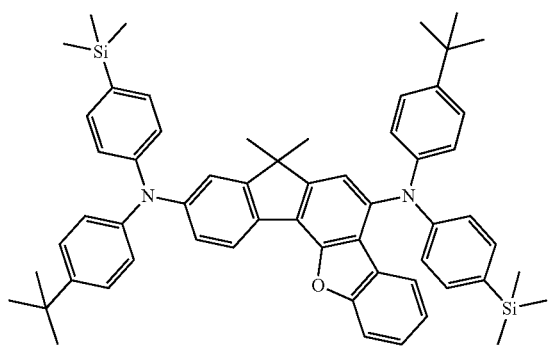
<Chemical Formula d120>
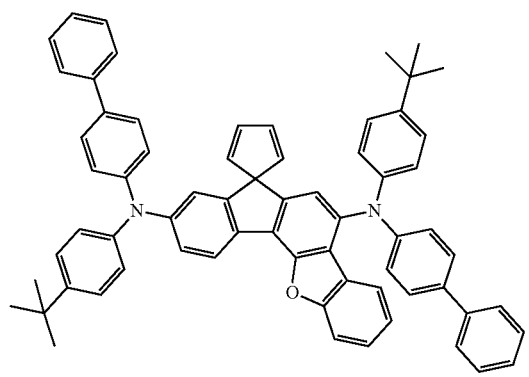
<Chemical Formula d121>
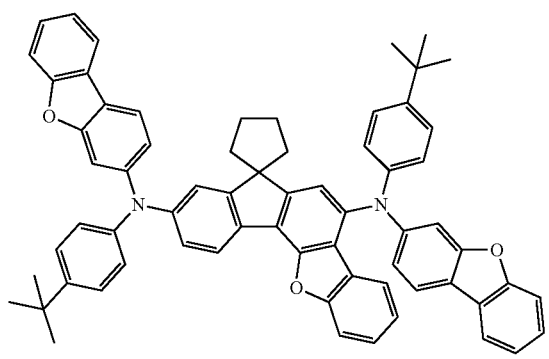
<Chemical Formula d122>
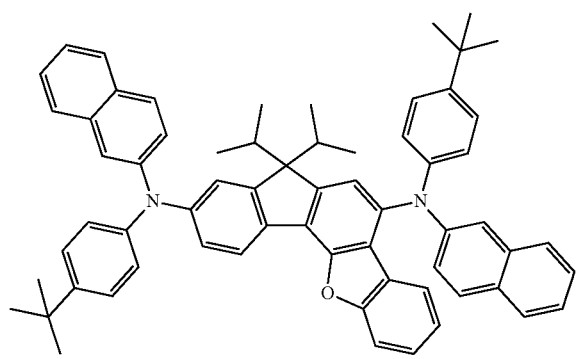
<Chemical Formula d123>
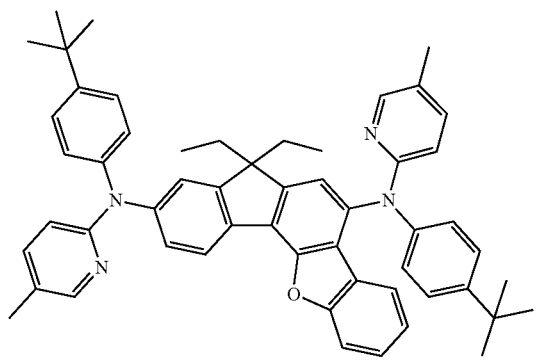
<Chemical Formula d124>
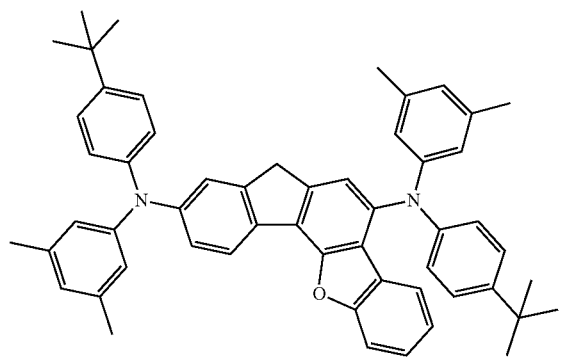

<Chemical Formula d125>
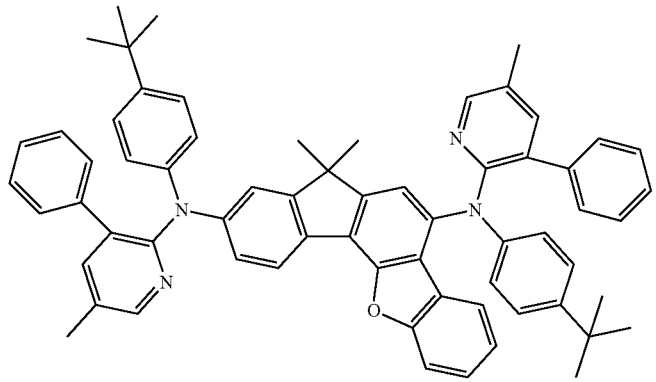
<Chemical Formula d126>
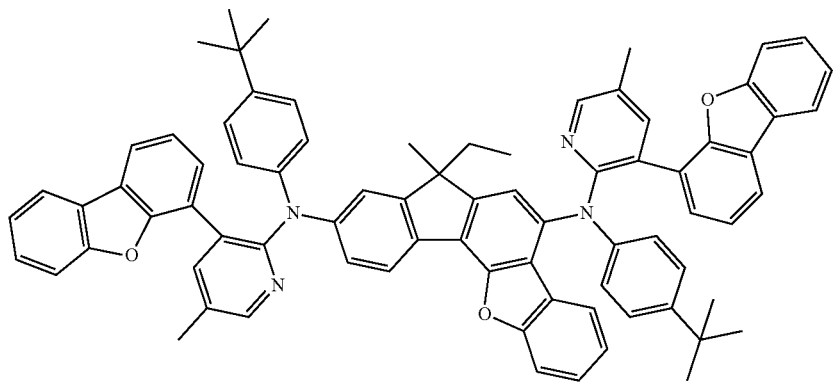
<Chemical Formula d127>
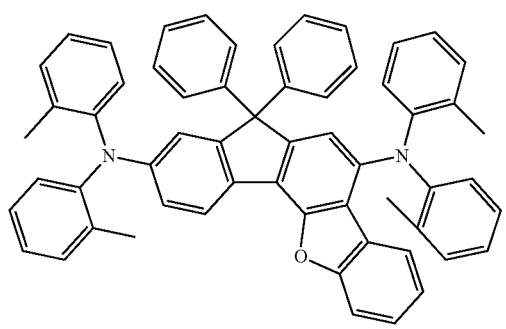
<Chemical Formula d128>
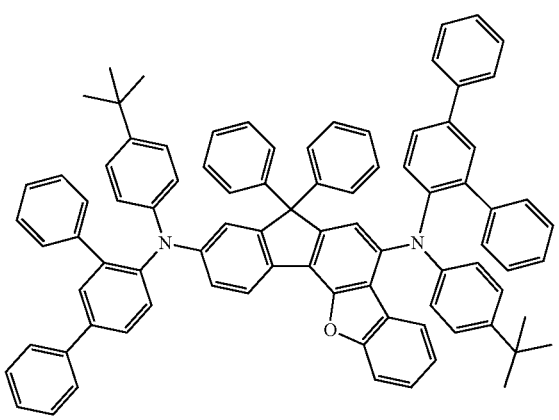
<Chemical Formula d129>
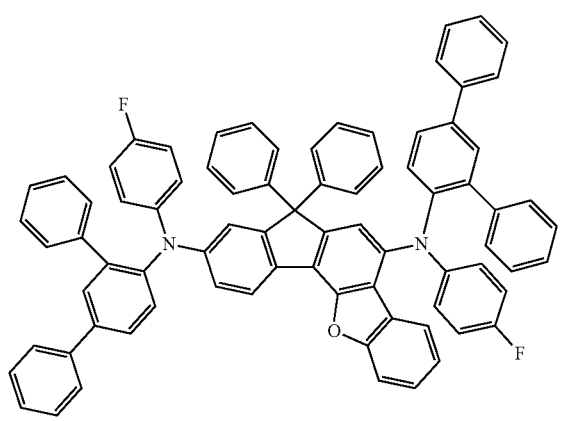
<Chemical Formula d130>
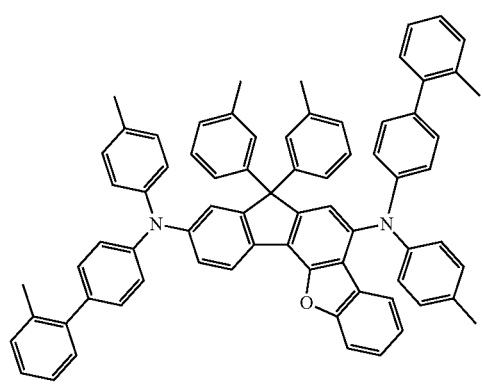

<Chemical Formula d131>
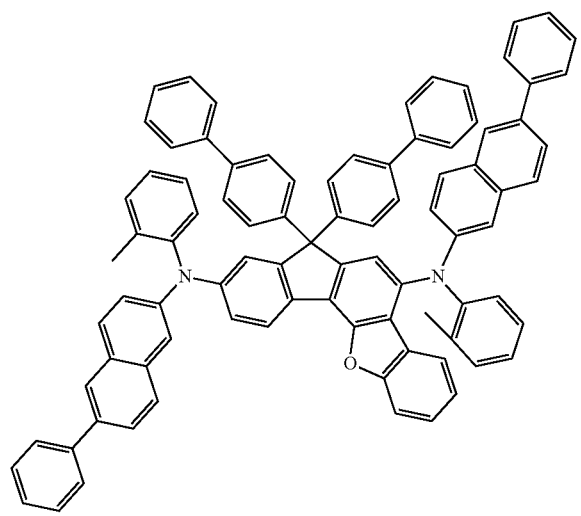
<Chemical Formula d132>
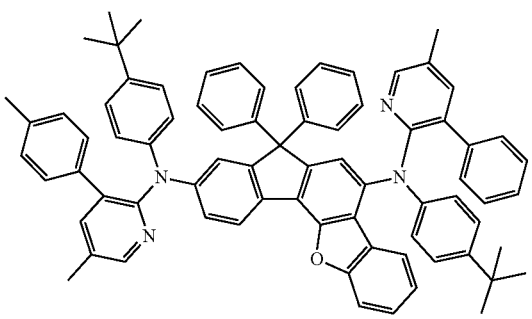
<Chemical Formula d133>
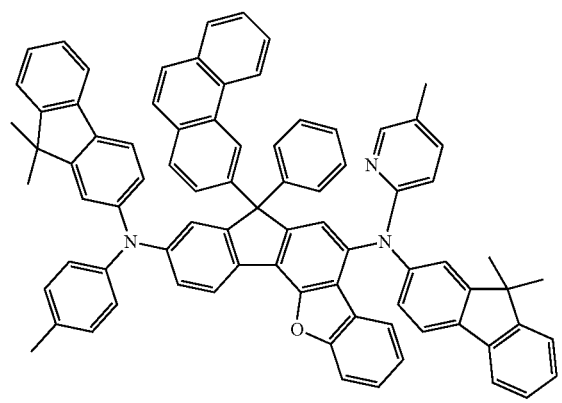
<Chemical Formula d134>
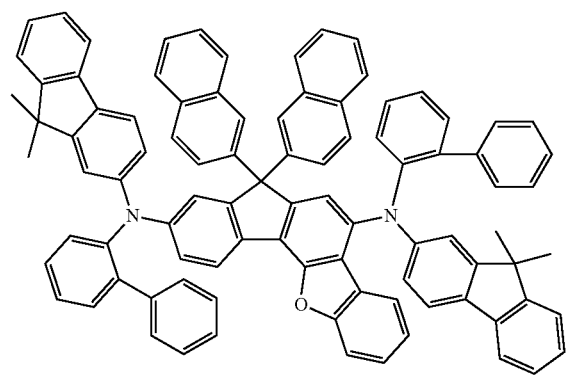
<Chemical Formula d135>
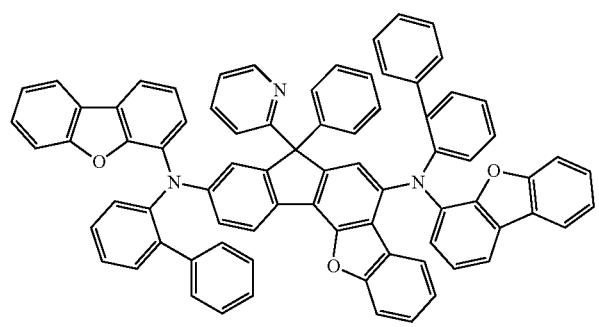
<Chemical Formula d136>
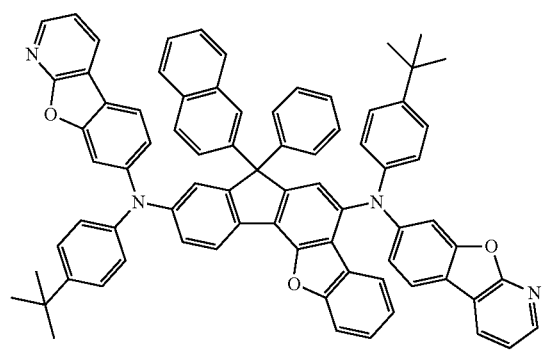

<Chemical Formula d137>
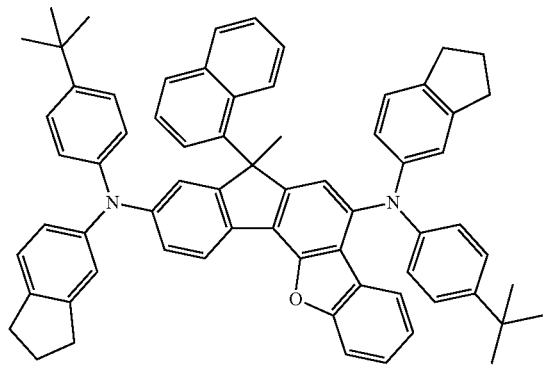
<Chemical Formula d138>
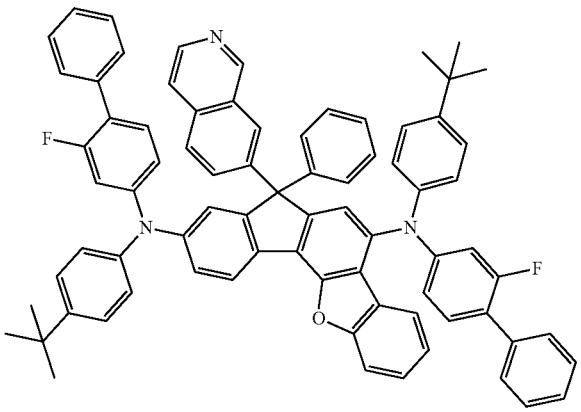
<Chemical Formula d139>
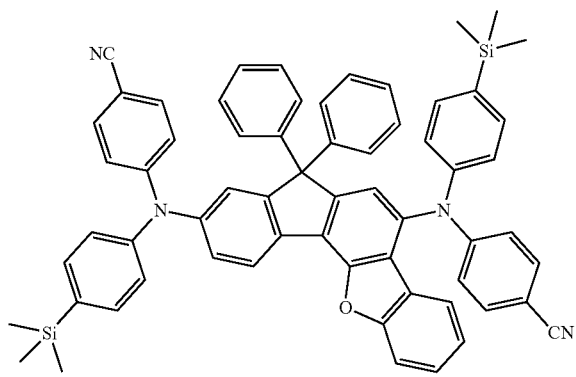
<Chemical Formula d140>
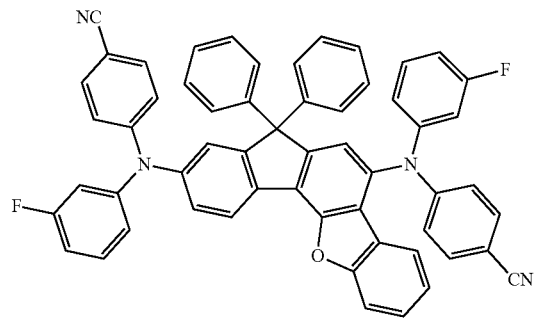
<Chemical Formula d141>
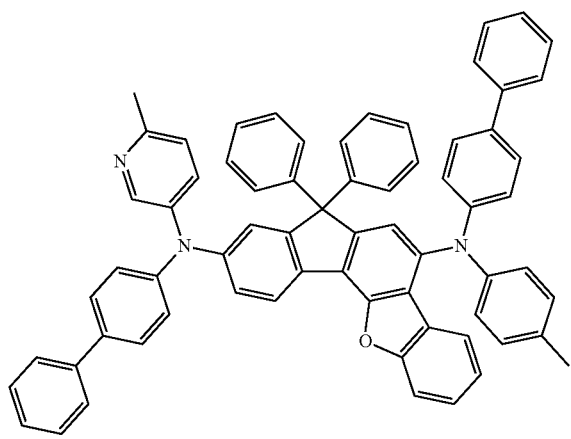
<Chemical Formula d142>
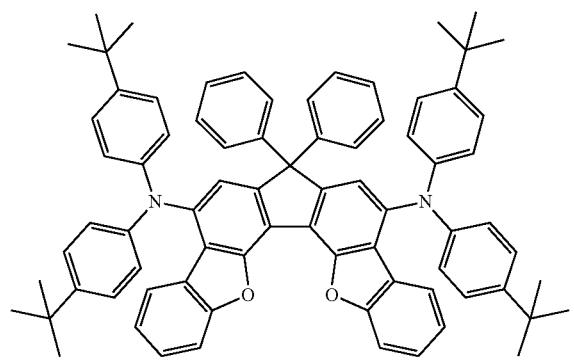

<Chemical Formula d143>
<Chemical Formula d144>
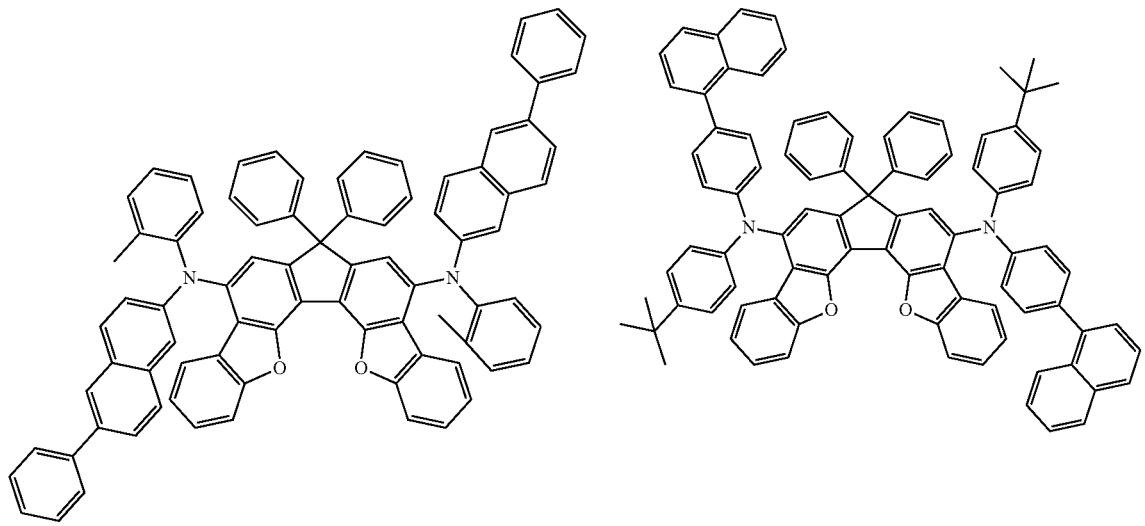
<Chemical Formula d145>
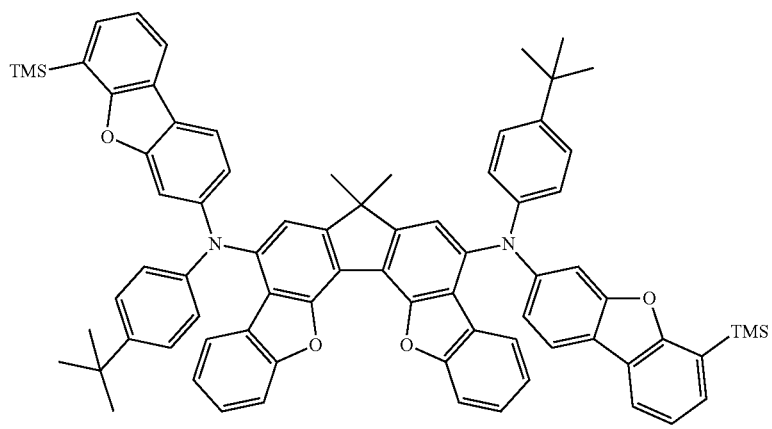
<Chemical Formula d146>
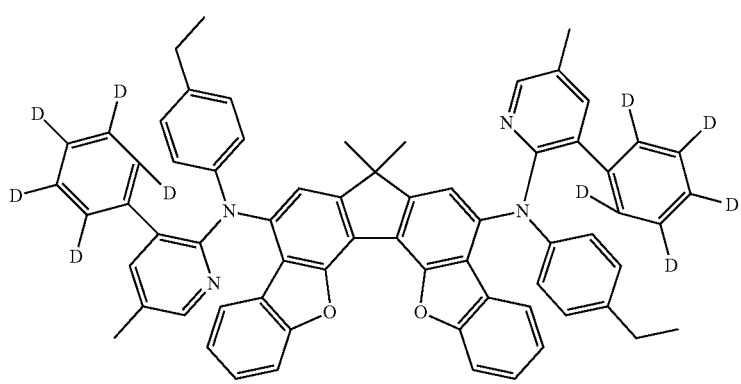

-continued
<Chemical Formula d147>
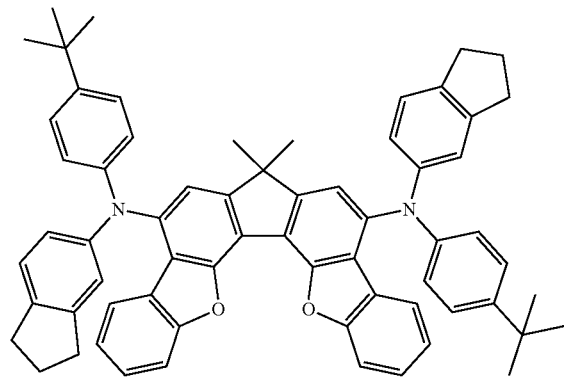
<Chemical Formula d148>
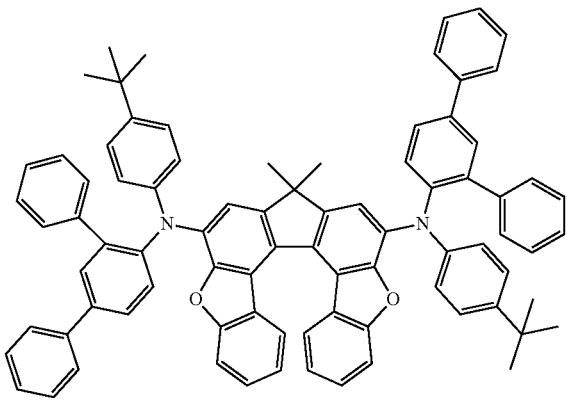
<Chemical Formula d149>
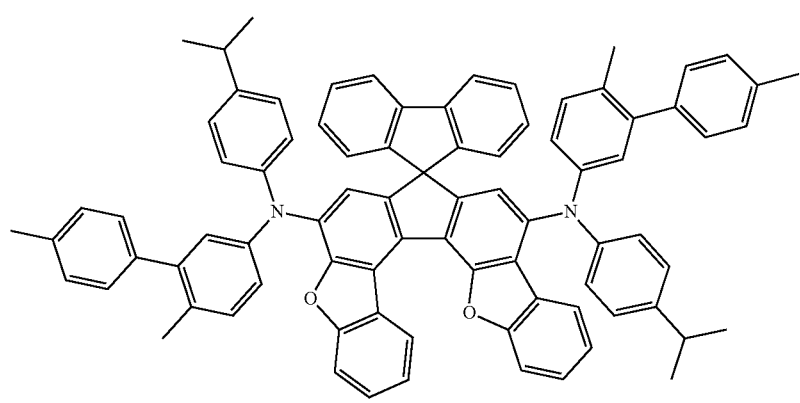
<Chemical Formula d150>
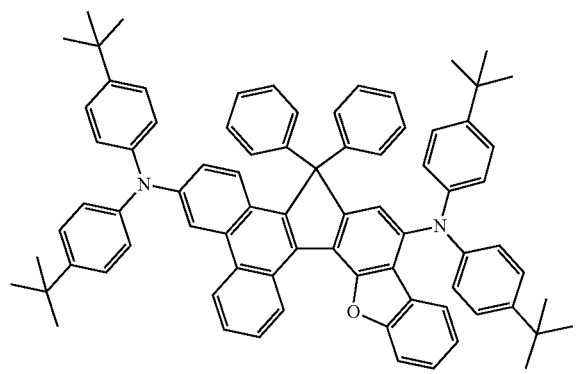
<Chemical Formula d151>
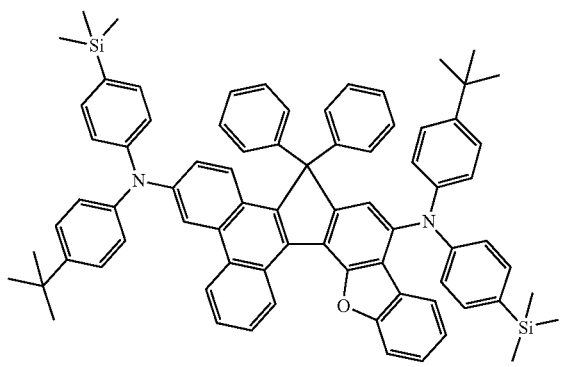

-continued
<Chemical Formula d152>
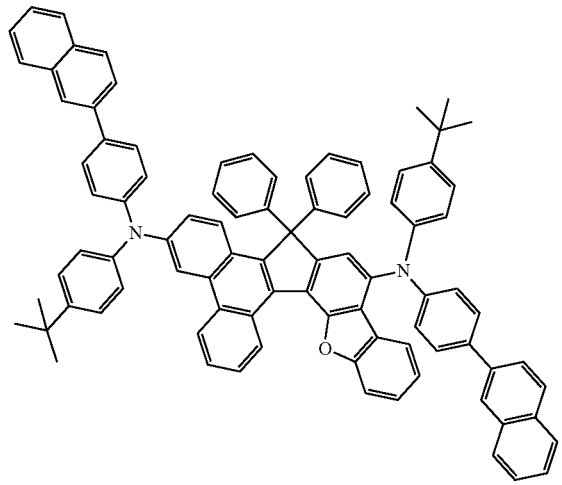
<Chemical Formula d153>
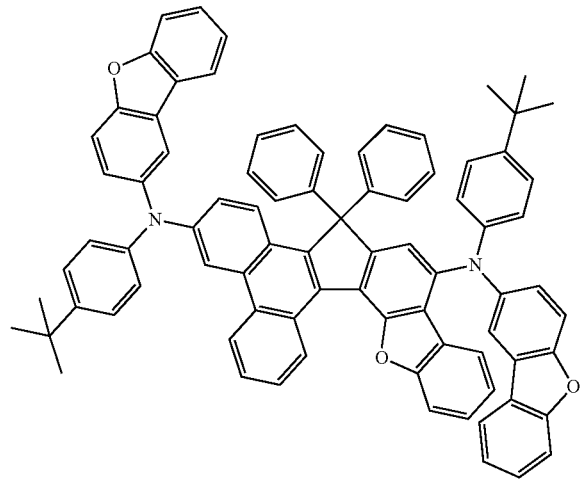
<Chemical Formula d154>
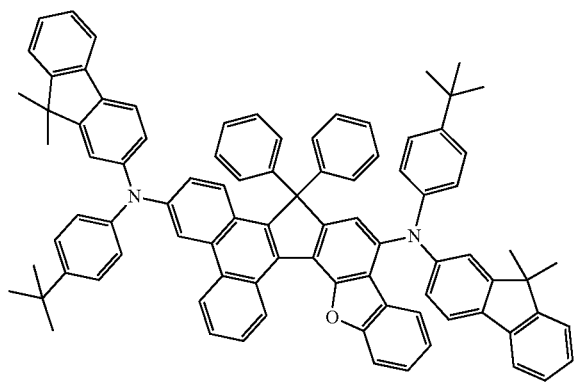
<Chemical Formula d155>
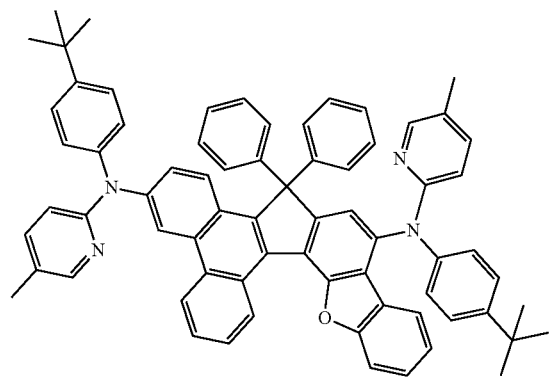
<Chemical Formula d156>
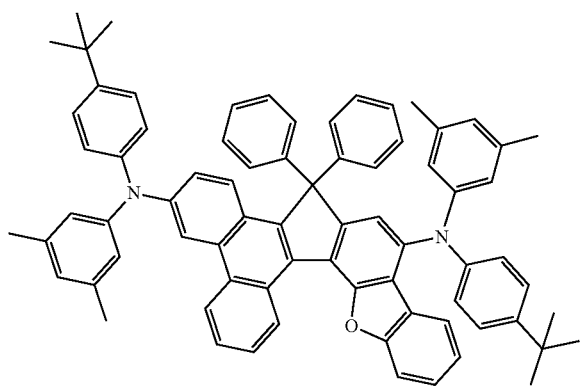
<Chemical Formula d157>
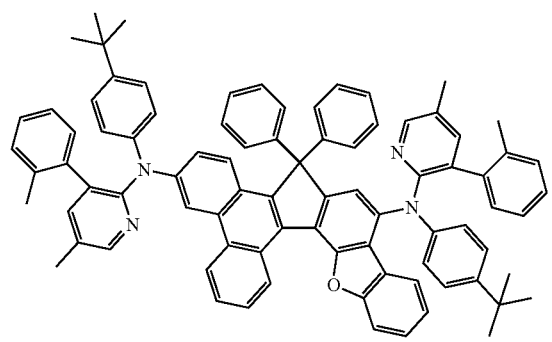

-continued
<Chemcial Formula d158>
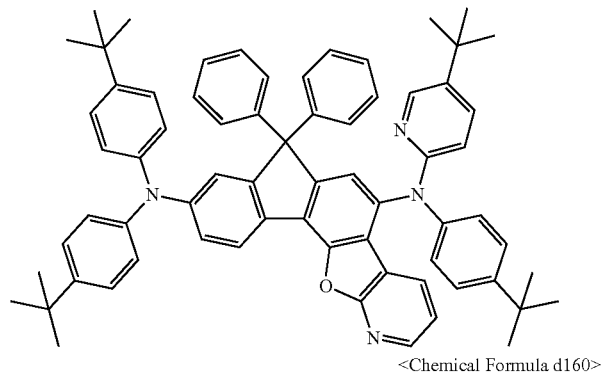
<Chemcial Formula d159>
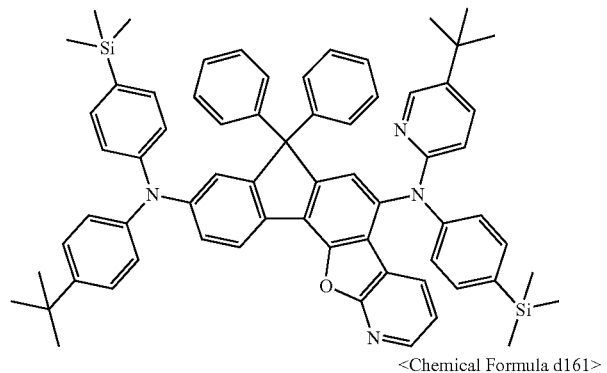
<Chemical Formula d160>
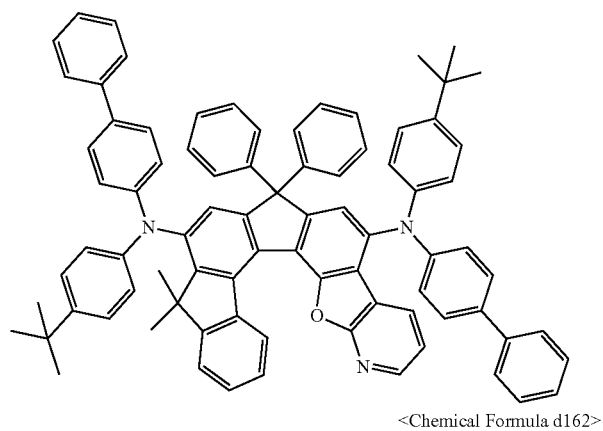
<Chemical Formula d161>
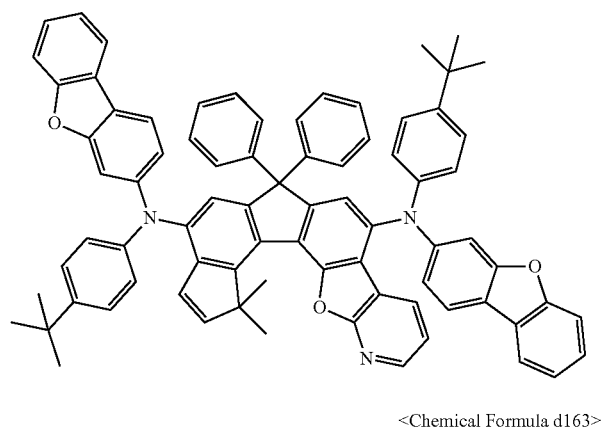
<Chemical Formula d162>
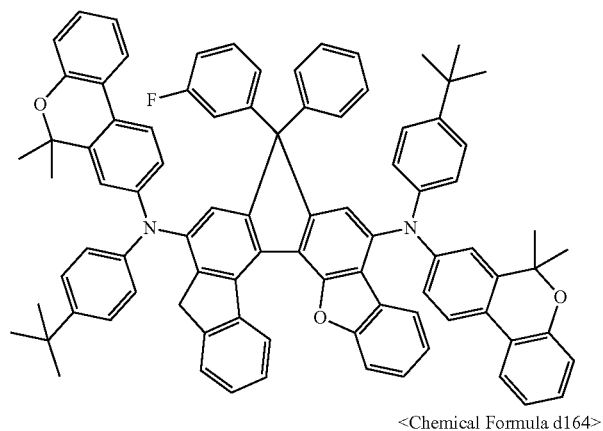
<Chemical Formula d163>
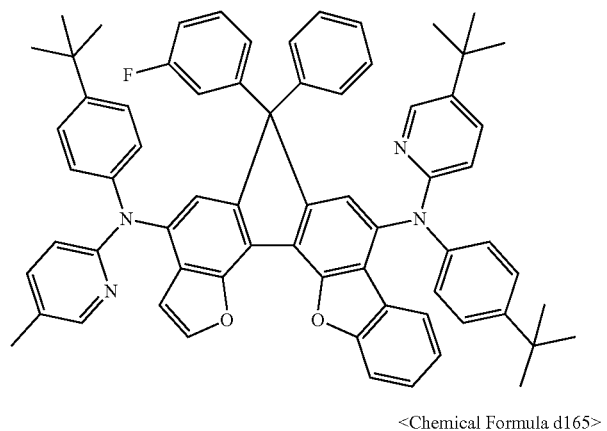
<Chemical Formula d164>
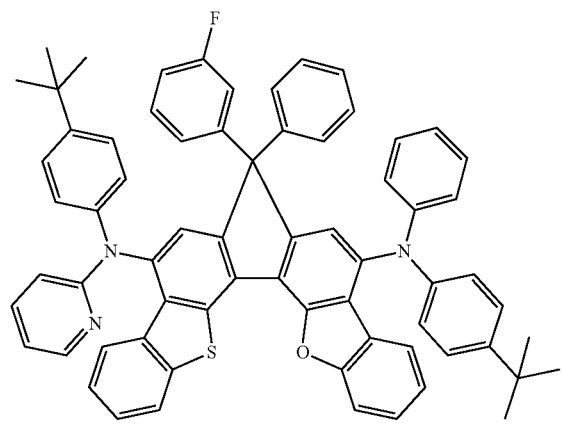
<Chemical Formula d165>
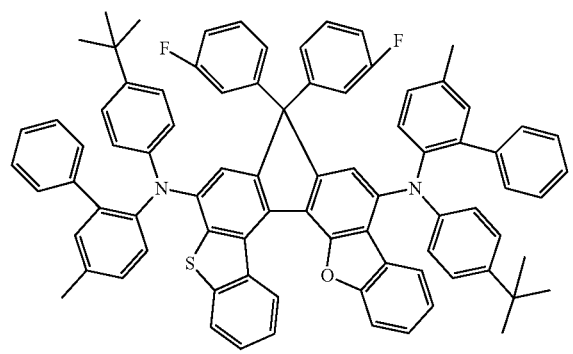

-continued
<Chemical Formula d166>
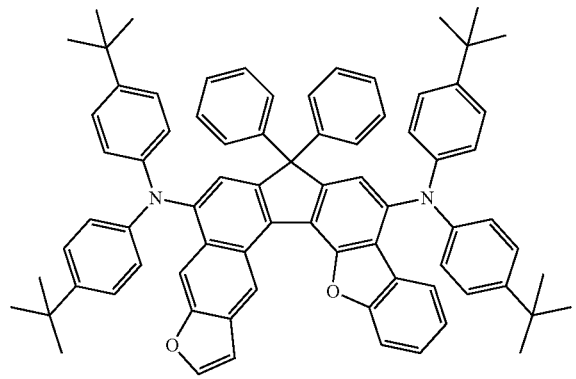
<Chemical Formula d167>
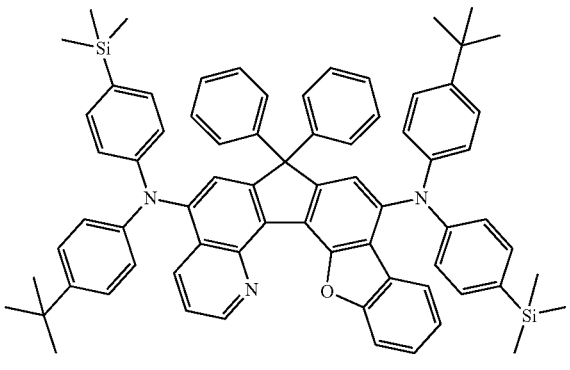
<Chemical Formula d168>
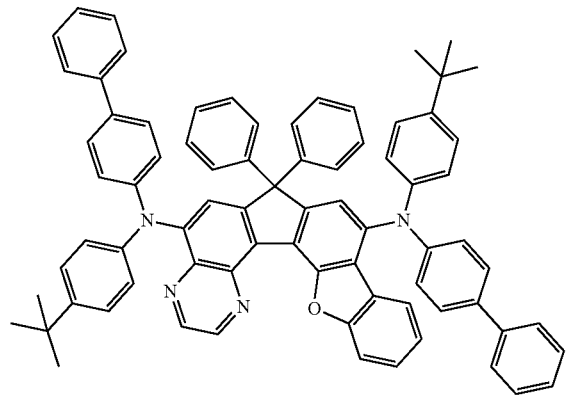
<Chemical Formula d169>
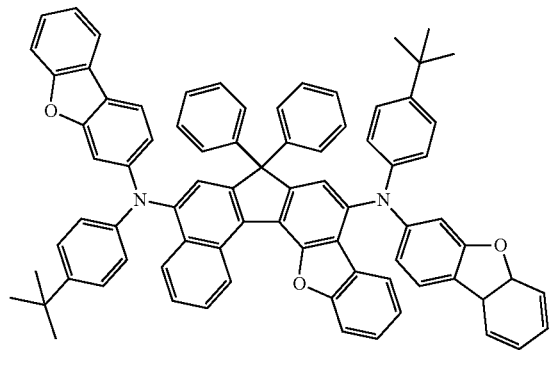
<Chemical Formula d170>
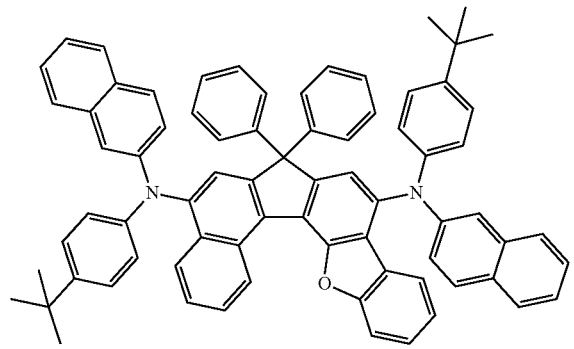
<Chemical Formula d171>
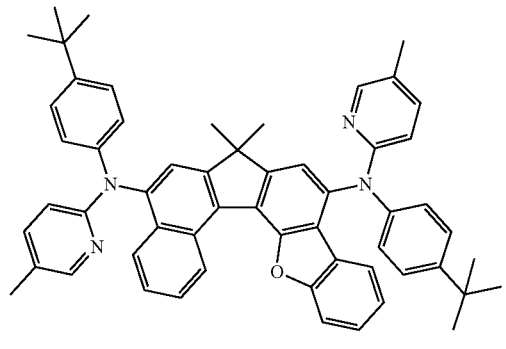
<Chemical Formula d172>
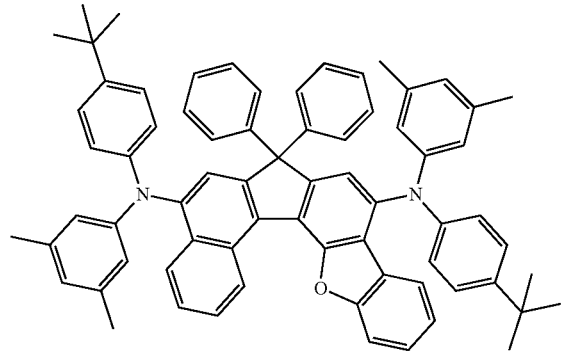
<Chemical Formula d173>
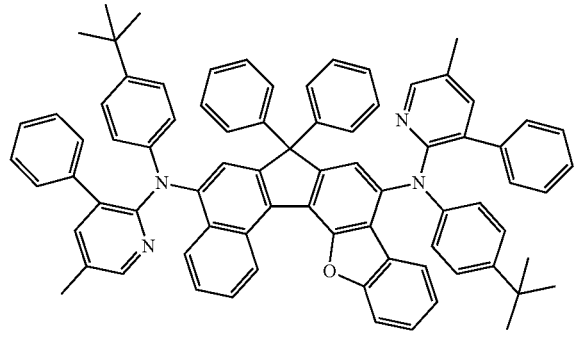

<Chemical Formula d174>
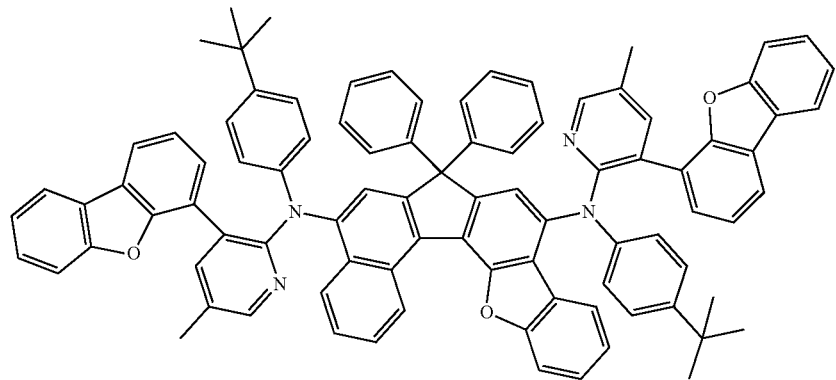
<Chemical Formula d175>
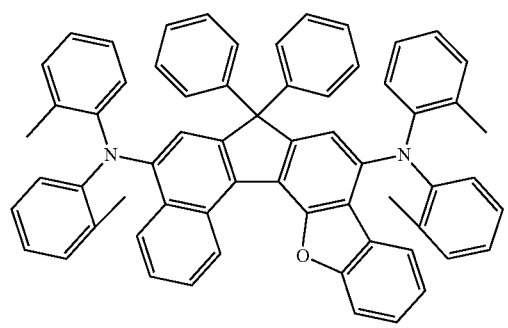
<Chemical Formula d176>
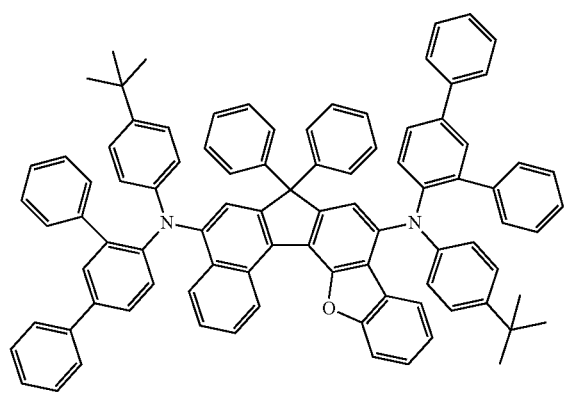
<Chemical Formula d177>
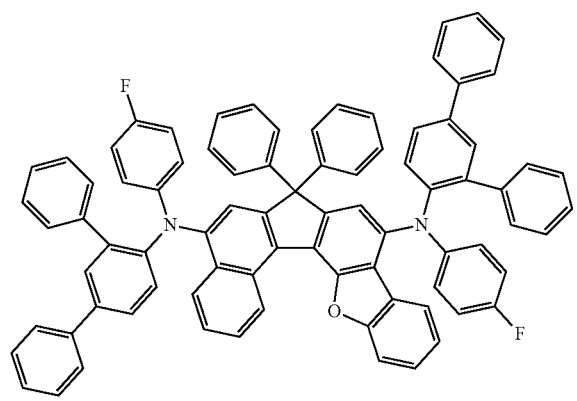
<Chemical Formula d178>
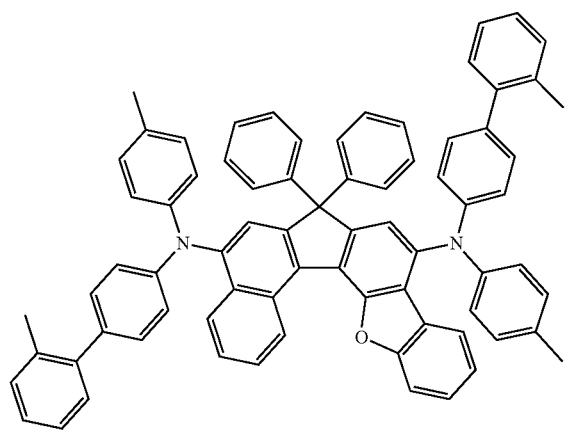
<Chemical Formula d179>
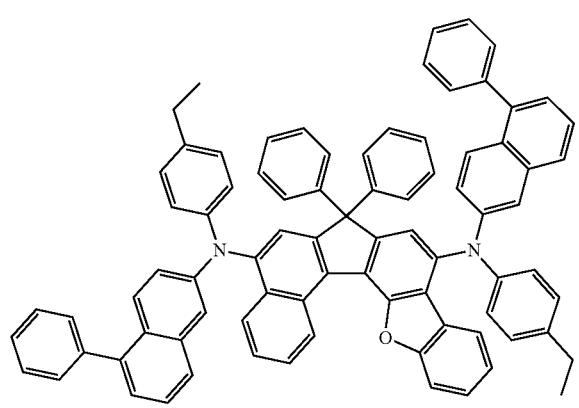
<Chemical Formula d180>
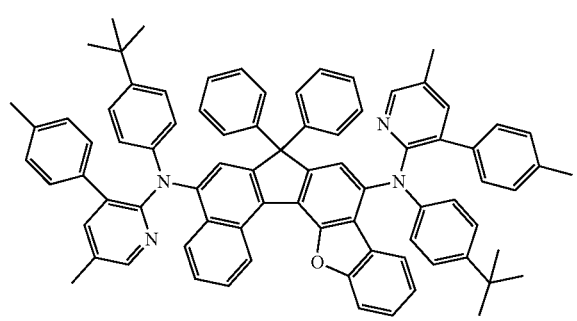

<Chemical Formula d181>
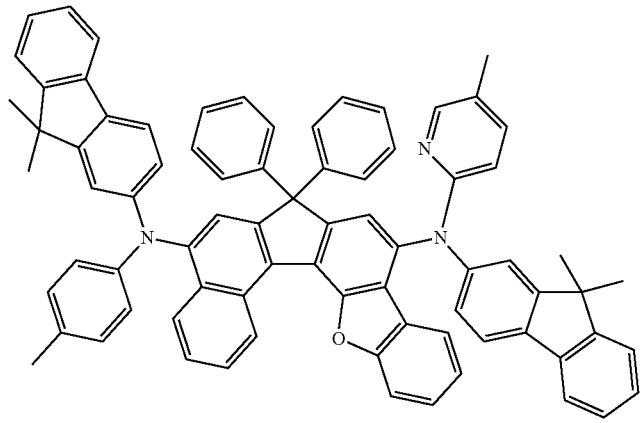
<Chemical Formula d182>
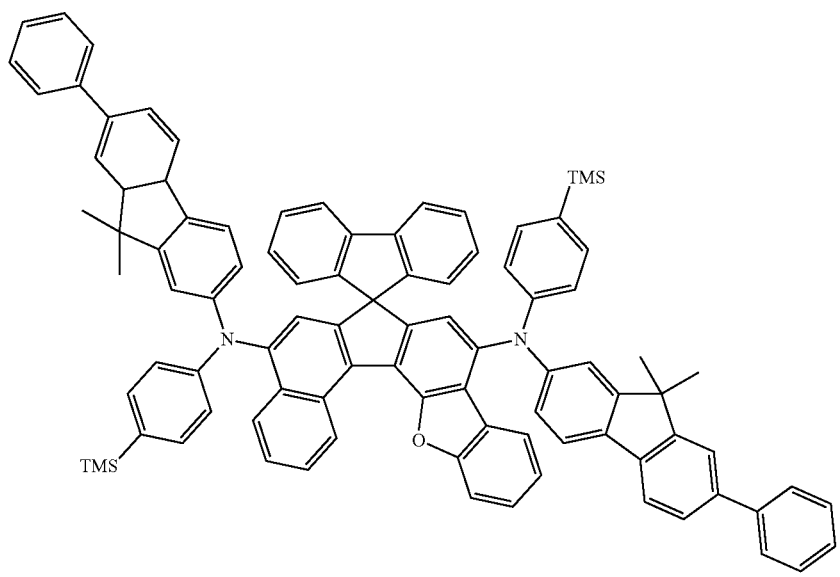
<Chemical Formula d183>
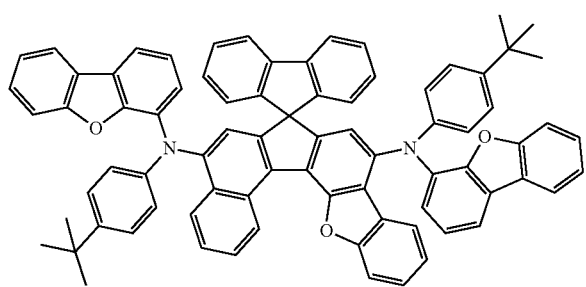
<Chemical Formula d184>
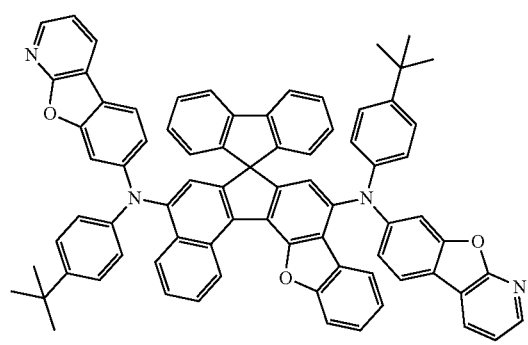

<Chemical Formula d185>
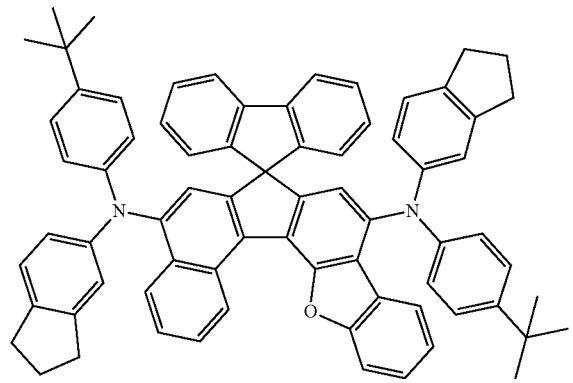
<Chemical Formula d186>
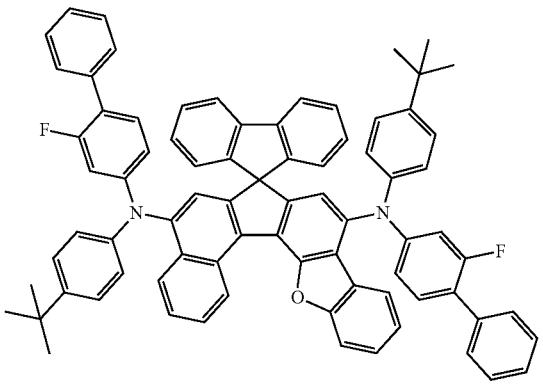
<Chemical Formula d187>
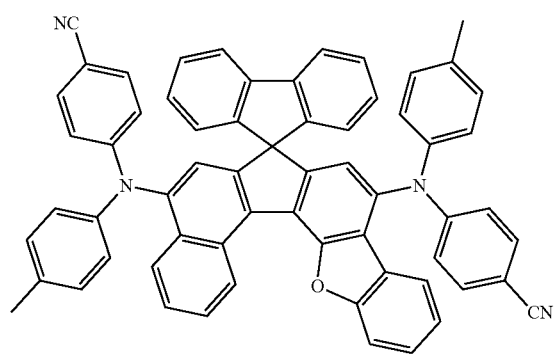
<Chemical Formula d188>
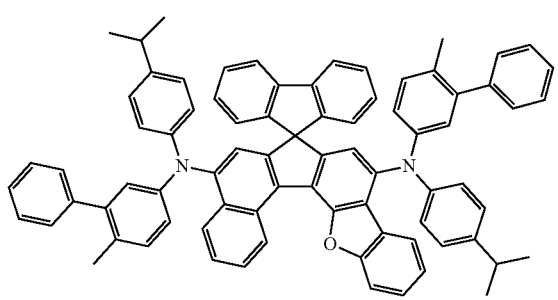
<Chemical Formula d189>
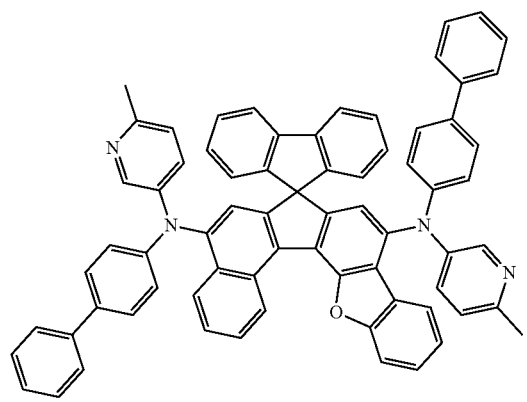
<Chemical Formula d190>
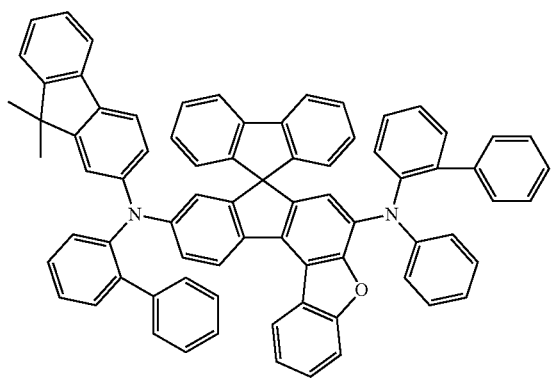
<Chemical Formula d191>
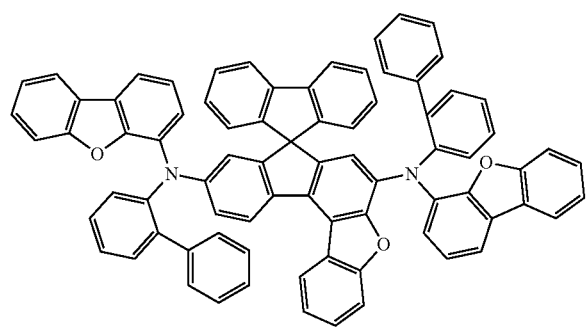
<Chemical Formula d192>
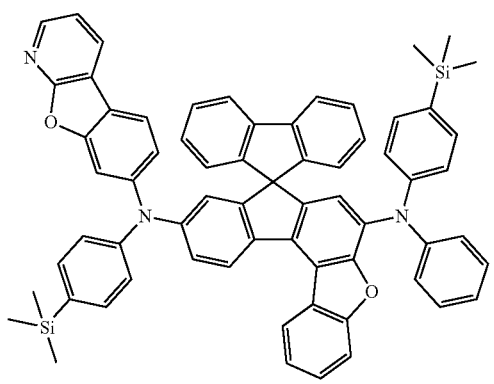

<Chemical Formula d193>
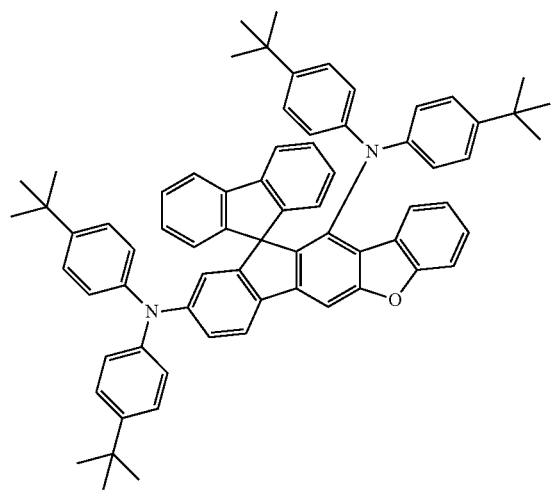
<Chemical Formula d194>
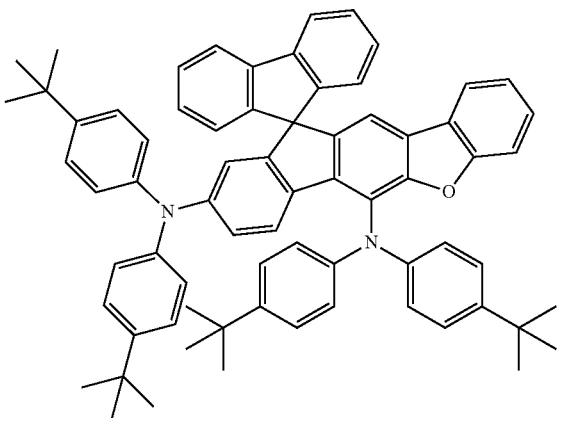
<Chemical Formula d195>
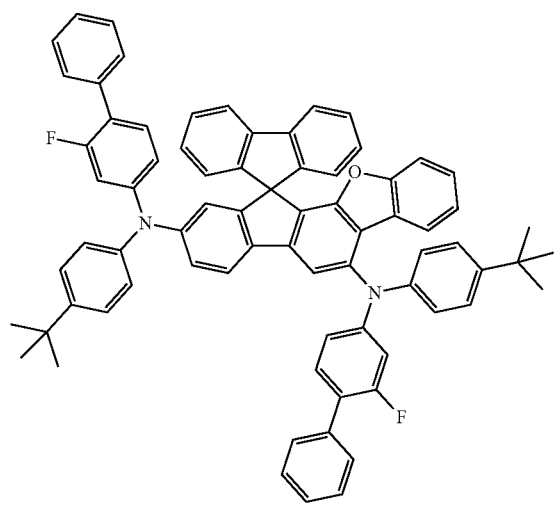
<Chemical Formula d196>
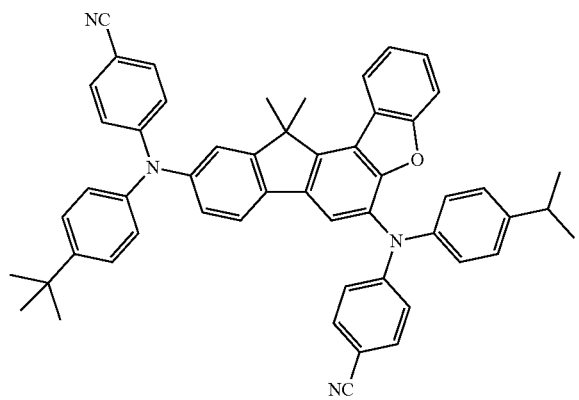

<Chemical Formula d197>
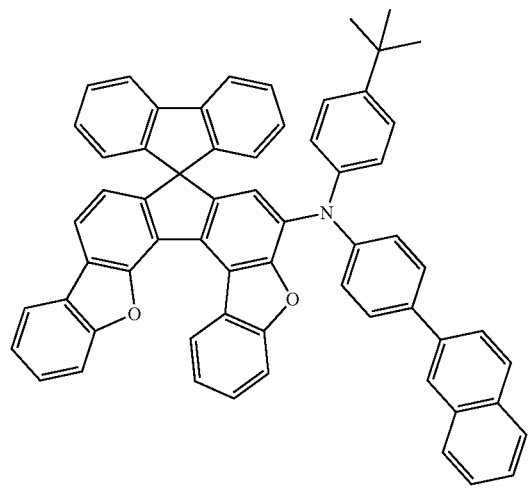
<Chemical Formula d198>
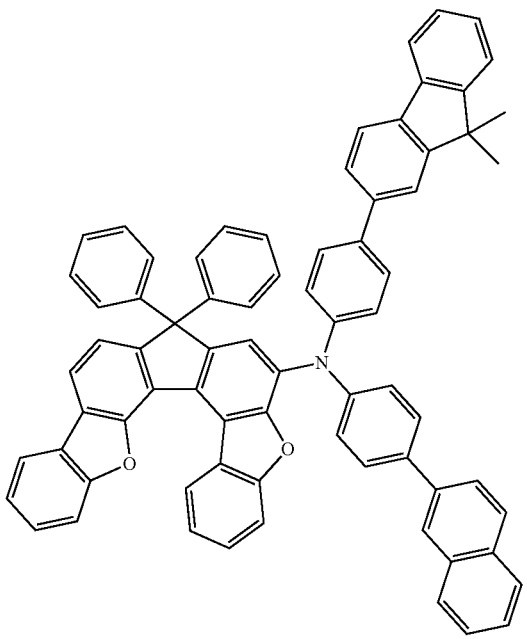
<Chemical Formula d199>
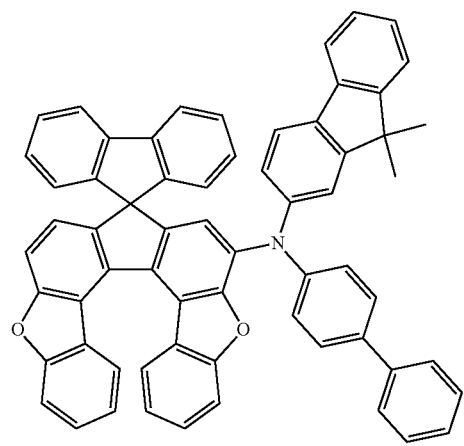
<Chemical Formula d200>
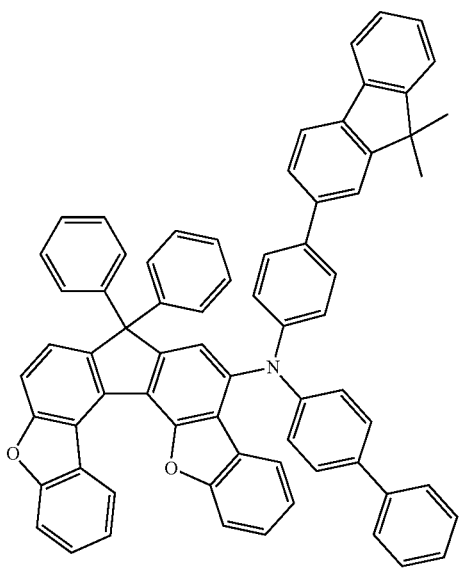

<Chemical Formula d201>
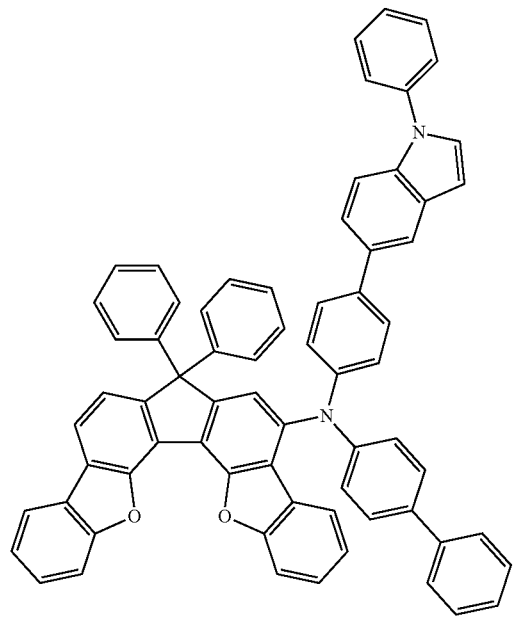
<Chemical Formula d202>
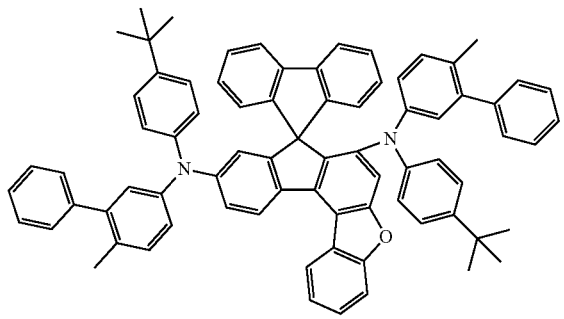
<Chemical Formula d203>
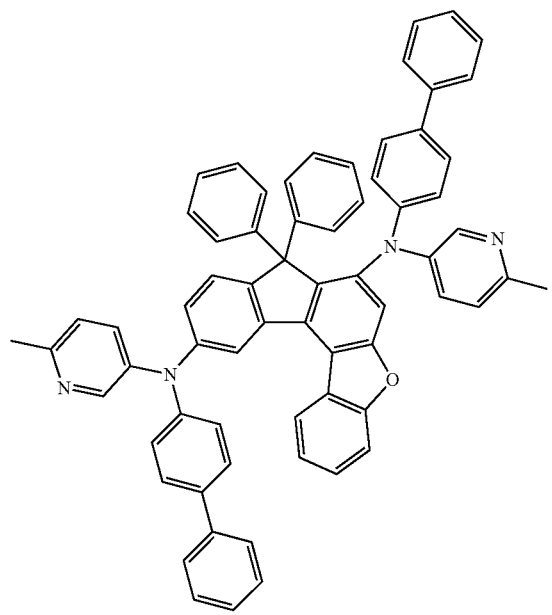
<Chemical Formula d204>
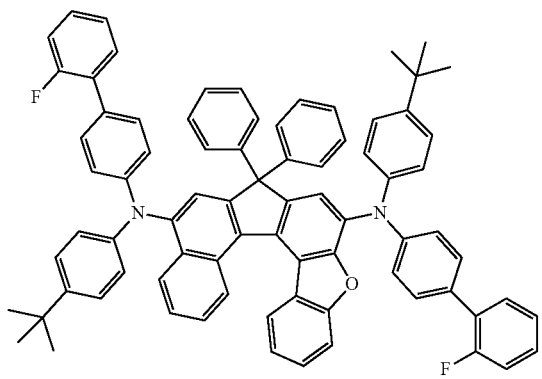
<Chemical Formula d205>
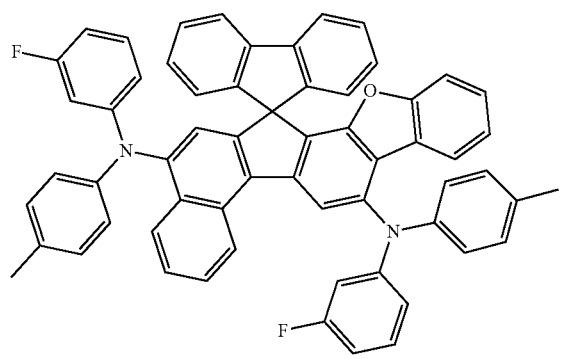
<Chemical Formula d206>
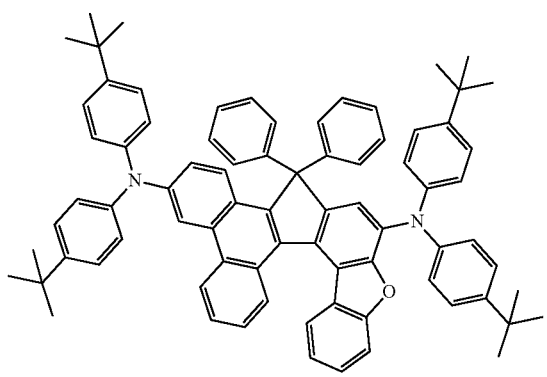

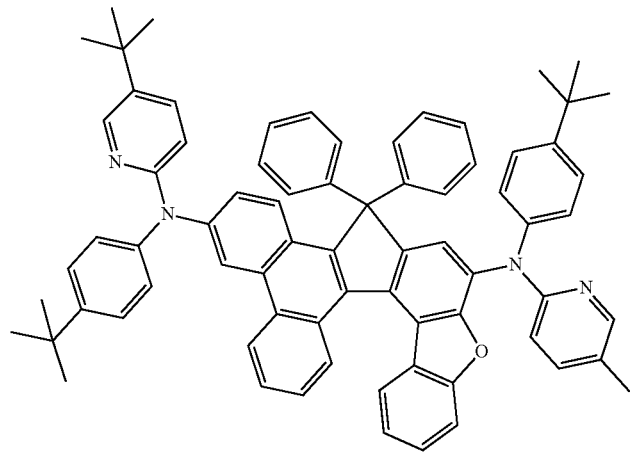
<Chemical Formula d207>
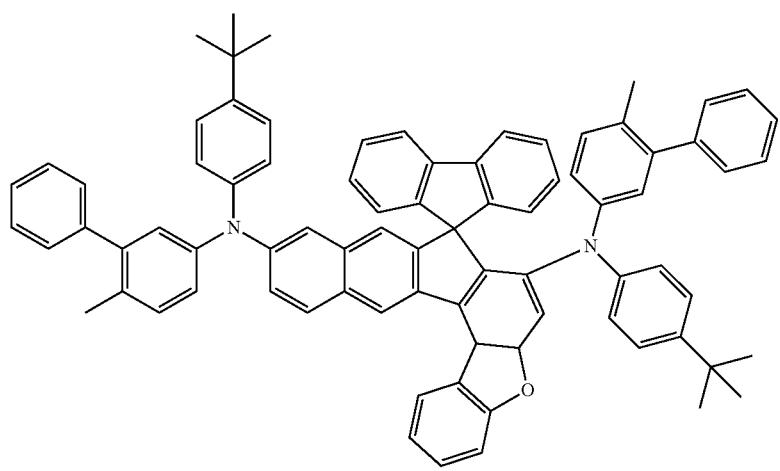
<Chemical Formula d208>
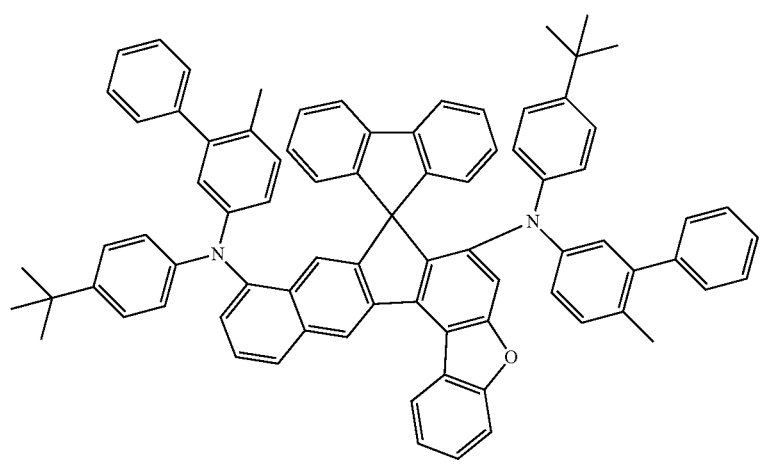
<Chemical Formula d209>

<Chemical Formula d210>
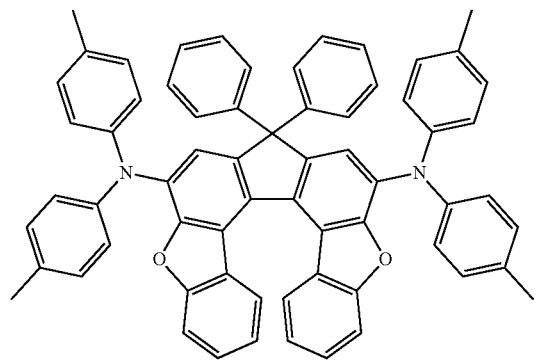
<Chemical Formula d211>
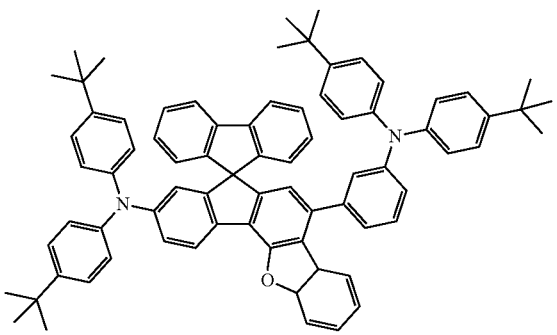
<Chemical Formula d212>
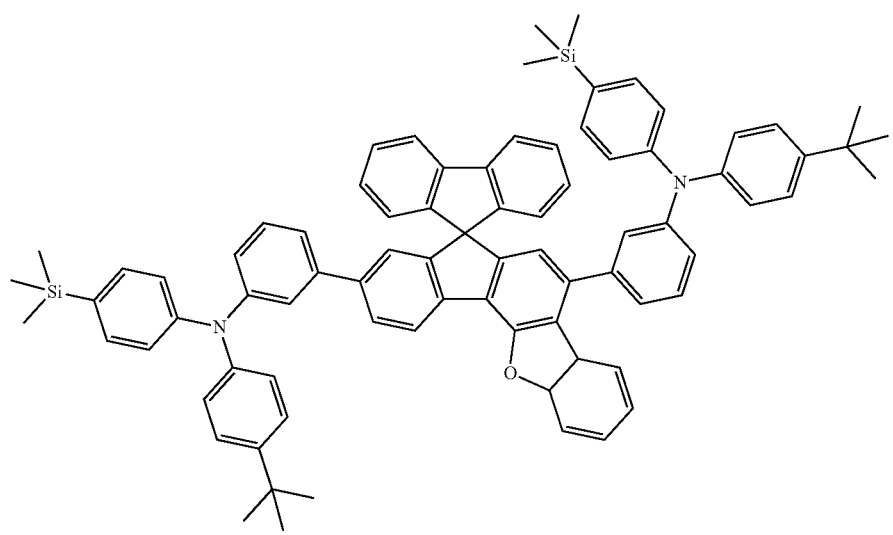
<Chemical Formula d213>
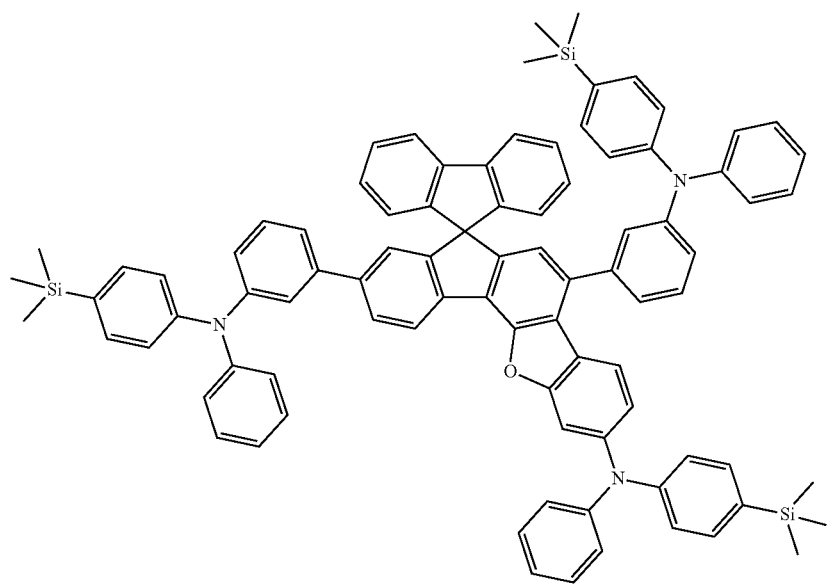

<Chemical Formula d214>
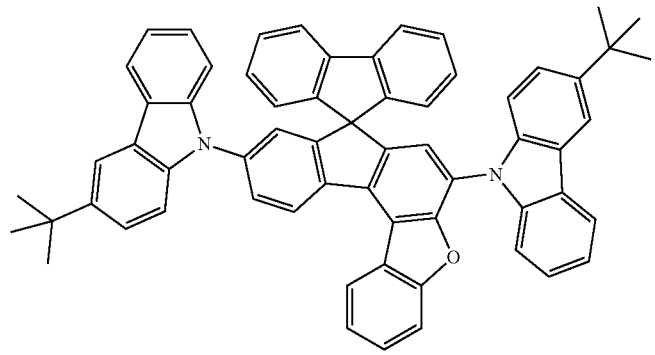
<Chemical Formula d215>
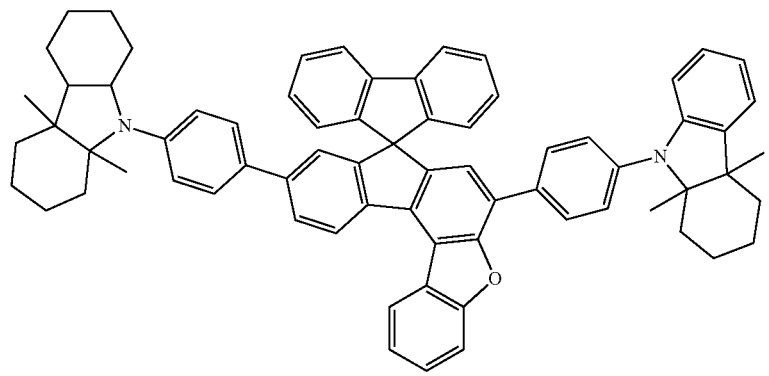
<Chemical Formula d216>
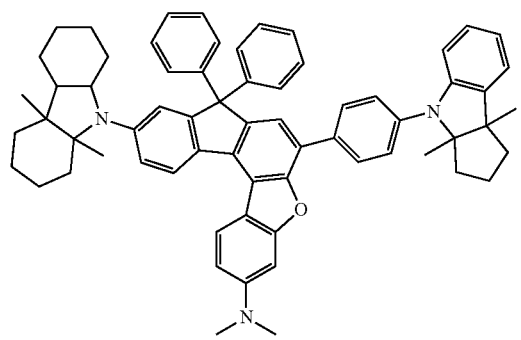
<Chemical Formula d217>
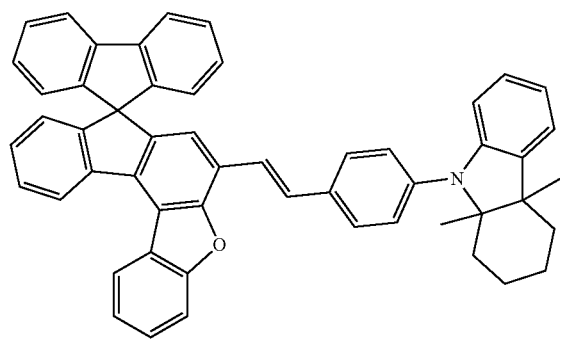
<Chemical Formula d218>
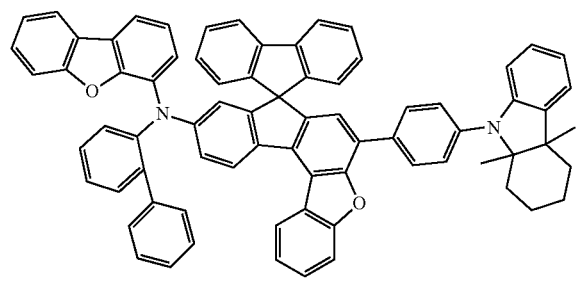
<Chemical Formula d219>
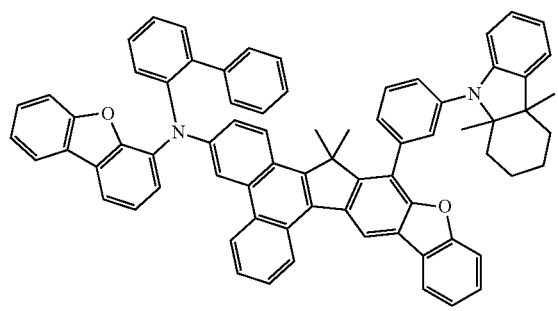

-continued
<Chemical Formula d220>
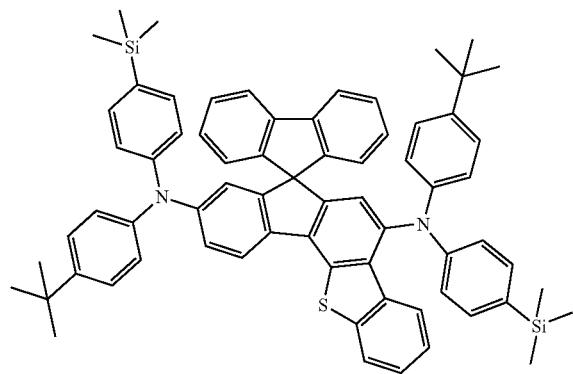
<Chemical Formula d221>
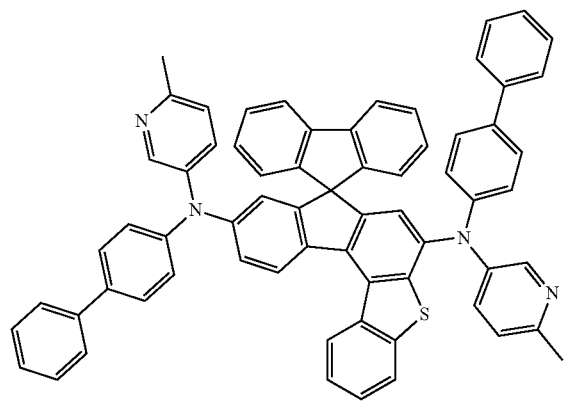
<Chemical Formula d222>
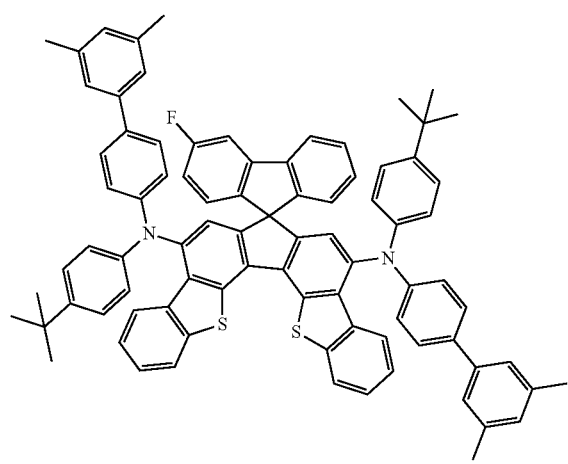
<Chemical Formula d223>
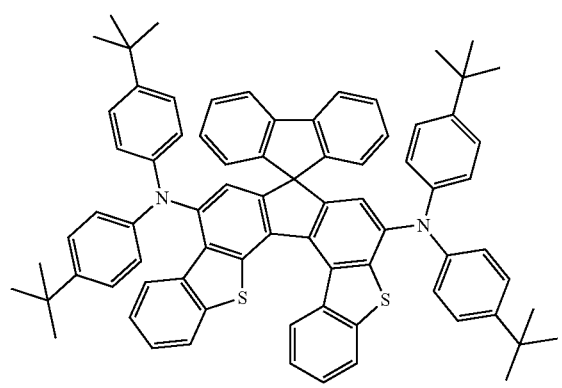
<Chemical Formula d224>
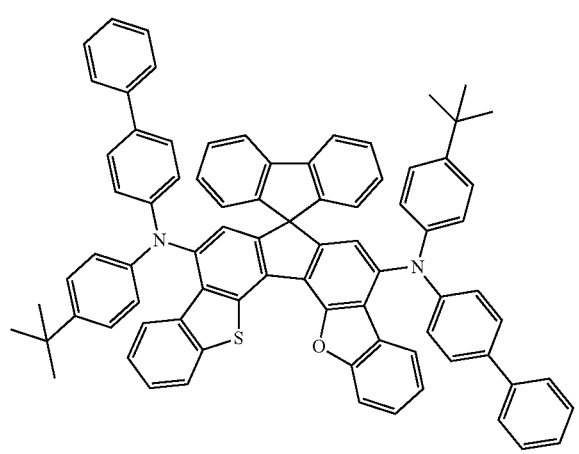
<Chemical Formula d225>
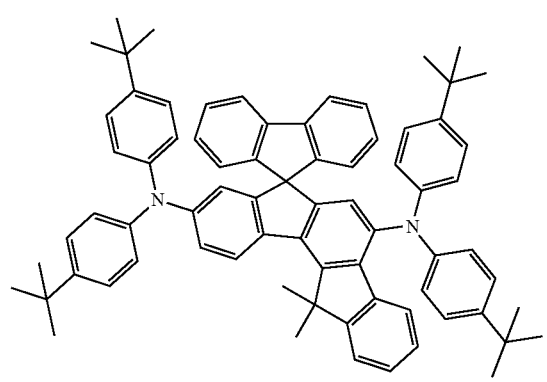

<Chemical Formula d226>
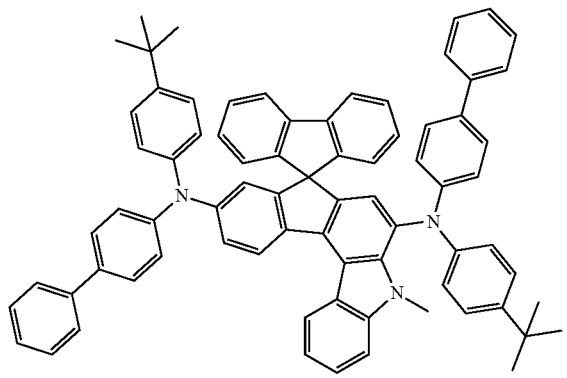
<Chemical Formula d227>
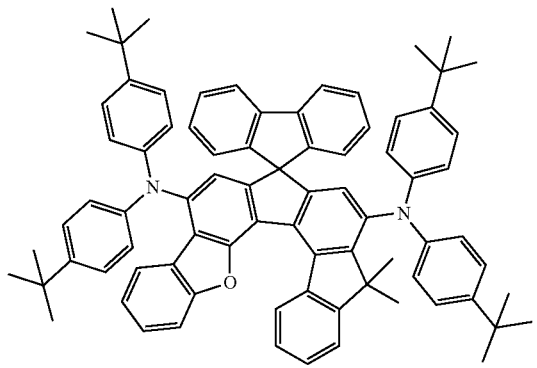
<Chemical Formula d228>
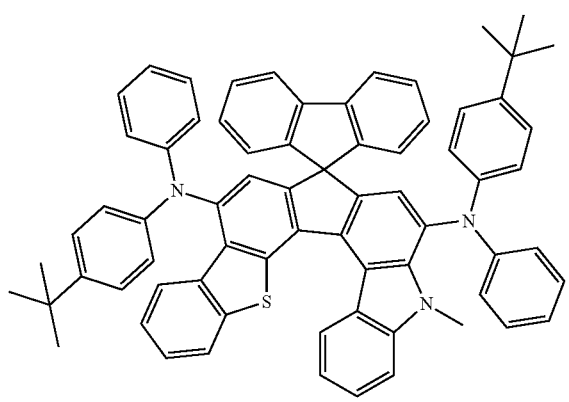
<Chemical Formula d229>
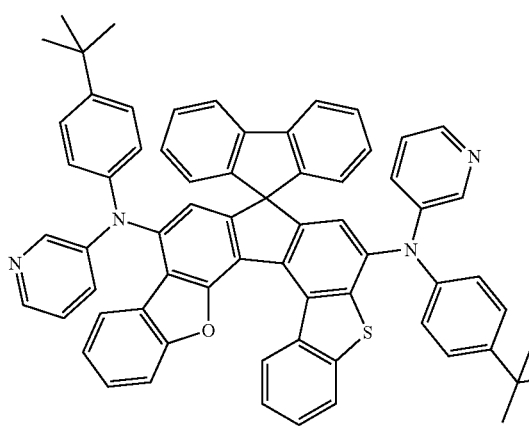
<Chemical Formula d230>
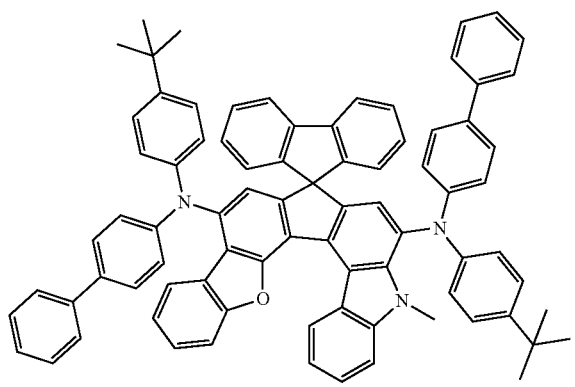
<Chemical Formula d231>
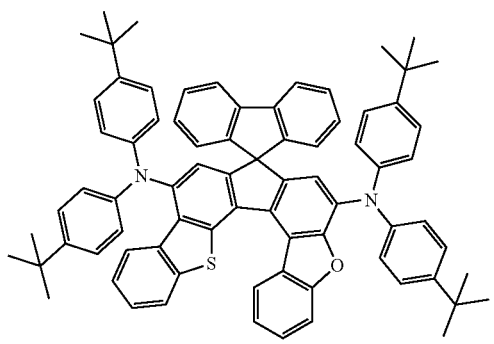
<Chemical Formula d232>
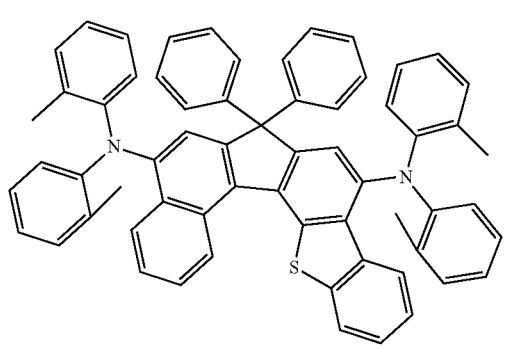

<Chemcial Formula d233>
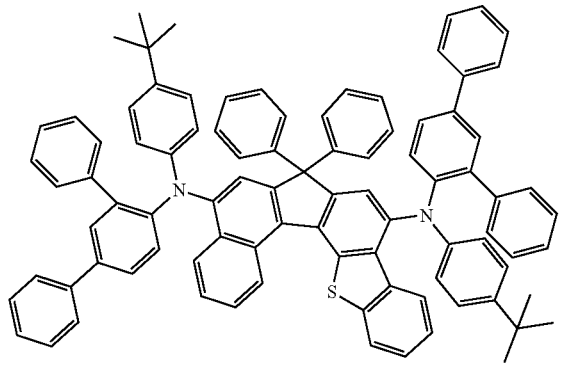
<Chemcial Formula d234>
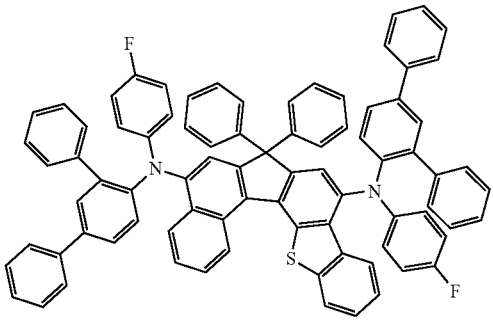
<Chemcial Formula d235>
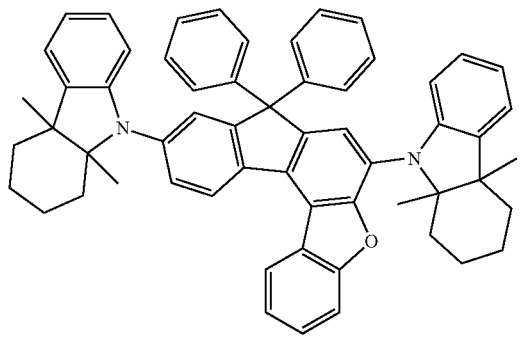
<Chemcial Formula d236>
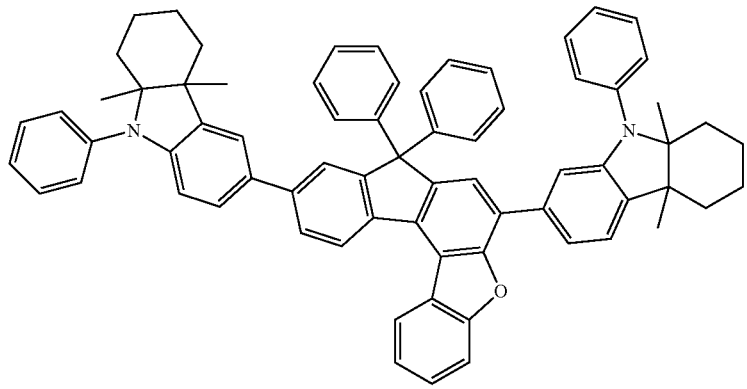
<Chemcial Formula d237>
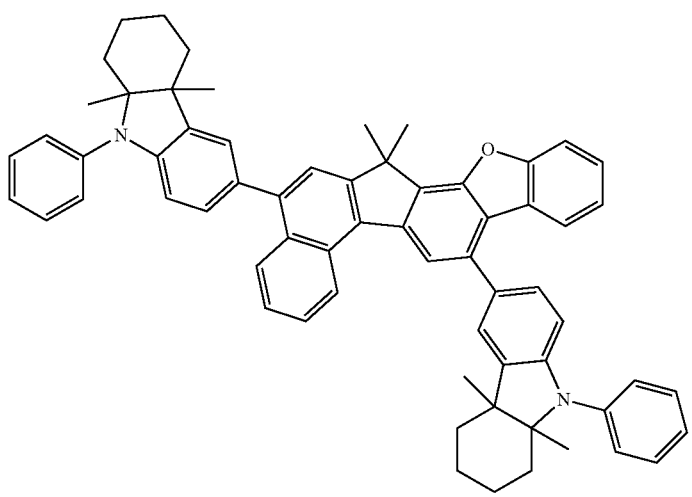

<Chemcial Formula d238>
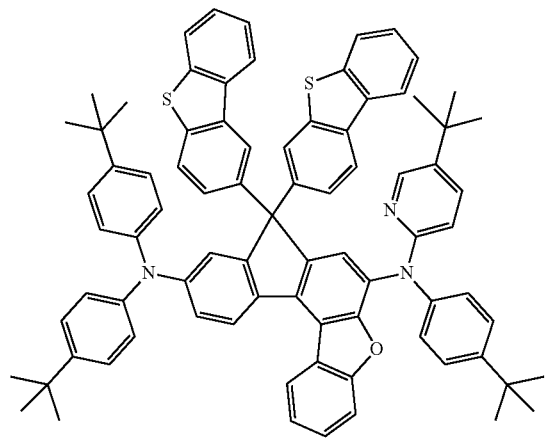
<Chemical Formula d239>
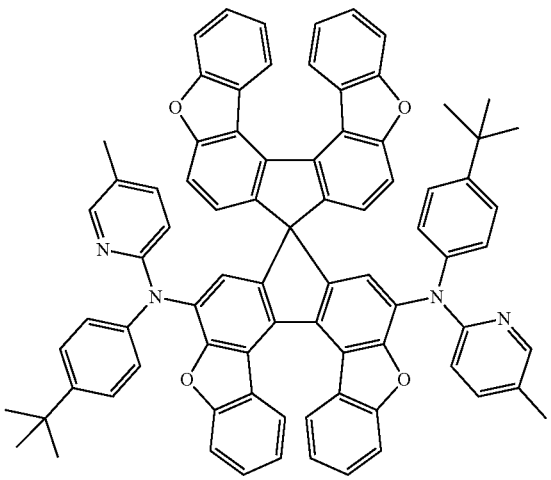
Furthermore, the compound represented by Chemical Formula D3 in the present disclosure may be any one selected from among compounds represented by following Chemical Formulas D101 to D133:
<Chemical Formula D101>
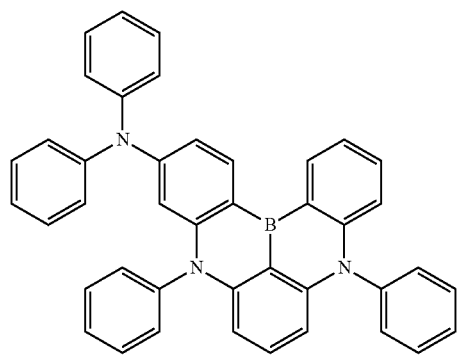
<Chemical Formula D102>
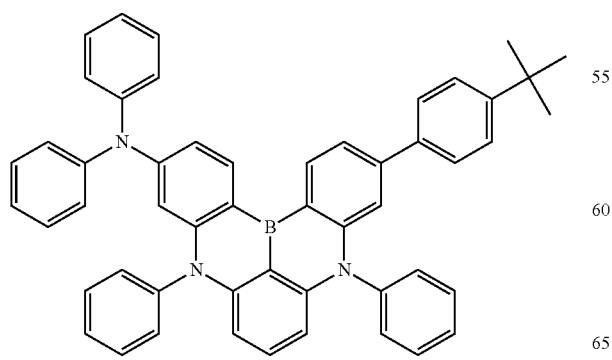
<Chemical Formula D103>
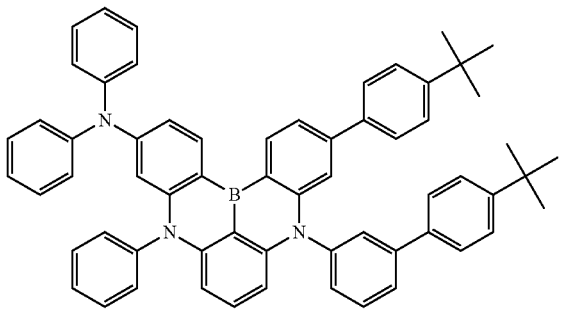
<Chemical Formula D104>
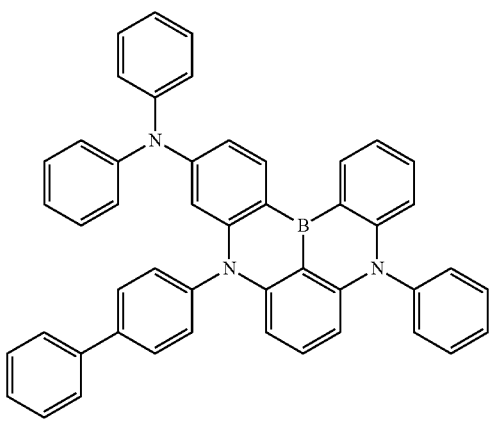

<Chemical Formula D105>
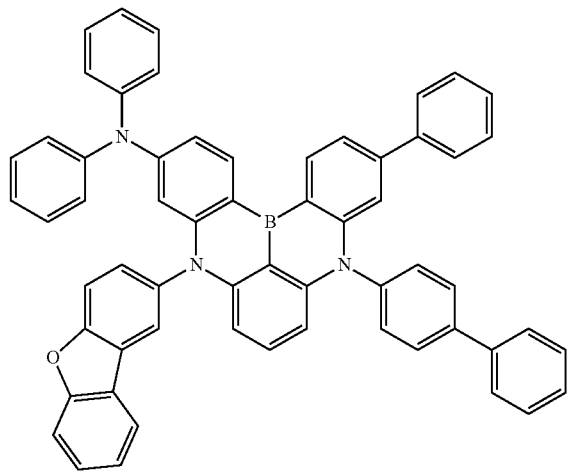
<Chemical Formula D106>
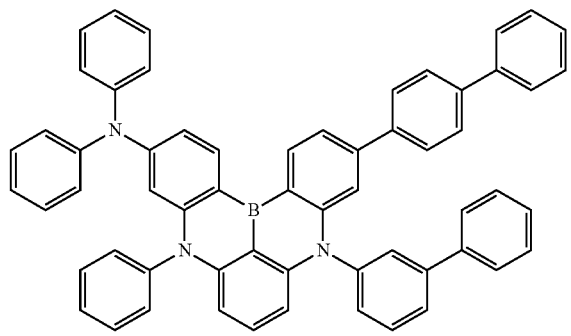
<Chemical Formula D107>
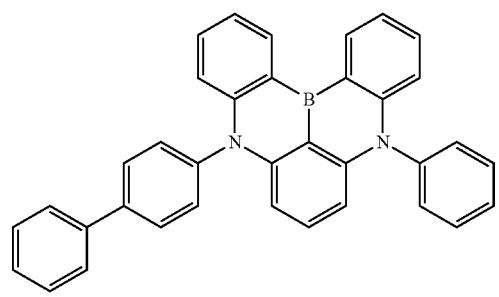
<Chemical Formula D108>
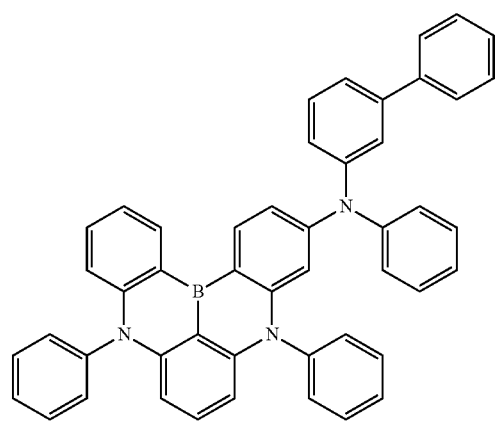
<Chemical Formula D109>
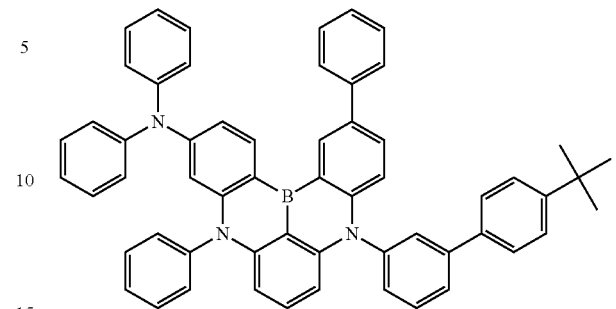
<Chemical Formula D110>
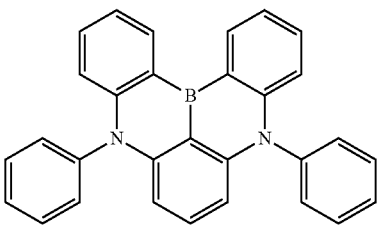
<Chemical Formula D111>
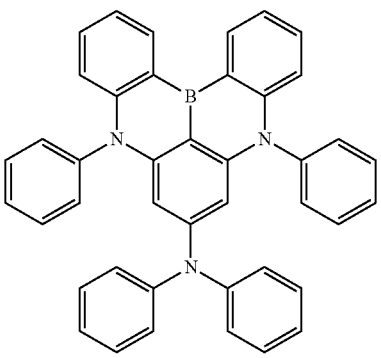
<Chemical Formula D112>
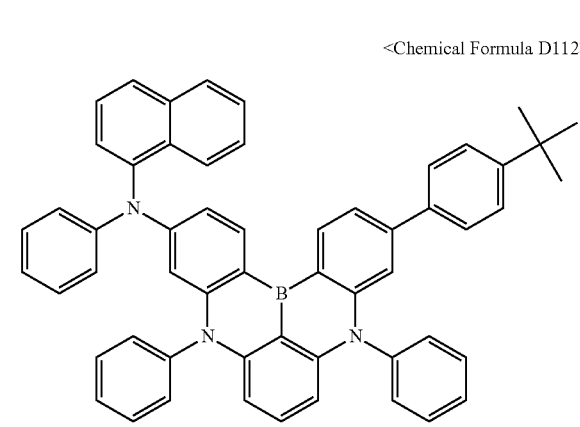

-continued
<Chemical Formula D113>
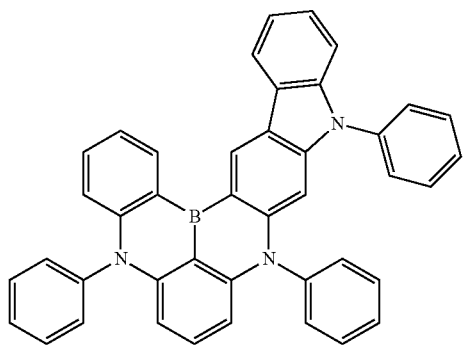
<Chemical Formula D114>
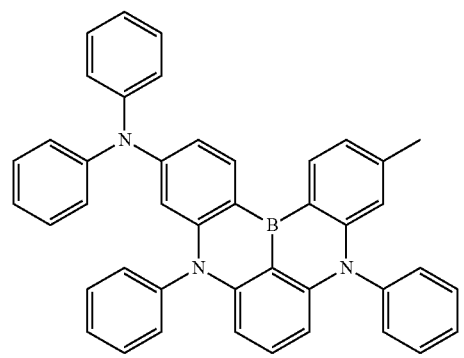
<Chemical Formula D115>
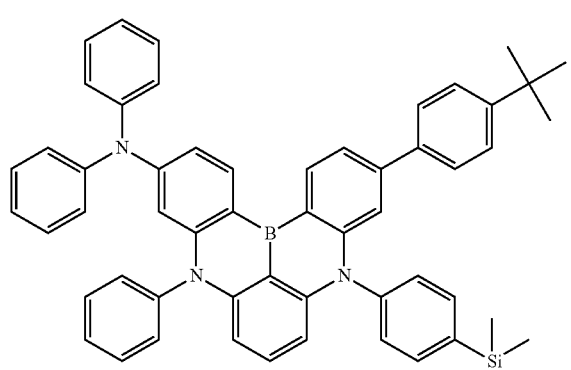
<Chemical Formula D116>
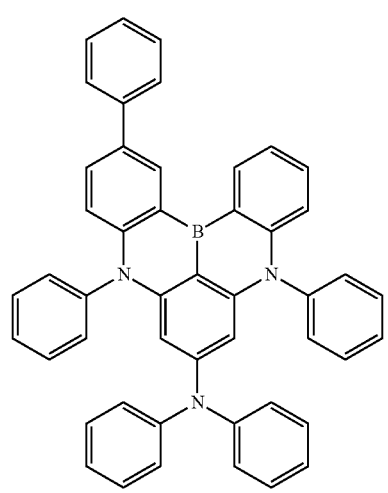
-continued
<Chemical Formula D117>
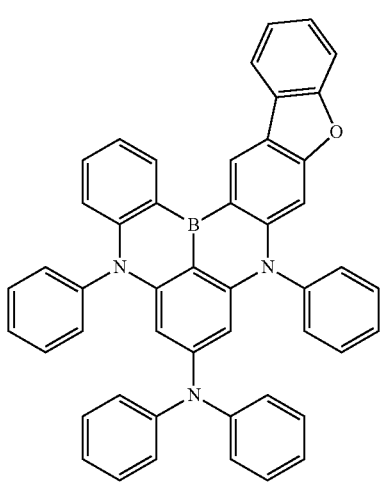
<Chemical Formula D118>
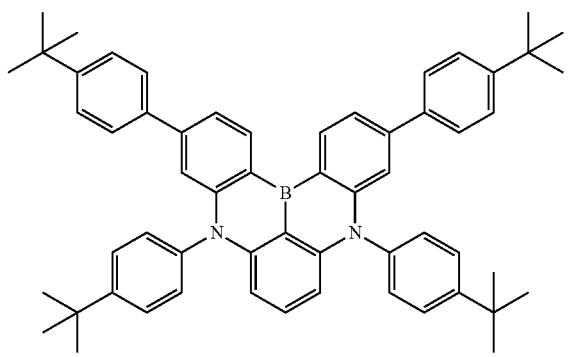
<Chemical Formula D119>
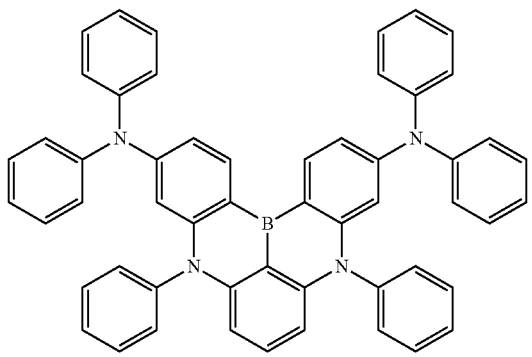

<Chemical Formula D120>
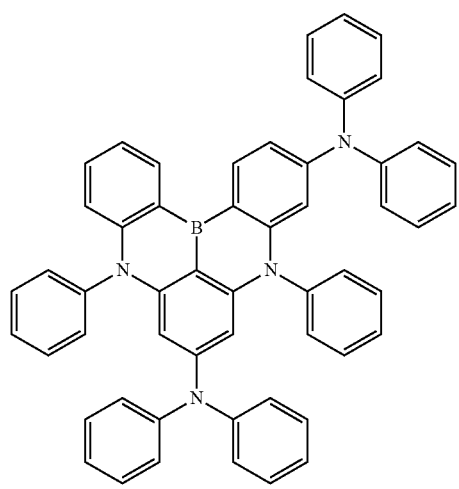
<Chemical Formula D121>
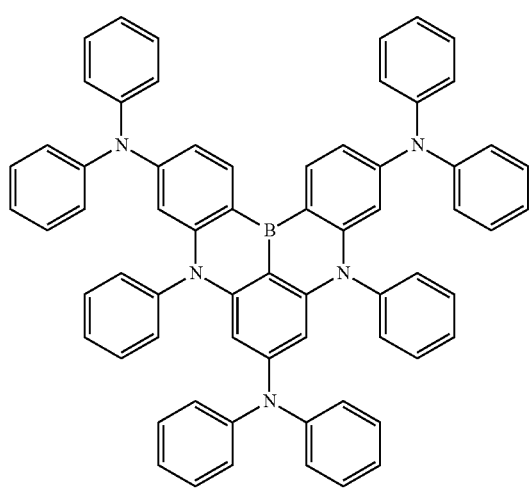
<Chemical Formula D122>
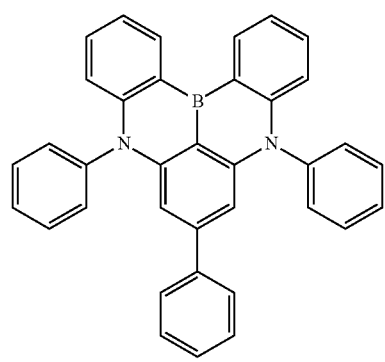
<Chemical Formula D123>
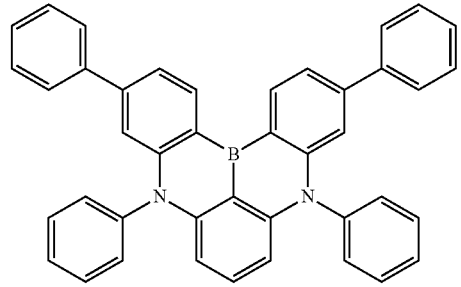
<Chemical Formula D124>
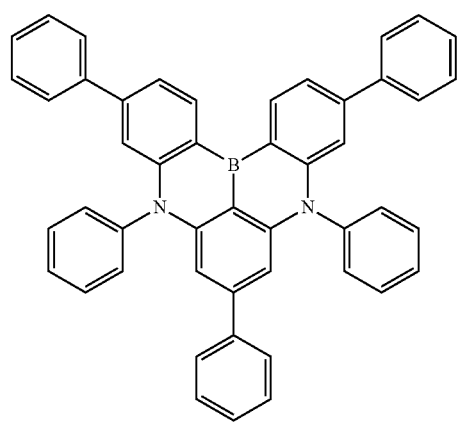
<Chemical Formula D125>
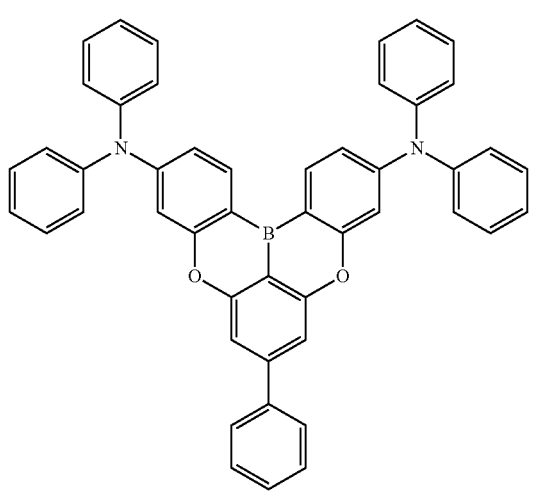

<Chemical Formula D126>
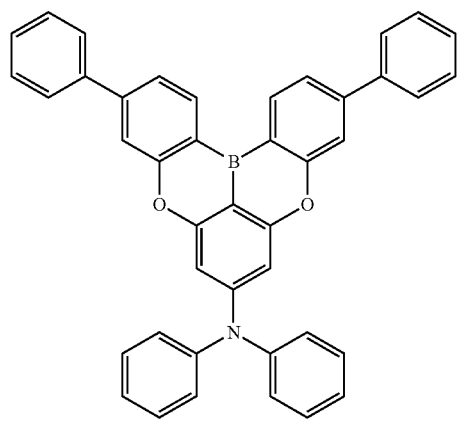
<Chemical Formula D127>
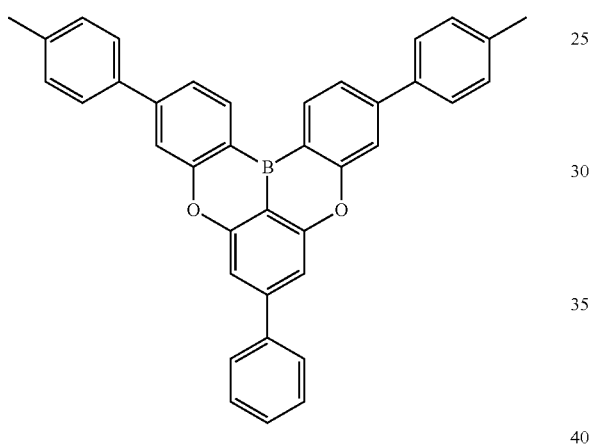
<Chemical Formula D128>
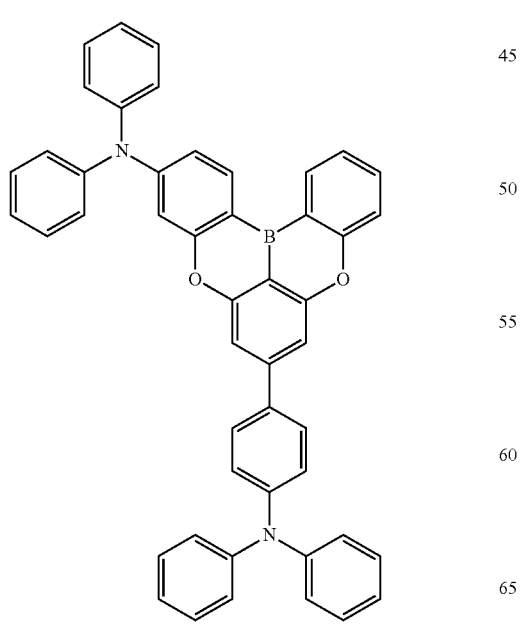
<Chemical Formula D129>
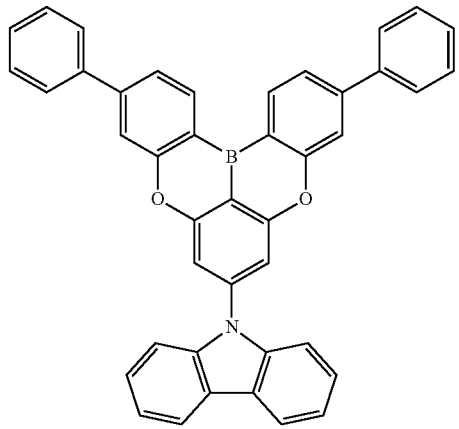
<Chemical Formula D130>
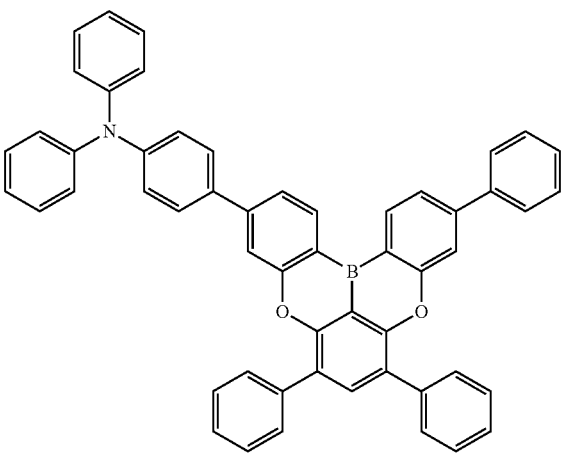
<Chemical Formula D131>
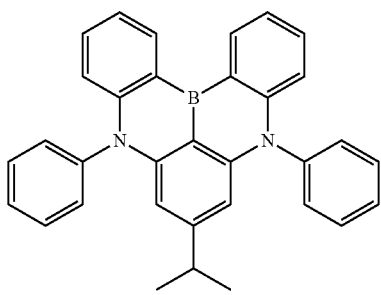

<Chemical Formula D132>
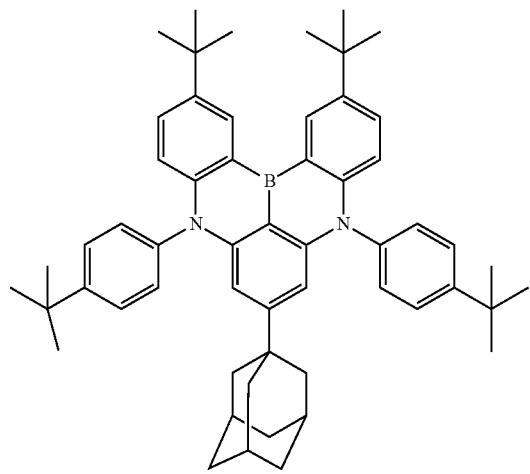
<Chemical Formula D133>
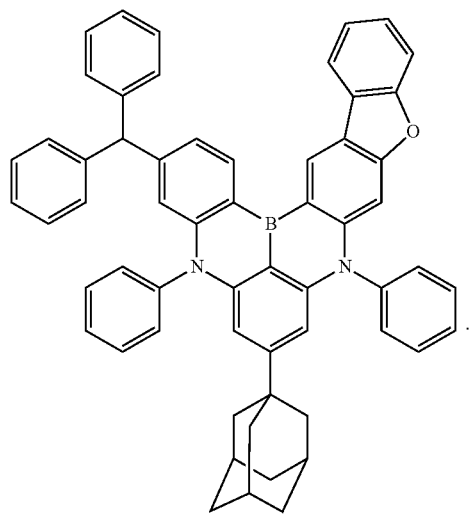
In addition, examples of the compound represented by Chemical Formula D4 or D5 include the compounds represented by the following Chemical Formula D201 to D280:
[Chemical Formula D201]
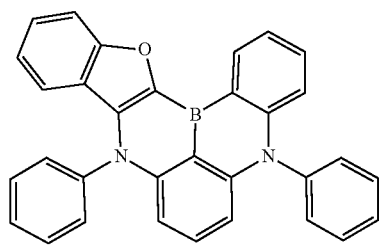
[Chemical Formula D202]
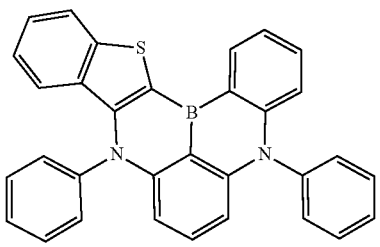
[Chemical Formula D203]
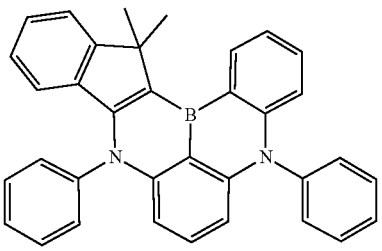
[Chemical Formula D204]
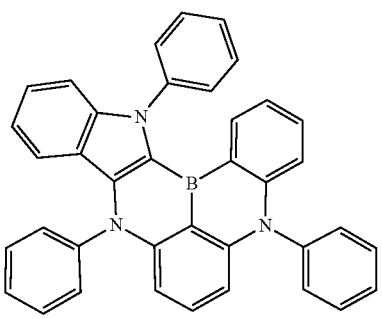
[Chemical Formula D205]
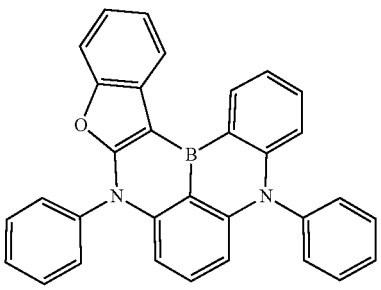
[Chemical Formula D206]
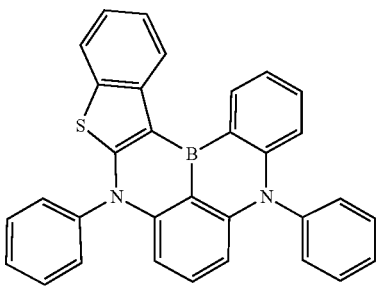

[Chemical Formula D207]
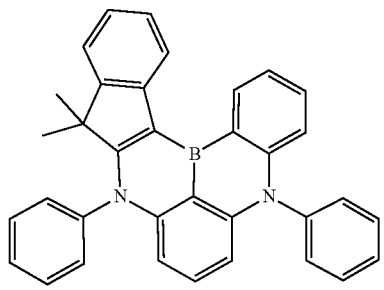
[Chemical Formula D211]
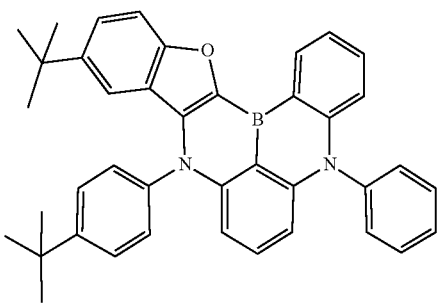
[Chemical Formula D208]
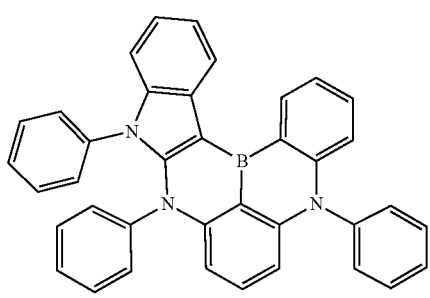
[Chemical Formula D212]
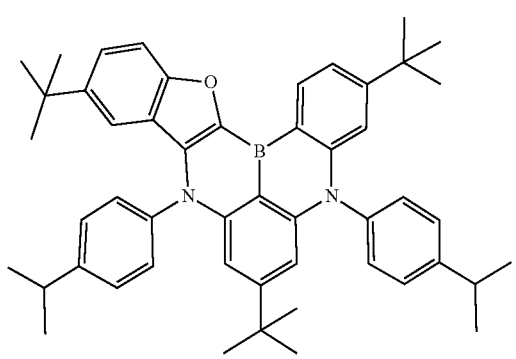
[Chemical Formula D209]
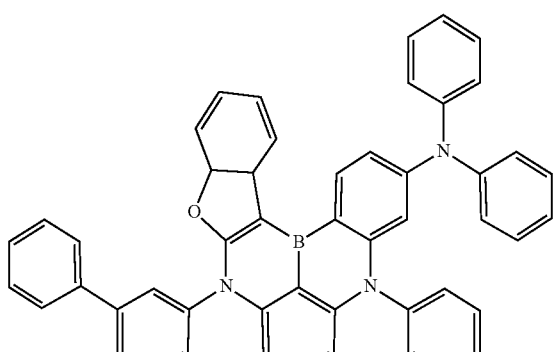
[Chemical Formula D213]
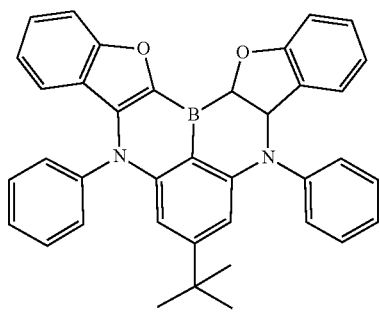
[Chemical Formula D210]
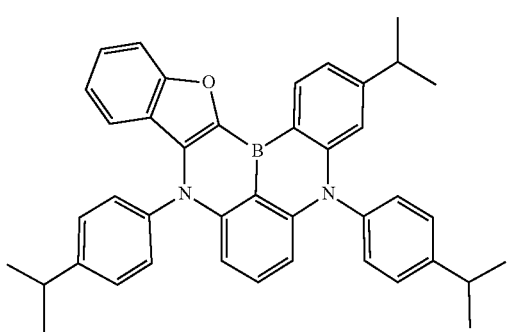
[Chemical Formula D214]
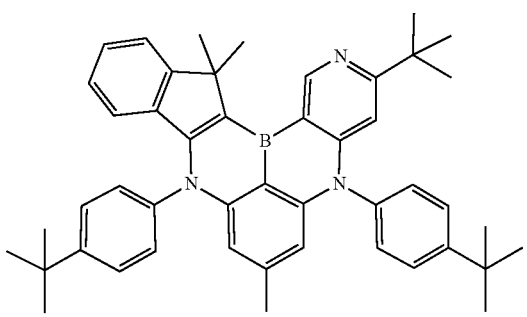

[Chemical Formula D215]
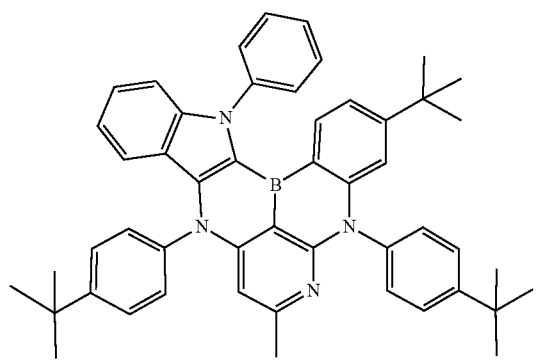
[Chemical Formula D219]
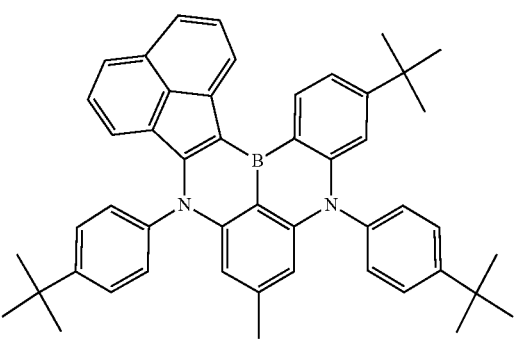
[Chemical Formula D216]
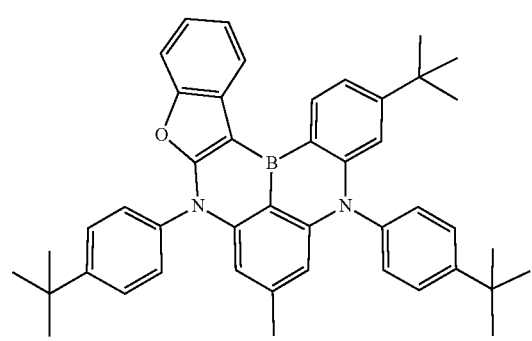
[Chemical Formula D220]
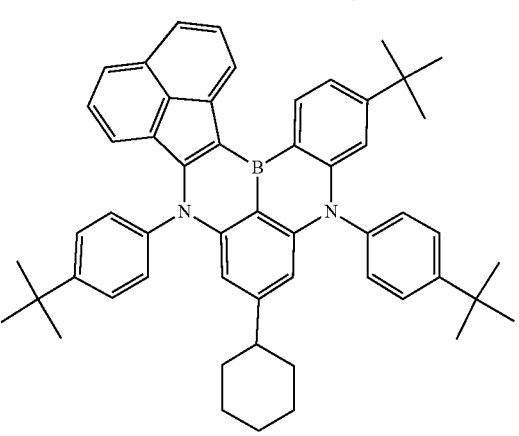
[Chemical Formula D217]
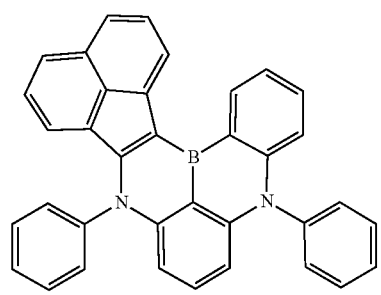
[Chemical Formula D221]
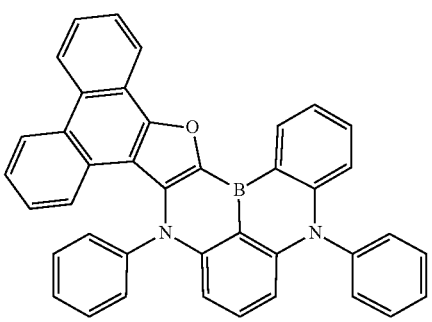
[Chemical Formula D218]
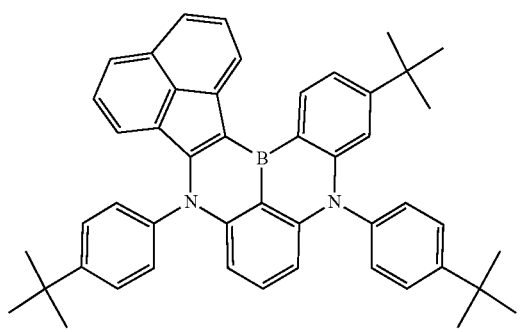
[Chemical Formula D222]
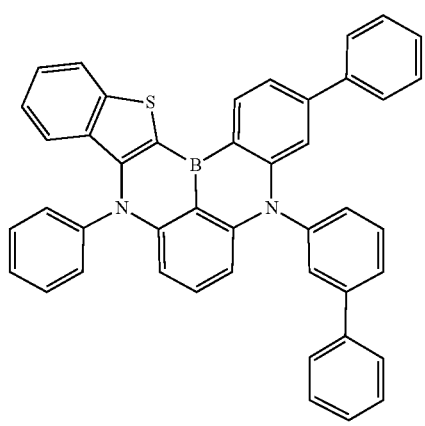

[Chemical Formula D223]
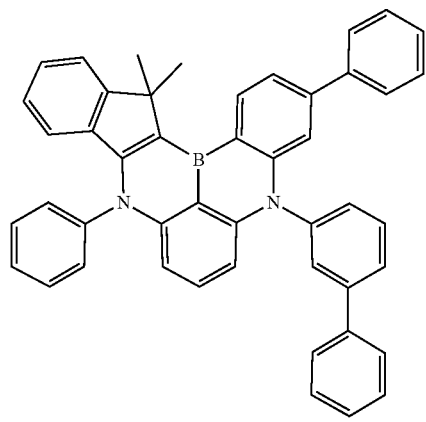
[Chemical Formula D224]
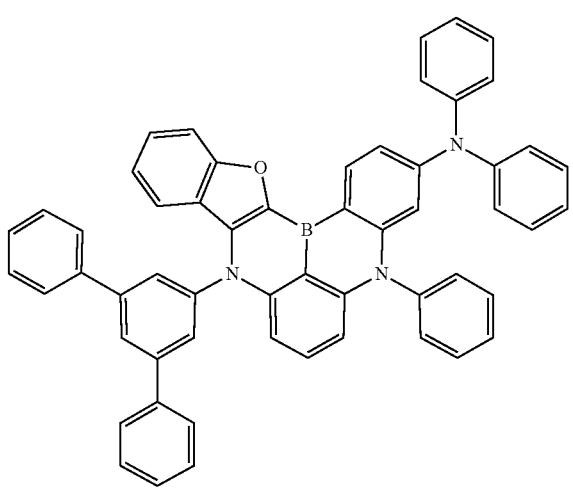
[Chemical Formula D225]
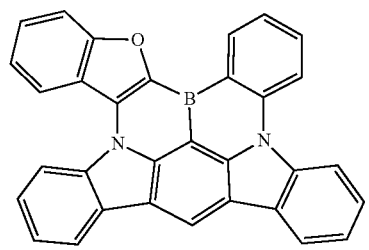
[Chemical Formula D226]
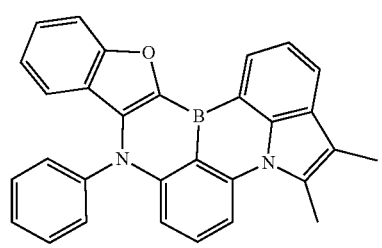
[Chemical Formula D227]
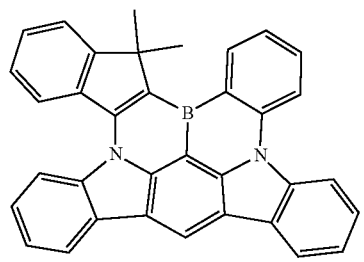
[Chemical Formula D228]
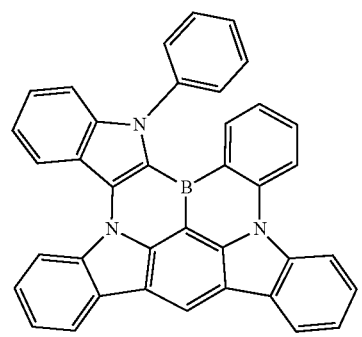
[Chemical Formula D229]
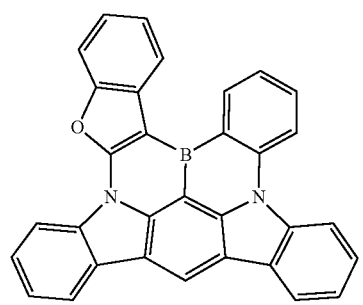
[Chemical Formula D230]
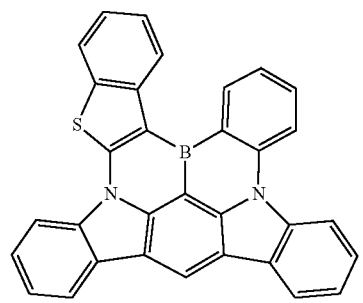
[Chemical Formula D231]
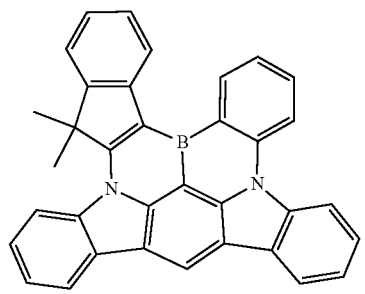

[Chemical Formula D232]
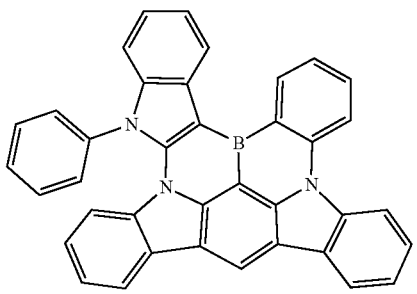
[Chemical Formula D233]
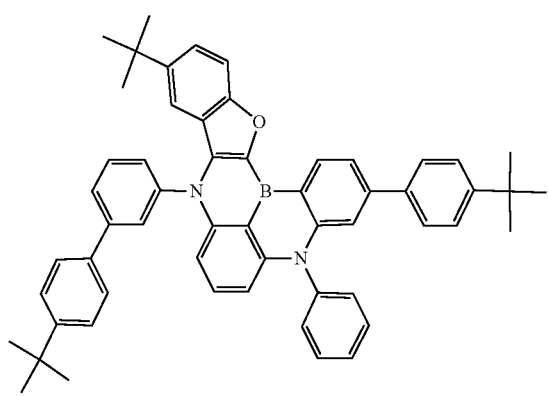
[Chemical Formula D234]
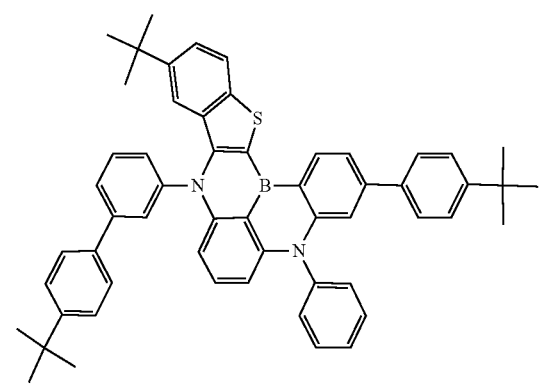
[Chemical Formula D235]
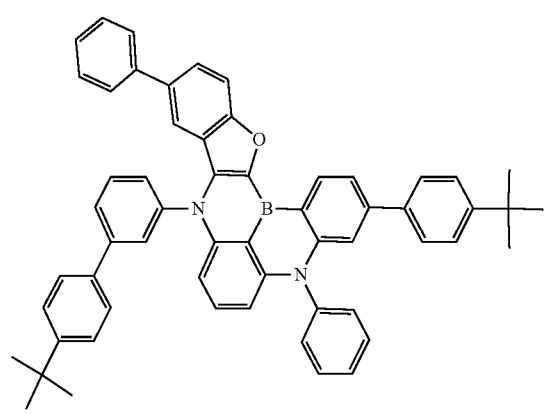
[Chemical Formula D236]
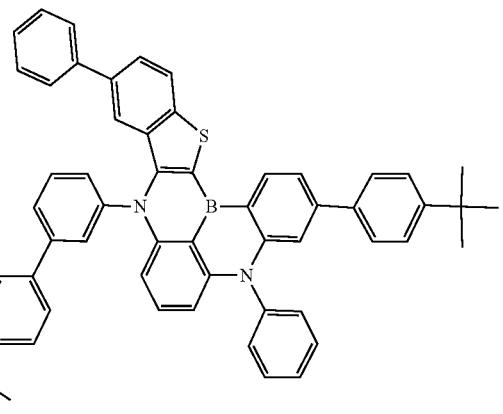
[Chemical Formula D237]
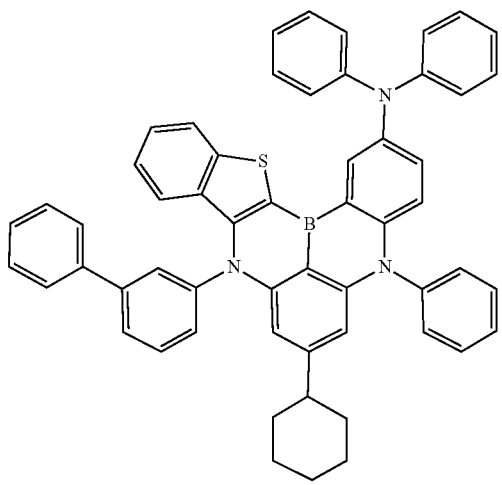
[Chemical Formula D238]
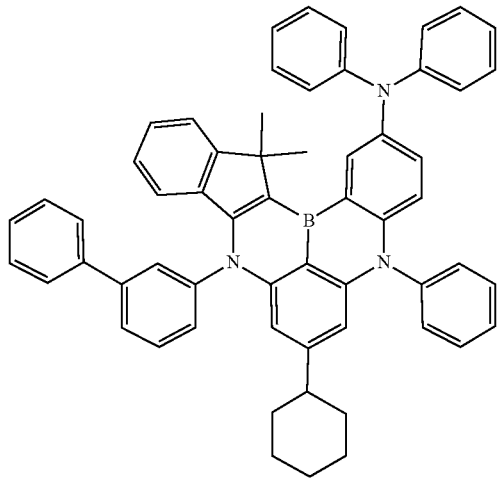

[Chemical Formula D239]
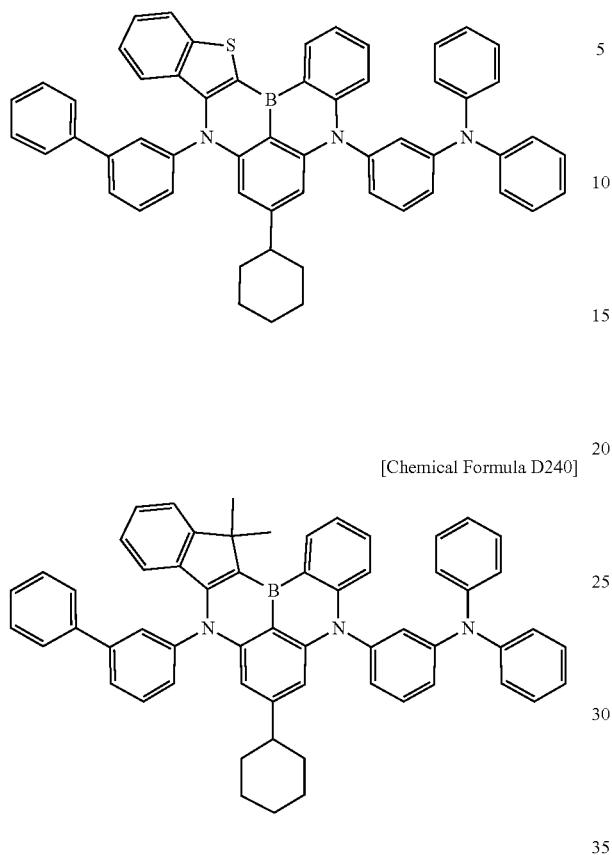
[Chemical Formula D240]
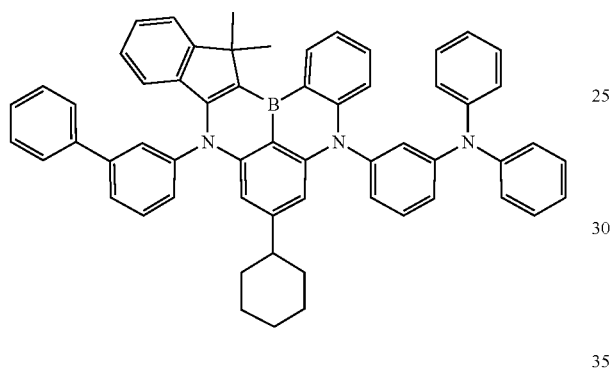
[Chemical Formula D241]
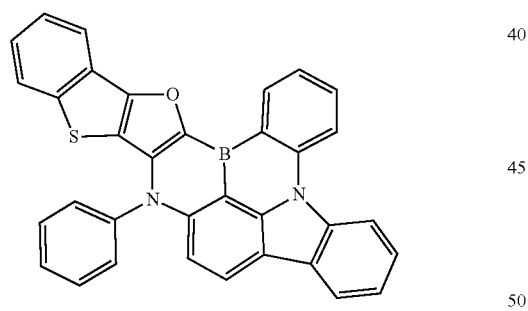
[Chemical Formula D242]
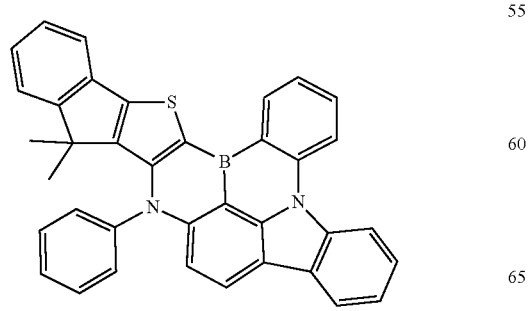
[Chemical Formula D243]
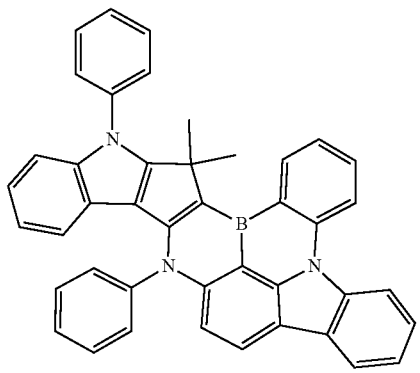
[Chemical Formula D244]
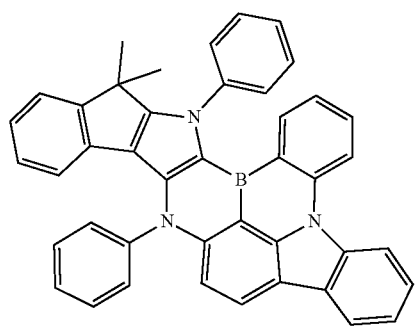
[Chemical Formula D245]
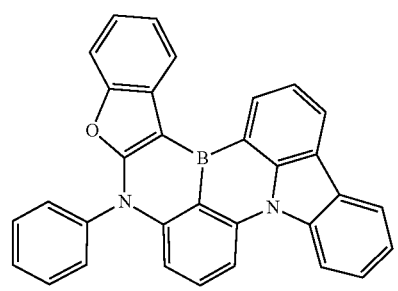
[Chemical Formula D246]
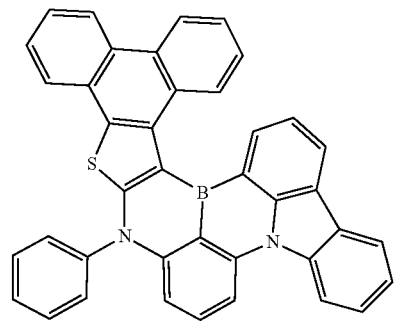

[Chemical Formula D247]
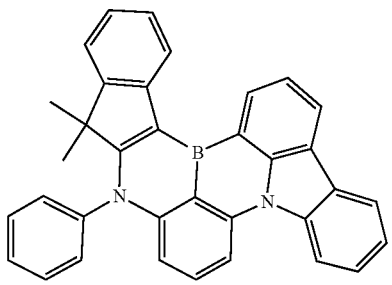
[Chemical Formula D248]
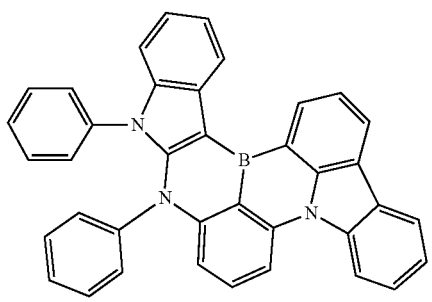
[Chemical Formula D249]
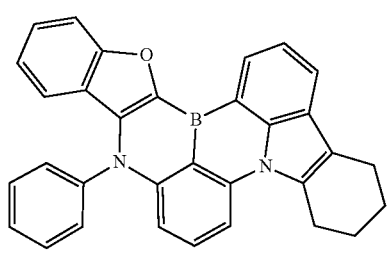
[Chemical Formula D250]
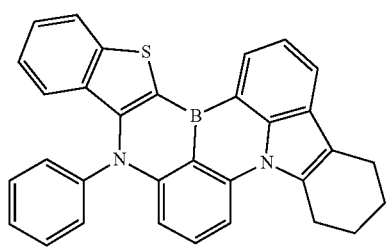
[Chemical Formula D251]
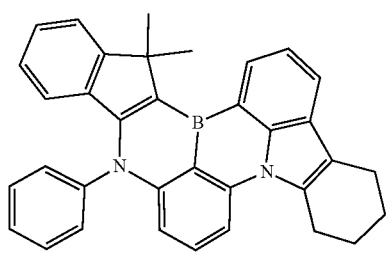
[Chemical Formula D252]
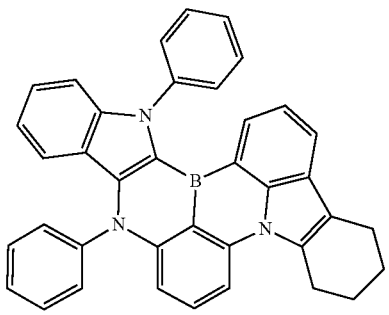
[Chemical Formula D253]
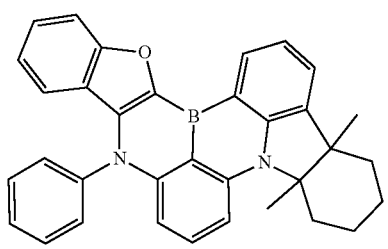
[Chemical Formula D254]
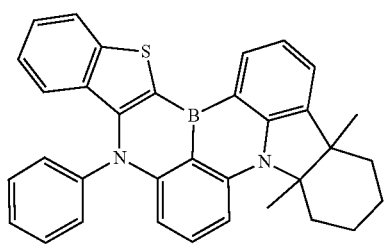
[Chemical Formula D255]
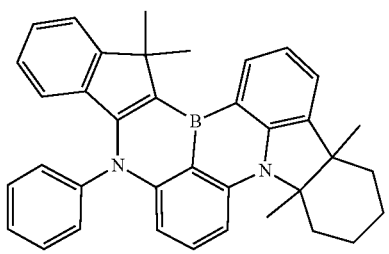
[Chemical Formula D256]
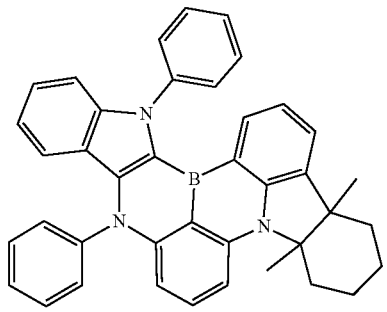

[Chemical Formula D257]
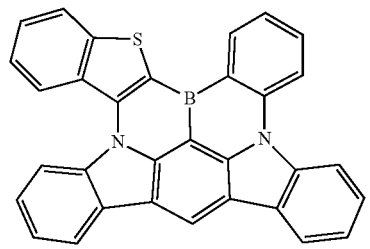
[Chemical Formula D258]
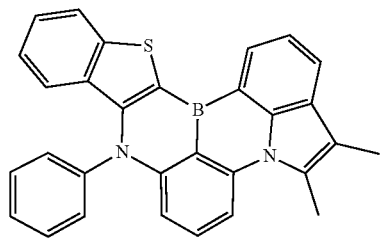
[Chemical Formula D259]
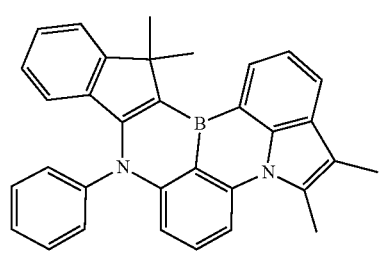
[Chemical Formula D260]
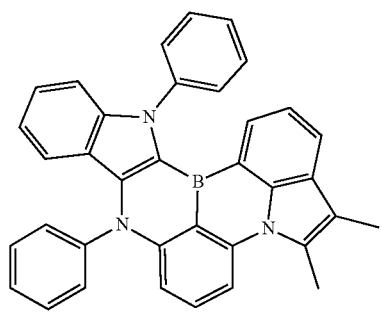
[Chemical Formula D261]
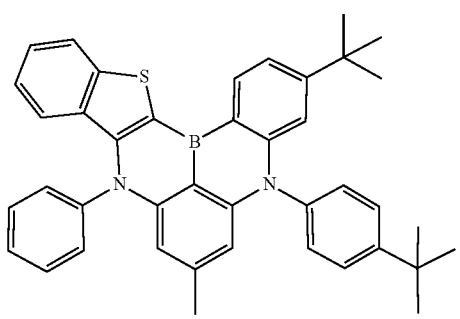
[Chemical Formula D262]
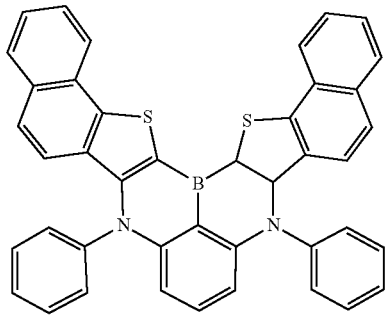
[Chemical Formula D263]
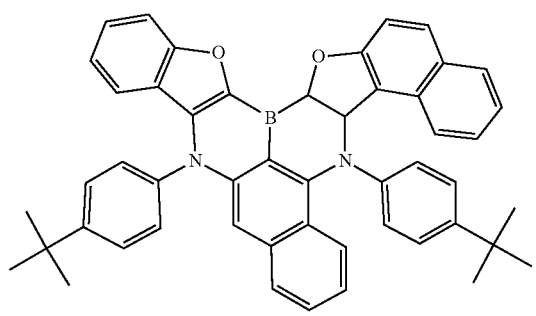
[Chemical Formula D264]
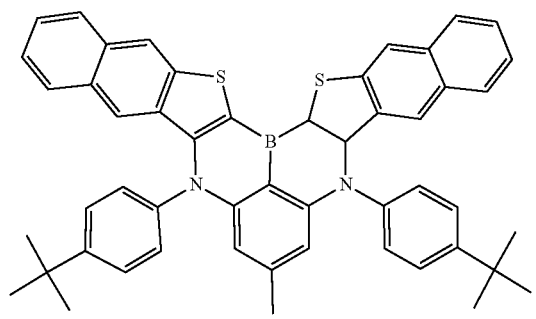
[Chemical Formula D265]
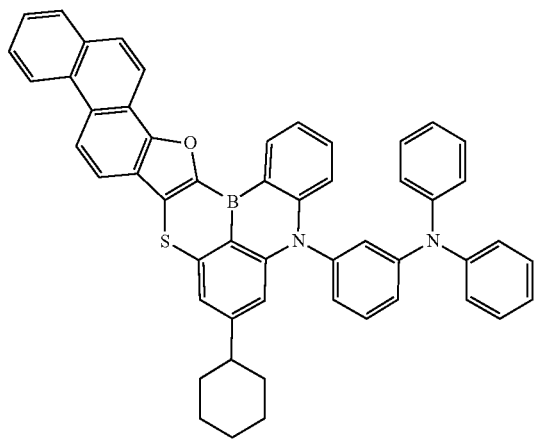

[Chemical Formula D266]
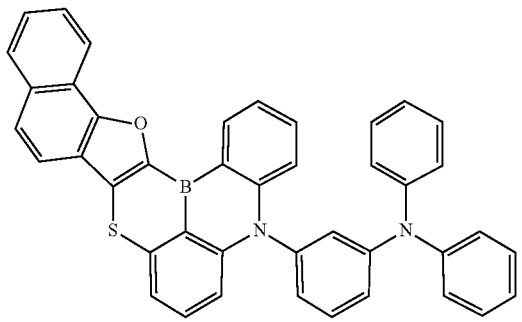
[Chemical Formula D267]
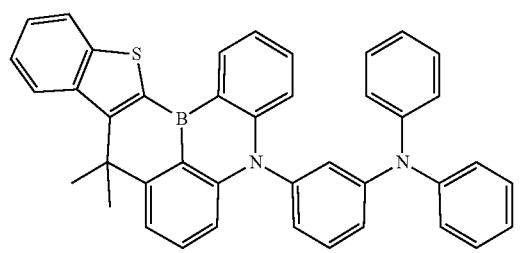
[Chemical Formula D268]
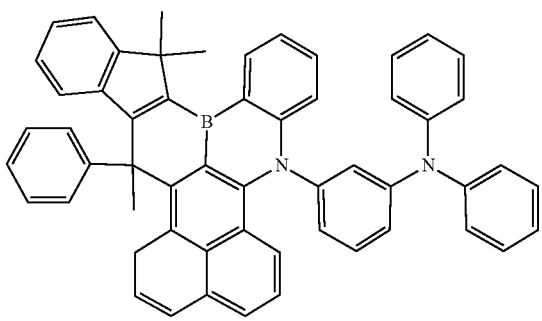
[Chemical Formula D269]
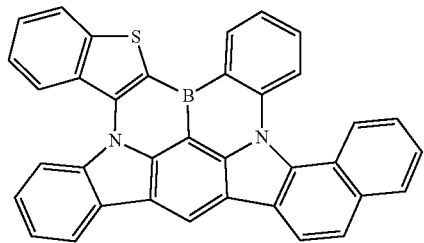
[Chemical Formuula D270]
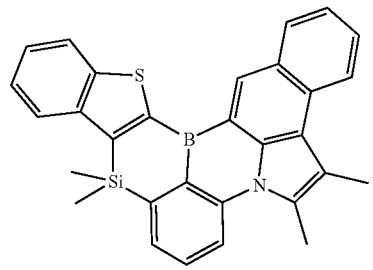
[Chemical Formula D271]
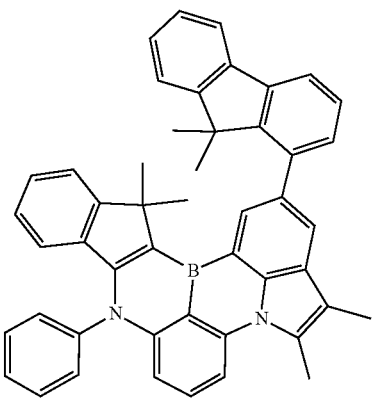
[Chemical Formula D272]
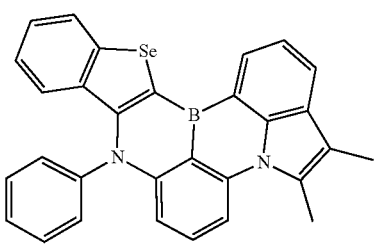
[Chemical Formula D273]
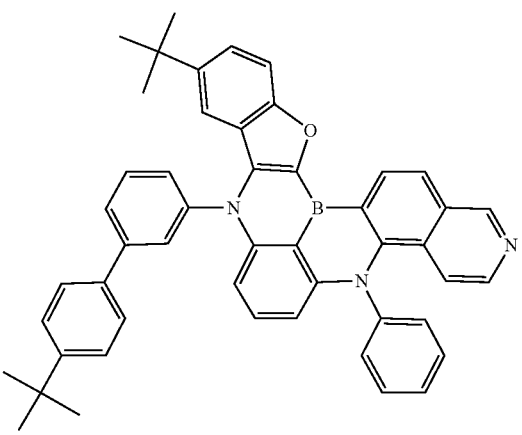
[Chemical Formula D274]
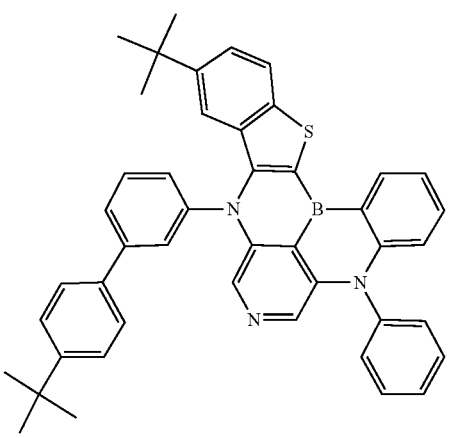

[Chemical Formula D275]

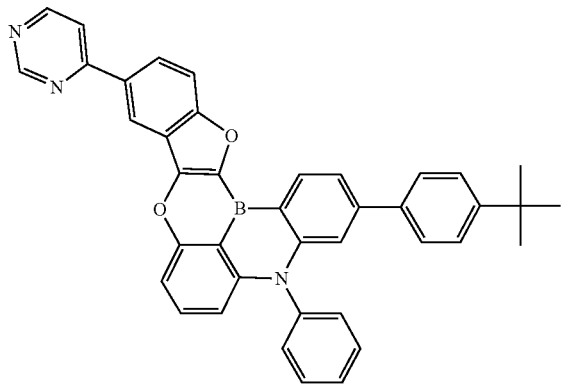

[Chemical Formula D276]

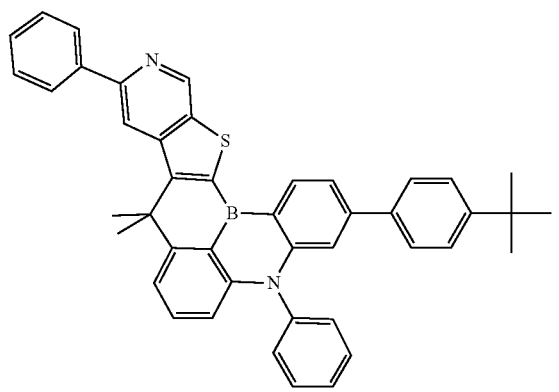

[Chemical Formula D277]

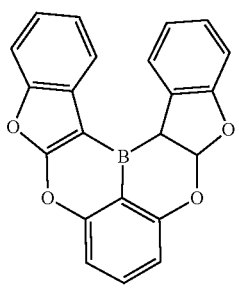

[Chemical Formula D278]

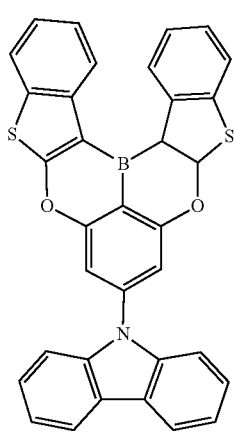

[Chemical Formula D279]

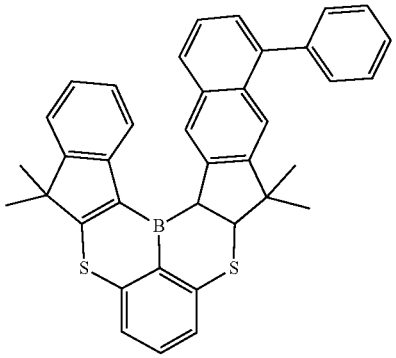

[Chemical Formula D280]

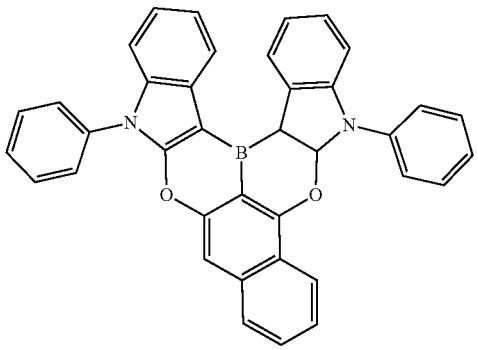

The content of the dopant in the light-emitting layer may usually range from about 0.01 to 20 parts by weight, based on 100 parts by weight of the host, but is not limited thereto.

In addition to the above-mentioned dopant and host, the light-emitting layer may further contain various hosts and various dopants.

Below, the organic light-emitting diode according to an embodiment of the present disclosure is explained with reference to the drawing.

FIG. 1 is a schematic cross-sectional view of the structure of an organic light-emitting diode according to an embodiment of the present disclosure.

As shown in FIG. 1, the organic light-emitting diode according to an embodiment of the present disclosure comprises an anode 20, a hole transport layer 40, a light-emitting layer 50 containing a host and a dopant, an electron transport layer 60, and a cathode 80 in that order, wherein the anode and the cathode serve as a first electrode and a second electrode, respectively, with the interposition of the hole transport layer between the anode and the light-emitting layer and the electron transport layer between the light-emitting layer and the cathode.

In addition, the hole transport layer 40 may include a first hole transport layer and a second hole transport layer, with the interposition of the second hole transport layer between the first hole transport layer and the light-emitting layer. Here, the organic light-emitting compound represented by Chemical Formula A or B may be used as a material for the second hole transport layer in the organic light-emitting diode of the present disclosure. Characterized by the structure, the organic light-emitting diode according to the present disclosure can exhibit high efficiency and a prolonged lifetime.

Furthermore, the organic light-emitting diode according to an embodiment of the present disclosure may comprise a hole injection layer 30 between the anode 20 and the hole transport layer 40 and an electron injection layer 70 between the electron transport layer 60 and the cathode 80.

Reference is made to FIG. 1 with regard to the fabrication of the organic light-emitting diode of the present disclosure.

First, the top of a substrate 10 is coated with an anode electrode material to form an anode 20. So long as it is used in a typical organic EL device, any substrate may be used as the substrate 10. Preferable is an organic substrate or transparent plastic substrate that exhibits excellent transparency, surface smoothness, ease of handling, and waterproofness. As the anode electrode material, indium tin oxide (ITO), indium zinc oxide (IZO), tin oxide (SnO$_2$), or zinc oxide (ZnO), which are transparent and superior in terms of conductivity, may be used.

A hole injection layer material is applied onto the anode electrode 20 by thermal deposition in a vacuum or by spin coating to form a hole injection layer 30. Subsequently, thermal deposition in a vacuum or spin coating may also be conducted to form a hole transport layer 40 with a hole transport layer material on the hole injection layer 30.

As concerning the materials of the hole injection layer 30, they may be the compounds represented by Chemical Formula A or B. No particular limitations are imparted to the hole injection layer material, as long as it is one that is typically used in the art. For example, mention may be made of 2-TNATA [4,4',4"-tris(2-naphthylphenyl-phenylamino)-triphenylamine], NPD [N,N'-di(1-naphthyl)-N,N'-diphenyl-benzidine)], TPD [N,N'-diphenyl-N,N'-bis(3-methylphenyl)-1,1'-biphenyl-4,4'-diamine], and DNTPD [N,N'-diphenyl-N,N'-bis-[4-(phenyl-m-tolylamino)-phenyl]-biphenyl-4,4'-diamine], but the present disclosure is not limited thereby.

In addition, the material for the hole transport layer 40 may include the organic light-emitting compound, represented by Chemical Formula A or B, according to the present disclosure. In particular embodiments, the hole transport layer is divided into a first hole transport layer and a second hole transport layer wherein the organic light-emitting compound represented by Chemical Formula A or B is used in the second hole transport layer while a material typically used in the art may be available in the first hole transport layer, without particular limitations thereto. Examples of the material include, but are not limited to, N,N'-bis(3-methylphenyl)-N,N'-diphenyl-[1,1-biphenyl]-4,4'-diamine (TPD) and N,N'-di(naphthalen-1-yl)-N,N'-diphenylbenzidine (a-NPD).

Subsequently, the light-emitting layer 50 may be deposited on the hole transport layer 40 by vacuum deposition or by spin coating.

Here, the light-emitting layer 50 may be composed of a host and a dopant. The materials for the host and the dopant are as defined above.

In some embodiments of the present disclosure, the light-emitting layer 50 particularly ranges in thickness from 50 to 2,000 Å.

Then, the electron transport layer 60 is deposited on the light-emitting layer by vacuum deposition or by spin coating.

A material for use in the electron transport layer 60 functions to stably carry the electrons injected from the electron injection electrode (cathode), and may be an electron transport material known in the art. Examples of the electron transport material known in the art include quinoline derivatives, particularly, tris(8-quinolinorate)aluminum (Alq3), Liq, TAZ, BAlq, beryllium bis(benzoquinolin-10-olate) (Bebq2), Compound 201, Compound 202, BCP, and oxadiazole derivatives such as PBD, BMD, and BND, but are not limited thereto:

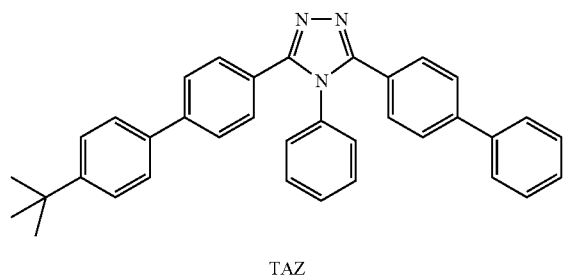

TAZ

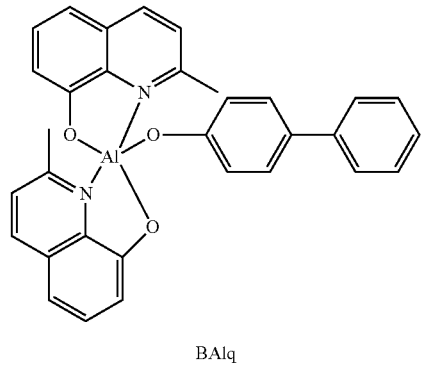

BAlq

<Compound 201>

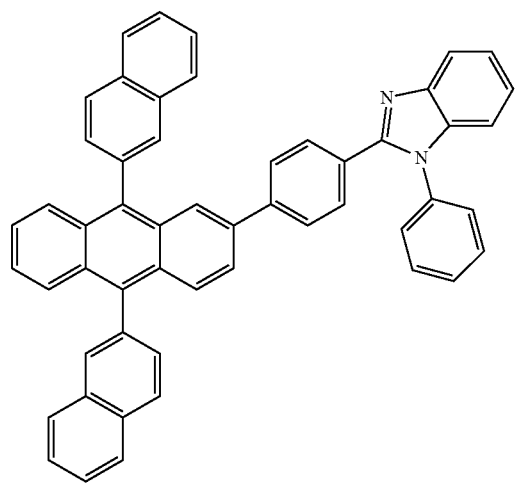

-continued

<Compound 202>

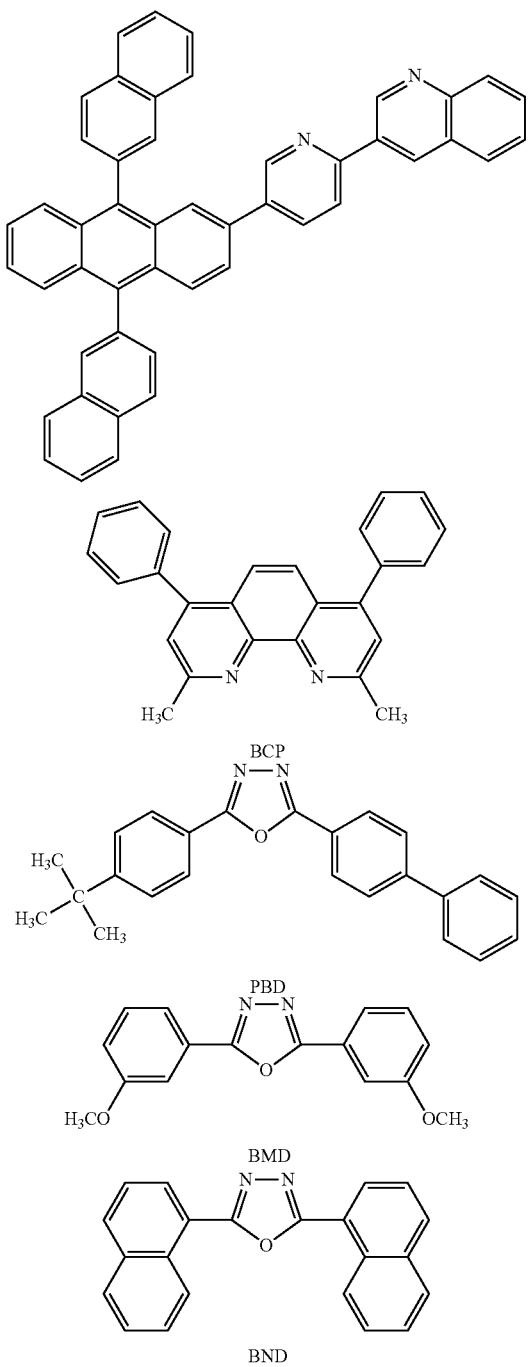

BCP

BND

After formation of the electron transport layer, an electron injection layer (EIL) that functions to facilitate electron injection from the cathode may be further deposited on the electron transport layer. No particular limitations are imparted to the material of EIL.

Any material that it is conventionally used in the art can be available for the electron injection layer 70 without particular limitations. Examples include CsF, NaF, LiF, $Li_2O$, and BaO. A deposition condition of the electron injection layer may be almost the same as that for the hole injection layer.

The electron injection layer 70 may range in thickness from about 1 Å to about 100 Å and particularly from about 3 Å to about 90 Å. Given the thickness range for the electron injection layer, the diode can exhibit satisfactory electron injection properties without actually elevating a driving voltage.

In order to facilitate electron injection, the cathode 80 may be made of a material having a small work function, such as metal or metal alloy such as lithium (Li), magnesium (Mg), calcium (Ca), aluminum (Al), aluminum-lithium (Al—Li), magnesium-indium (Mg—In), and magnesium-silver (Mg—Ag). Alternatively, ITO or IZO may be employed to form a transparent cathode for a top-emitting organic light-emitting diode.

Moreover, the organic light-emitting diode of the present disclosure may further comprise a light-emitting layer containing a blue, green, or red luminescent material that emits radiation in the wavelength range of 380 nm to 800 nm. That is, the light-emitting layer in the present disclosure has a multi-layer structure wherein the blue, green, or red luminescent material may be a fluorescent material or a phosphorescent material.

Furthermore, at least one selected from among the layers may be deposited using a single-molecule deposition process or a solution process.

Here, the deposition process is a process by which a material is vaporized in a vacuum or at a low pressure and deposited to form a layer, and the solution process is a method in which a material is dissolved in a solvent and applied for the formation of a thin film by means of inkjet printing, roll-to-roll coating, screen printing, spray coating, dip coating, spin coating, etc.

Also, the organic light-emitting diode of the present disclosure may be applied to a device selected from among flat display devices, flexible display devices, monochrome or grayscale flat illumination devices, and monochrome or grayscale flexible illumination devices.

A better understanding of the present disclosure may be obtained through the following examples which are set forth to illustrate, but are not to be construed as limiting the present invention.

Preparation Example 1: Synthesis of Compound 4

Synthesis of Intermediate 1-1

[Reaction Scheme 1-1]

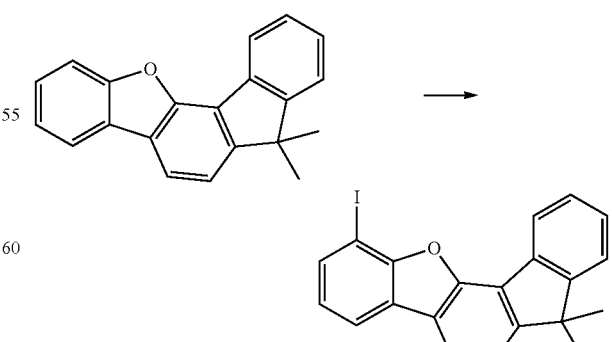

[Intermediate 1-1]

Together with THF (1500 ml, 10 vol.), 7,7-dimethyl-7H-benzo[b]fluoreno[3,4-d]furan (150 g, 0.528 mol) was stirred and cooled to −78° C. in a reactor. n-BuLi (363 ml, 0.580 mol) was dropwise added and heated to room temperature before stirring overnight. Then, the temperature was again decreased to −78° C., followed by dropwise adding a solution of iodine (147.3 g, 0.580 mol) in THF (600 ml, 4 vol.). The temperature was elevated to room temperature and the reaction was terminated by adding $Na_2S_2O_3$ ag. The reaction mixture was subjected to extraction with $EA/H_2O$. The organic layer was pooled, concentrated, and slurried with methanol. The slurry was filtered and filtered to synthesize Intermediate 1-1 (188 g, yield 86%).

Synthesis of Intermediate 1-2

[Reaction Scheme 1-2]

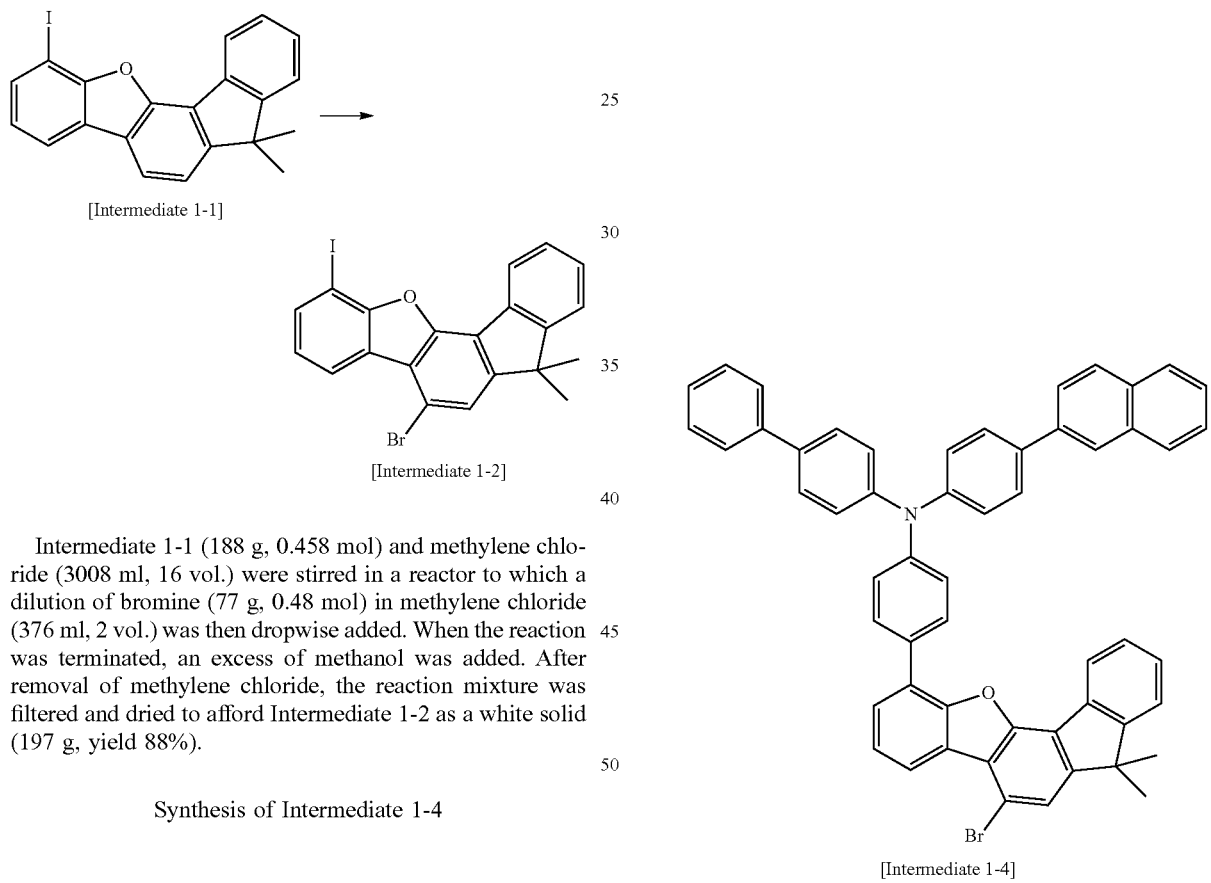

Intermediate 1-1 (188 g, 0.458 mol) and methylene chloride (3008 ml, 16 vol.) were stirred in a reactor to which a dilution of bromine (77 g, 0.48 mol) in methylene chloride (376 ml, 2 vol.) was then dropwise added. When the reaction was terminated, an excess of methanol was added. After removal of methylene chloride, the reaction mixture was filtered and dried to afford Intermediate 1-2 as a white solid (197 g, yield 88%).

Synthesis of Intermediate 1-4

[Reaction Scheme 1-3]

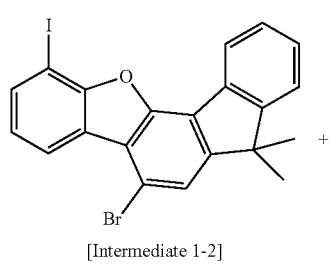

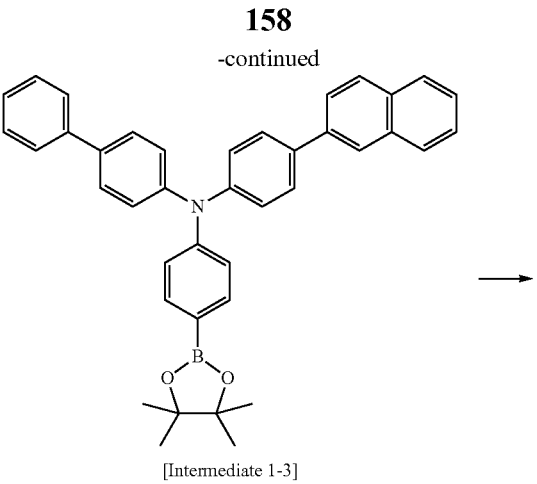

Intermediate 1-2 (45 g, 0.092 mol), Intermediate 1-3 (55.4 g, 0.097 mol), $Pd(pph_3)_4$ (3.2 g, 0.003 mol), and $K_2CO_3$ (31.8 g, 0.230 mol) were added into a reactor and stirred overnight together with toluene (315 ml), ethanol (180 ml), and $H_2O$ (135 ml) at 75° C. After extraction with ethyl acetate/$H_2O$, the organic layer was concentrated and subjected to column filtration (methylene chloride/heptane) to synthesize intermediate 1-4 (36.8 g, yield 49%).

Synthesis of Compound 4

[Reaction Scheme 1-4]

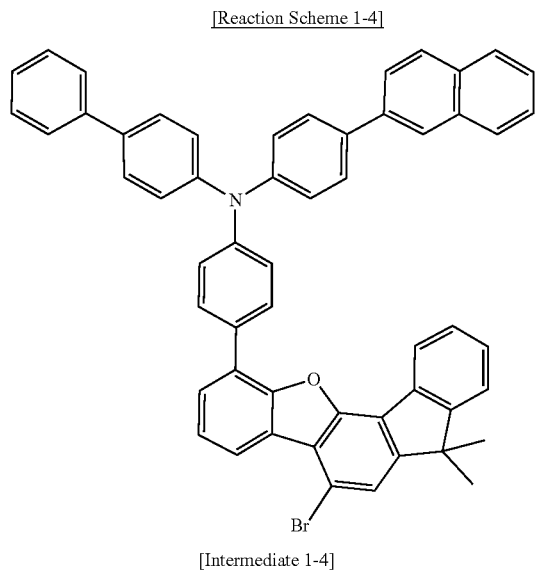

[Intermediate 1-4]

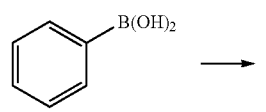

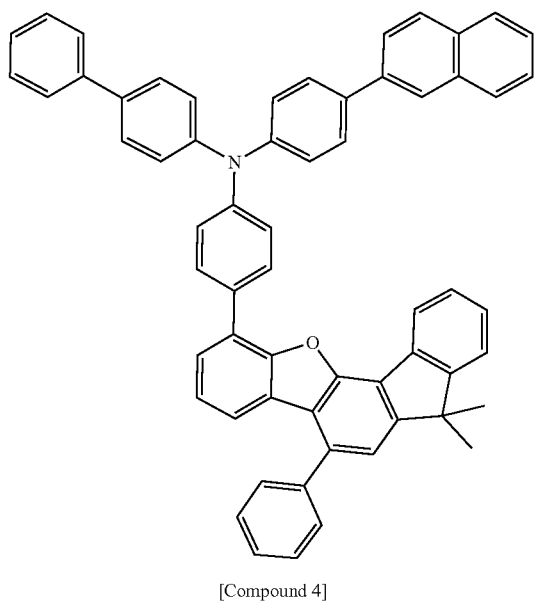

[Compound 4]

Intermediate 1-4 (13 g, 0.016 mol), phenyl boronic acid (2.16 g, 0.018 mol), Pd(pph$_3$)$_4$ (0.56 g, 0.0004 mol), and K$_2$CO$_3$ (5.55 g, 0.040 mol) added to a reactor and then stirred overnight together with toluene (91 ml), ethanol (39 ml), and H$_2$O (26 ml), at 75° C. After extraction with ethyl acetate/H$_2$O, the organic layer was concentrated and a solution of the concentrate in toluene was subjected to hot filtration. The filtrate was concentrated and recrystallized in methylene chloride and acetate to afford Compound 4 (6 g, yield 46%).

Preparation Example 2: Synthesis of Compound 6

Synthesis of Intermediate 2-2

[Reaction Scheme 2-1]

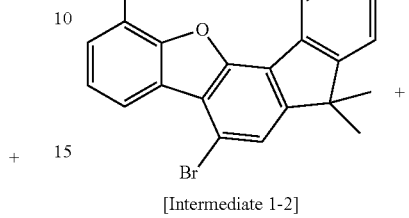

[Intermediate 1-2]

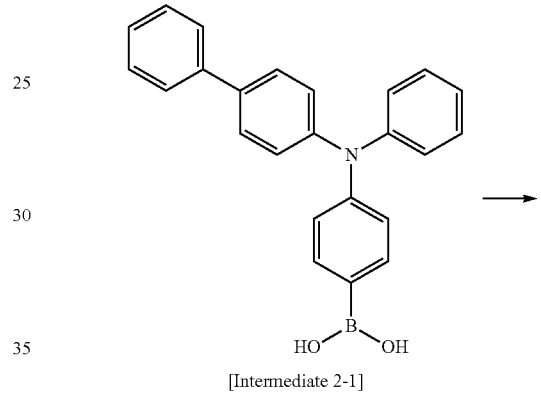

[Intermediate 2-1]

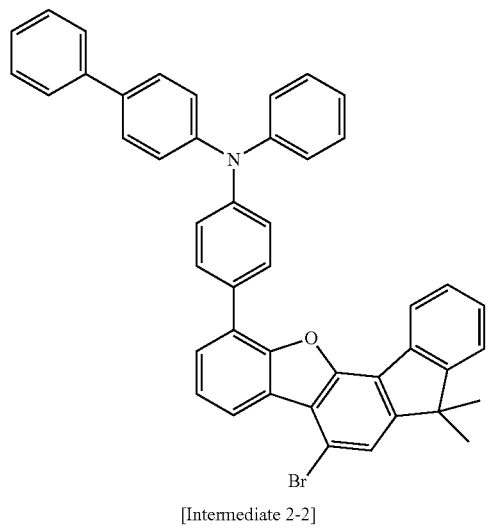

[Intermediate 2-2]

A synthesis procedure similar to that for Intermediate 1-4 was carried out using Intermediate 1-2 (50 g, 0.102 mol) synthesized in Preparation Example 1, and Intermediate 2-1 (39.2 g, 0.107 mol) to synthesize Intermediate 2-2 (36.5 g, yield 52%).

161

Synthesis of Compound 6

[Reaction Scheme 2-2]

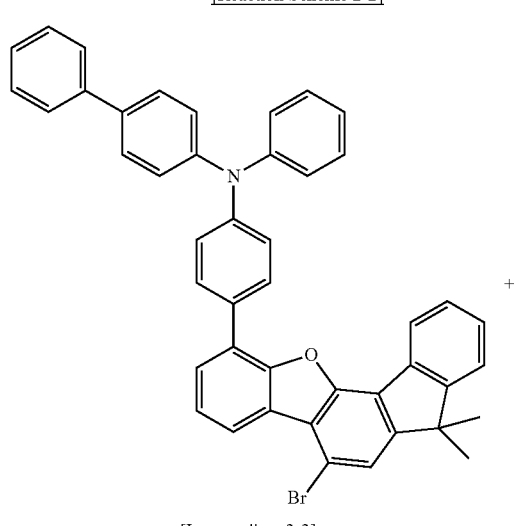

[Intermediate 2-2]

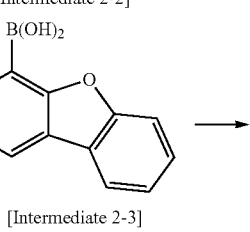

[Intermediate 2-3]

[Compound 6]

A synthesis procedure similar to that for Compound 4 was carried out using Intermediate 2-2 (36.5 g, 0.053 mol) and Intermediate 2-3 (12.4 g, 0.058 mol) to synthesize Compound 6 (20 g, yield 55%).

162

Preparation Example 3: Synthesis of Compound 7

Synthesis of Intermediate 3-1

[Reaction Scheme 3-1]

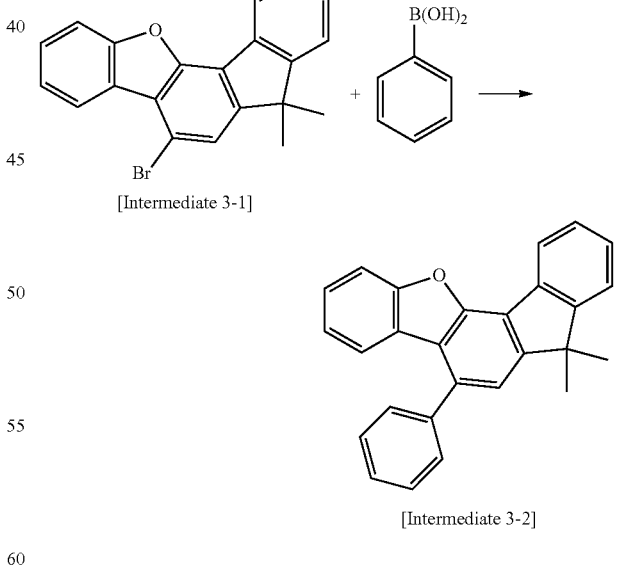

[Intermediate 3-1]

A synthesis procedure similar to that for Intermediate 1-2 was carried out using 7,7-dimethyl-7H-benzo[b]fluoreno[3,4-d]furan (130 g, 0.457 mol) and bromine (76.7 g, 0.480 mol) to synthesize Intermediate 3-1 (156 g, yield 94%).

Synthesis of Intermediate 3-2

[Reaction Scheme 3-2]

[Intermediate 3-1]

[Intermediate 3-2]

A synthesis procedure similar to that for Compound 4 is carried out using Compound 3-1 (156 g, 0.429 mol) and phenylboronic acid (47.6 g, 0.472 mol) to synthesize Intermediate 3-2 (144 g, yield 93%).

Synthesis of Intermediate 3-3

[Reaction Scheme 3-3]

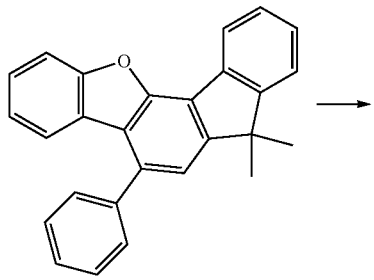

[Intermediate 3-2]

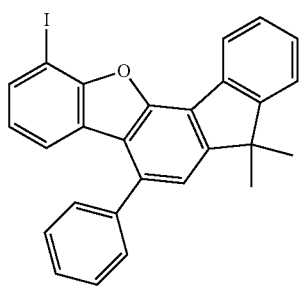

[Intermediate 3-3]

A synthesis procedure similar to that for Intermediate 1-1 was carried out using Compound 3-2 (14 g, 0.039 mol), n-BuLi (27 ml, 0.043 mol), and iodine (10.8 g, 0.043 mol) to synthesize Intermediate 3-3 (13 g, yield 68%).

Synthesis of Compound 7

[Reaction Scheme 3-4]

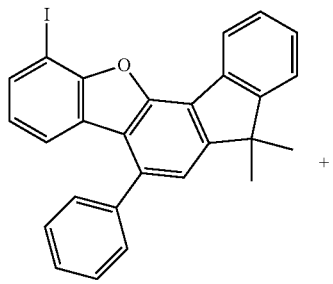

[Intermediate 3-3]

+

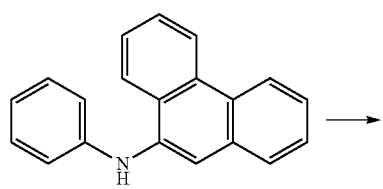

→

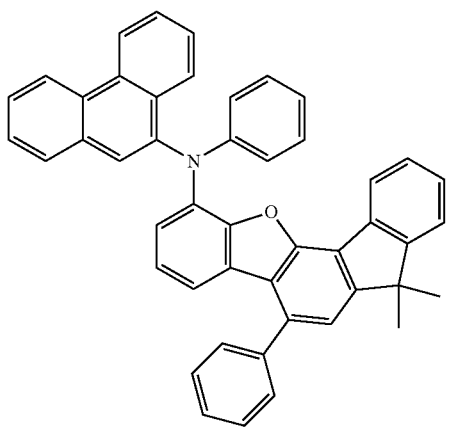

[Compound 7]

Intermediate 3-3 (10 g, 0.02 mol), N-phenyl-9-phenanthrene amine (6.1 g, 0.022 mol), Pd$_2$dba$_3$ (0.37 g, 0.0004 mol), tributyl phosphine (0.66 g, 0.0016 mol), sodium t-butoxide (3.9 g, 0.04 mol), and toluene (10 vol, 100 ml) were stirred under reflux for 3 hours in a reactor. Hot filtration in toluene, concentration, and column filtration afforded Compound 7 (6 g, yield 48%).

Preparation Example 4: Synthesis of Compound 2

Synthesis of Intermediate 4-1

[Reaction Scheme 4-1]

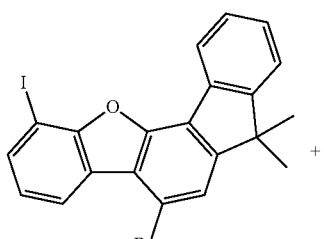

[Intermediate 1-2]

+

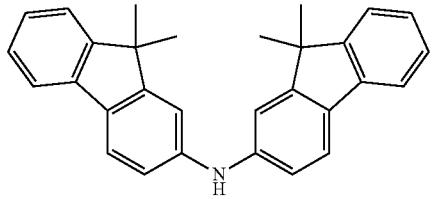

→

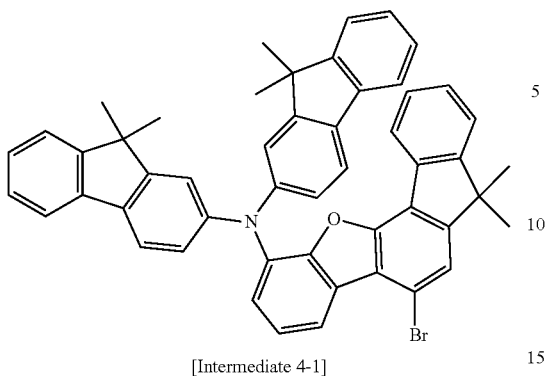

[Intermediate 4-1]

Intermediate 1-2 (15 g, 0.03 mol) synthesized in Preparation Example 1, N-(9,9-dimethyl-9H-fluoren-2-yl)-9,9-dimethyl-9H-fluorene-2-amine (12.3 g, 0.031 mol), Pd(OAc)2 (0.3 g, 0.002 mol), xanthene (0.9 g, 0.002 mol), STB (4.4 g, 0.046 mol), and toluene (150 ml) were stirred overnight together under reflux in a reactor. After completion of the reaction, hot filtration with toluene and column filtration afforded Intermediate 4-1 (12.5 g, yield 53%).

Synthesis of Compound 2

[Reaction Scheme 4-2]

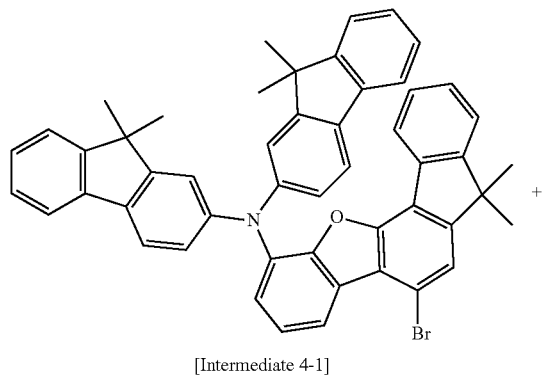

[Intermediate 4-1]

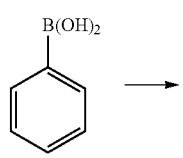

[Compound 2]

Intermediate 4-1 (7.5 g, 0.01 mol), phenylboronic acid (1.3 g, 0.011 mol), Pd(pph3)4 (0.3 g, 0.0003 mol), potassium carbonate (3.4 g, 0.025 mol), toluene (52 ml), ethanol (30 ml), and distilled water (22 ml) were stirred overnight together under reflux. After extraction with ethyl acetate/distilled water, the organic layer was concentrated and filtered through a column to afford Compound 2 (3 g, yield 40%).

Preparation Example 5: Synthesis of Compound 13

Synthesis of Compound 13

[Reaction Scheme 5-1]

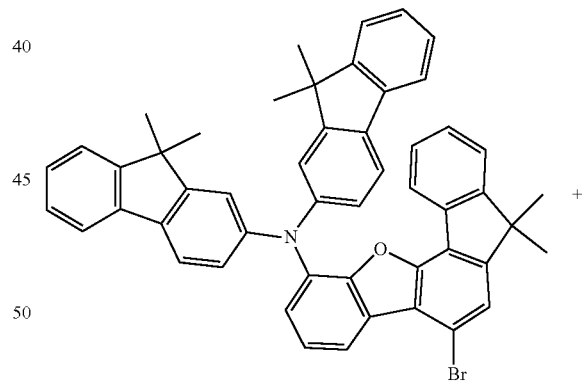

[Intermediate 4-1]

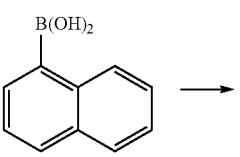

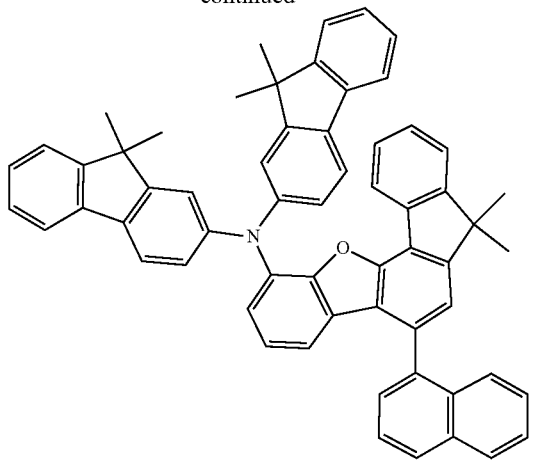

[Compound 13]

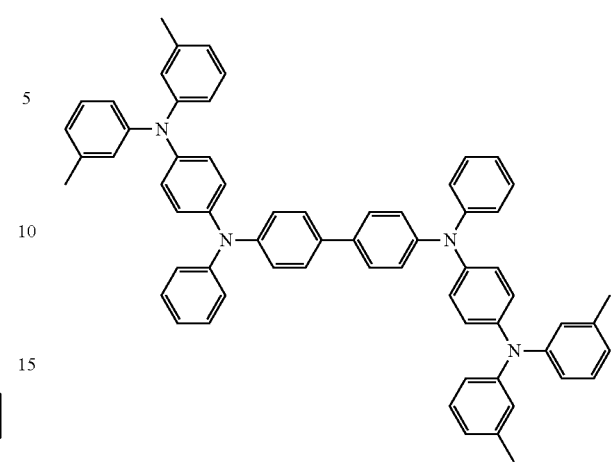

[DNTPD]

[Chemical Formula G]

Intermediate 4-1 (7.5 g, 0.01 mol), 1-naphthyl boronic acid (1.9 g, 0.011 mol), Pd(pph3)4 (0.3 g, 0.0003 mol), potassium carbonate (3.4 g, 0.025 mol), toluene (52 ml), ethanol (30 ml), and distilled water (22 ml) were stirred under reflux, together. After extraction with ethyl acetate/distilled water, the organic layer was concentrated and the concentrate was filtered through a column to afford Compound 13 (4 g, yield 50%).

Examples 1 to 11: Fabrication of Organic Light-Emitting Diode

An ITO glass substrate was patterned to have a translucent area of 2 mm×2 mm and cleansed. The ITO glass was mounted in a vacuum chamber that was then set to have a base pressure of $1\times10^{-7}$ torr. On the ITO glass substrate, films were sequentially formed of DNTPD (450 Å), [Chemical Formula G] (200 Å), and each of the compounds listed in Tables 1 and 2 for the second hole transport layer (50 Å). A light-emitting layer (200 Å) was formed of a mixture of [Chemical Formula BH] and [Chemical Formula BD] at a weight ratio of 97:3. Then, [Chemical Formula E-2] for an electron transport layer (300 Å), [Chemical Formula E-1] for an electron injection layer (10 Å), and an Al layer (1000 Å) were sequentially deposited to fabricate an organic light-emitting diode. The organic light-emitting diodes thus obtained were measured at 0.4 mA for luminescence properties:

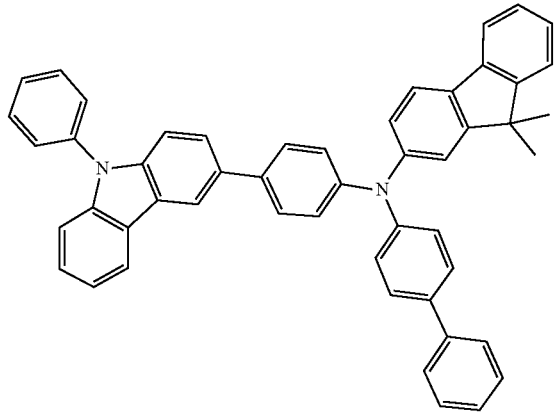

[Chemical Formula E-1]

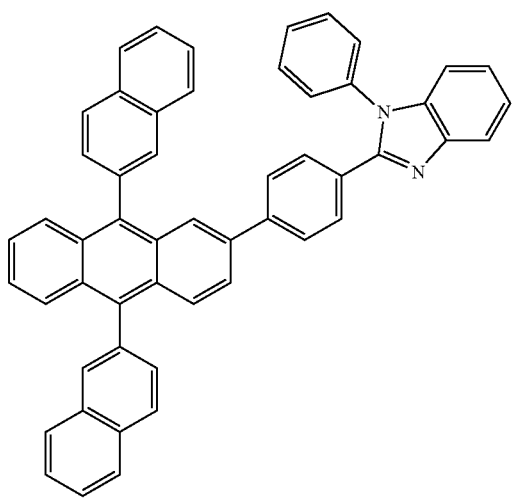

[Chemical Formula E-2]

[Chemical Formula BH]

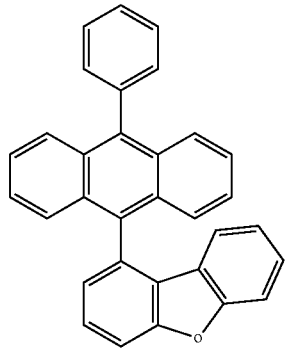

[Chemical Formula BD]

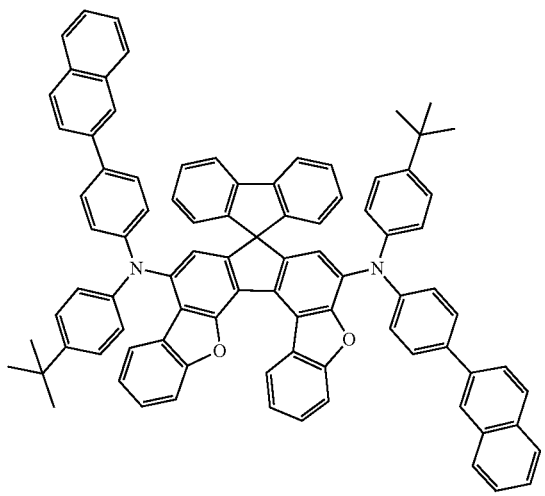

Comparative Examples 1 and 2

An organic light-emitting diode was fabricated in the same manner as in Example 1, with the exception that the compound of the Chemical Formula B or C was used, instead of the compounds used for the second hole transport layer in Examples 1 to 11. The luminescence of the organic light-emitting diode was measured at 0.4 mA.

[Chemical Formula B]

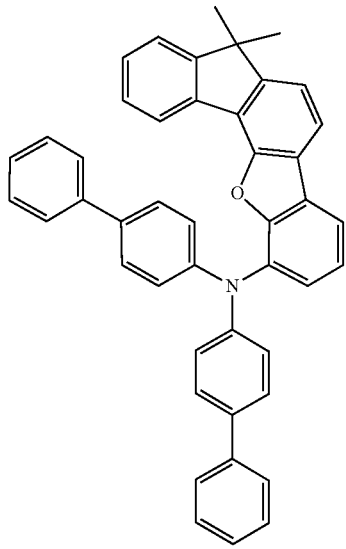

[Chemical Formula C]

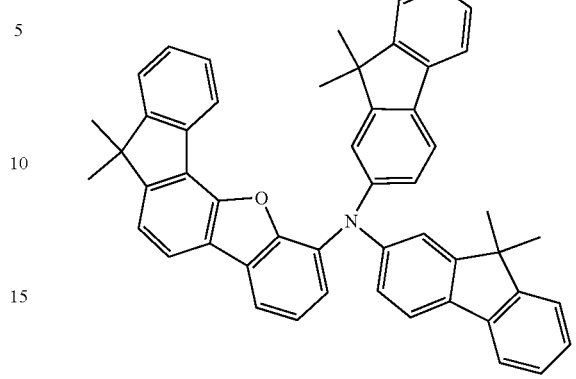

The organic light-emitting diodes fabricated in Examples 1 to 9 were measured for driving voltage, emission efficiency, and lifetime, and the measurements are summarized in Table 1, below.

TABLE 1

| Ex. # | Compound # | Driving Volt. (V) | Efficiency (Cd/A) | Lifetime (T97) |
|---|---|---|---|---|
| 1 | 1 | 3.40 | 7.8 | 98 |
| 2 | 3 | 3.49 | 7.7 | 42 |
| 3 | 4 | 3.42 | 7.6 | 48 |
| 4 | 5 | 3.44 | 7.6 | 85 |
| 5 | 6 | 3.43 | 7.3 | 109 |
| 6 | 7 | 3.46 | 7.4 | 31 |
| 7 | 26 | 3.49 | 7.4 | 32 |
| 8 | 31 | 3.47 | 7.4 | 34 |
| 9 | 24 | 3.45 | 7.3 | 125 |
| C. 1 | Chemical Formula B | 3.46 | 6.9 | 20 |

As is understood from the data of Table 1, the organic light-emitting diodes according to the present disclosure were superior to that using the compound of Comparative Example 1 in terms of efficiency and lifetime, with more superiority upon using Compounds 1, 6, and 24.

In addition, the organic light-emitting diodes fabricated according to Examples 10 and 11 and Comparative Example 2 were measured for driving voltage, emission efficiency, and external quantum efficiency (EQE), and the measurements are summarized in Table 2, below.

TABLE 2

| Ex. # | Compound # | Driving Volt. (V) | Efficiency (Cd/A) | EQE |
|---|---|---|---|---|
| 10 | 2 | 3.43 | 7.1 | 9.5 |
| 11 | 13 | 3.42 | 7.1 | 9.5 |
| C. 2 | Chemical Formula C | 3.43 | 6.6 | 8.9 |

As is understood from the data of Table 2, the organic light-emitting diode according to the present disclosure was better in efficiency than that using the compound of Comparative Example 2.

As described hitherto, when applied to a hole transport layer or a hole injection layer in an organic light-emitting diode, the compound according to the present disclosure can confer excellent diode properties including high emission efficiency and a long lifetime on the organic light emitting diode (OLED).

Particularly, an OLED including a first hole transport layer and a second transport layer interposed between the first hole transport layer and a light-emitting layer wherein the compound of the present disclosure is used in the second transport layer can exhibit high emission efficiency and a long lifetime.

What is claimed is:

1. A compound for an organic light-emitting diode, represented by the following Chemical Formula A or B:

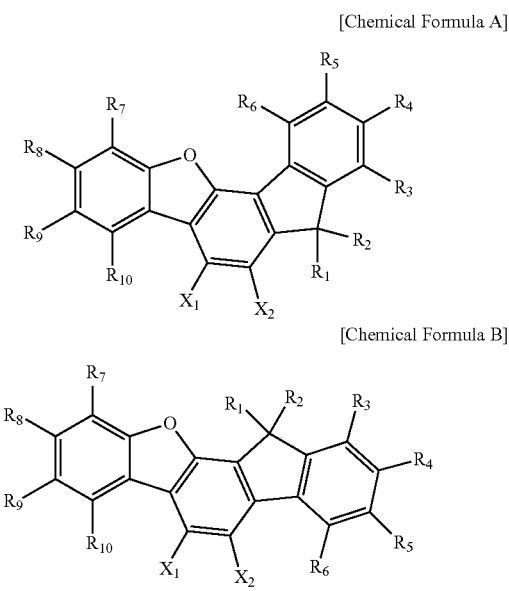

[Chemical Formula A]

[Chemical Formula B]

wherein, $X_1$ and $X_2$, which are same or different, are each independently any one selected from a hydrogen atom, a deuterium atom, a substituted or unsubstituted alkyl of 1 to 30 carbon atoms, a substituted or unsubstituted cycloalkyl of 3 to 30 carbon atoms, a substituted or unsubstituted aryl of 6 to 50 carbon atoms, a substituted or unsubstituted alkylsilyl of 1 to 30 carbon atoms, a substituted or unsubstituted arylsilyl of 6 to 30 carbon atoms, a cyano, and a halogen, wherein at least one of $X_1$ and $X_2$ is any one selected from among a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted alkylsilyl of 1 to 30 carbon atoms, and a substituted or unsubstituted arylsilyl of 6 to 30 carbon atoms; and $R_1$ to $R_{10}$, which are same or different, are each independently any one selected from among a hydrogen atom, a deuterium atom, a substituted or unsubstituted alkyl of 1 to 30 carbon atoms, a substituted or unsubstituted cycloalkyl of 3 to 30 carbon atoms, a substituted or unsubstituted aryl of 6 to 50 carbon atoms, a substituted or unsubstituted alkylsilyl of 1 to 30 carbon atoms, a substituted or unsubstituted arylsilyl of 6 to 30 carbon atoms, a cyano, and a halogen, wherein $R_7$ is a substituent represented by the following Structural Formula A:

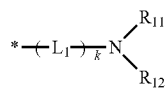

[Structural Formula A]

wherein, the linker $L_1$ is any one selected from among a single bond, and a substituted or unsubstituted arylene of 6 to 30 carbon atoms, k is an integer of 1 to 3, under which when k is 2 or greater, the corresponding $L_1$'s are same or different, $R_{11}$ and $R_{12}$, which are same or different, are each independently any one selected from among a substituted or unsubstituted aryl of 6 to 18 carbon atoms and a substituted or unsubstituted heteroaryl of 2 to 20 carbon atoms, "*" denotes a bonding site between any one of $R_3$ to $R_{10}$ and a carbon atom of the benzene rings in the scaffold;

$R_1$ and $R_2$ may be connected to each other to form a mono- or polycyclic aliphatic or aromatic ring;

wherein the term "substituted" in the expression "substituted or unsubstituted" used for [Chemical Formula A] and [Chemical Formula B] means having at least one substituent selected from the group consisting of a deuterium atom, a cyano, a halogen, a nitro, an alkyl of 1 to 24 carbon atoms, a halogenated alkyl of 1 to 24 carbon atoms, an aryl of 6 to 24 carbon atoms, an arylalkyl of 6 to 24 carbon atoms, a heteroaryl of 2 to 24 carbon atoms, an alkylsilyl of 1 to 24 carbon atoms, and an arylsilyl of 6 to 24 carbon atoms.

2. The compound of claim 1, wherein the substituents $R_1$ and $R_2$, which are same or different, are each independently any one selected from an alkyl of 1 to 6 carbon atoms and an aryl of 6 to 18 carbon atoms.

3. The compound of claim 2, wherein the substituents $R_1$ and $R_2$, which are same or different, are each independently any one selected from methyl and phenyl.

4. The compound of claim 1, wherein one of the substituents $X_1$ and $X_2$ is any one selected from among a substituted or unsubstituted alkyl of 1 to 30 carbon atoms, a substituted or unsubstituted aryl of 6 to 50 carbon atoms, and a substituted or unsubstituted cycloalkyl of 3 to 30 carbon atoms, and the other substituent is a hydrogen atom or a deuterium atom.

5. The compound of claim 1, wherein at least one of the substituents $X_1$ and $X_2$ is any one selected from among a substituted or unsubstituted alkyl of 1 to 12 carbon atoms, a substituted or unsubstituted cycloalkyl of 3 to 18 carbon atoms, or a substituted or unsubstituted aryl of 6 to 18 carbon atoms.

6. The compound of claim 5, wherein one of the substituents $X_1$ and $X_2$ is a substituted or unsubstituted aryl of 6 to 18 carbon atoms, and the other substituent is a hydrogen atom or a deuterium atom.

7. The compound of claim 1, wherein the compound represented by Chemical Formula A or B is any one selected from the group consisting of the compounds represented by [Compound 1] to [Compound 5], [Compound 7] to [Compound 11], [Compound 13] to [Compound 15], [Compound 18], [Compound 20] to [Compound 23], [Compound 27], [Compound 28], [Compound 30] to [Compound 33], [Compound 36], [Compound 40], [Compound 46], and [Compound 53]:

[Compound 1]
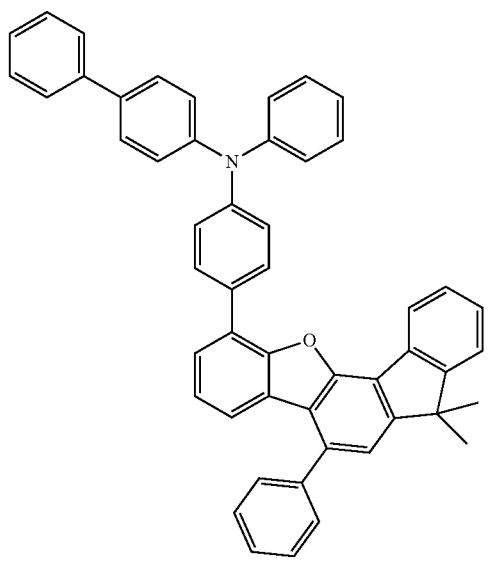
[Compound 2]
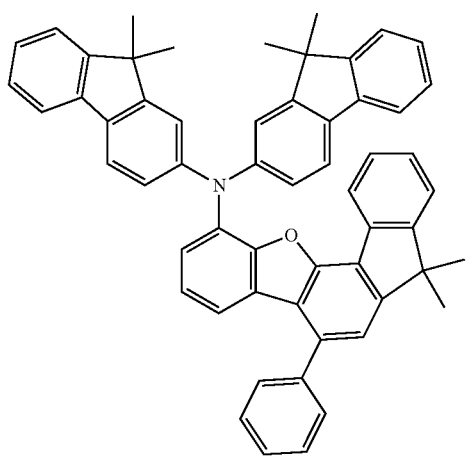
[Compound 3]
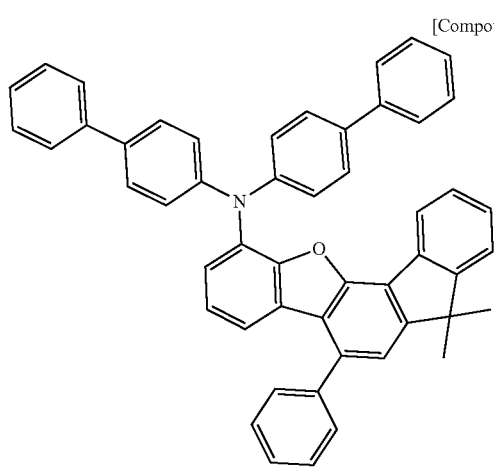
[Compound 4]
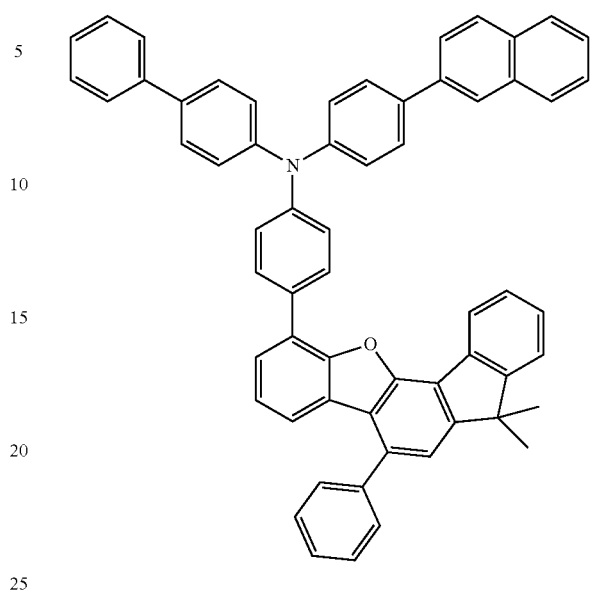
[Compound 5]
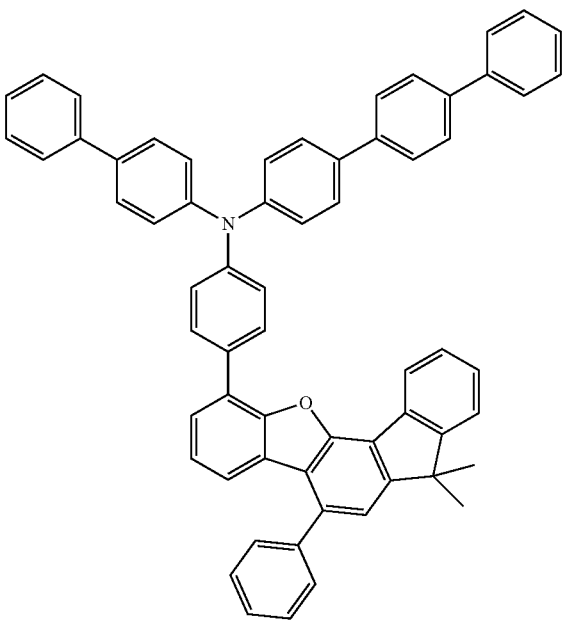

[Compound 7]
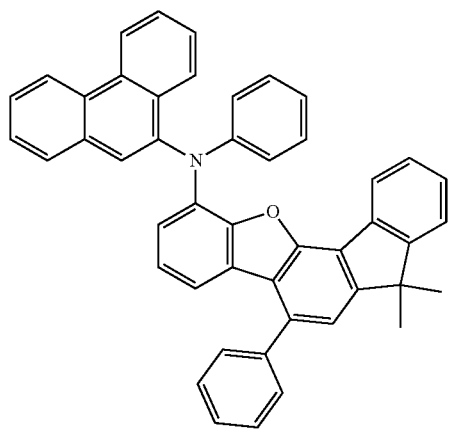
[Compound 8]
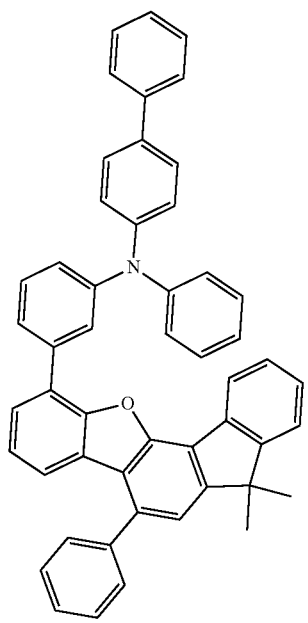
[Compound 9]
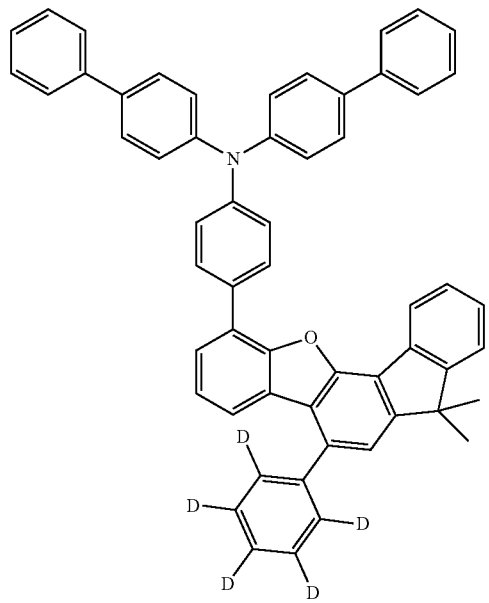
[Compound 10]
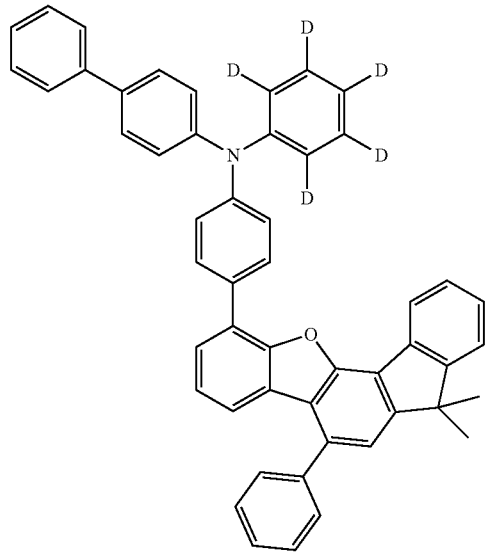

177
-continued
[Compound 11]
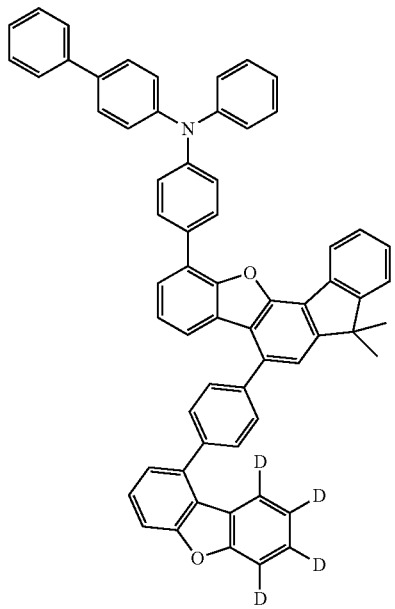
[Compound 13]
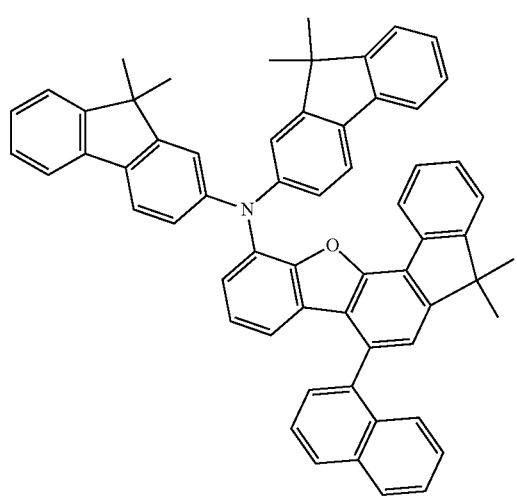
178
-continued
[Compound 14]
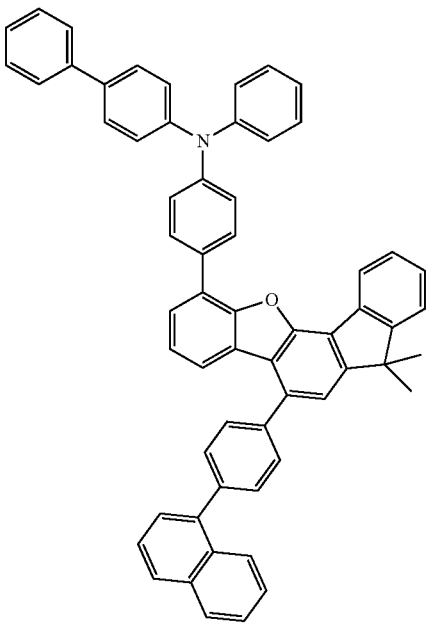
[Compound 15]
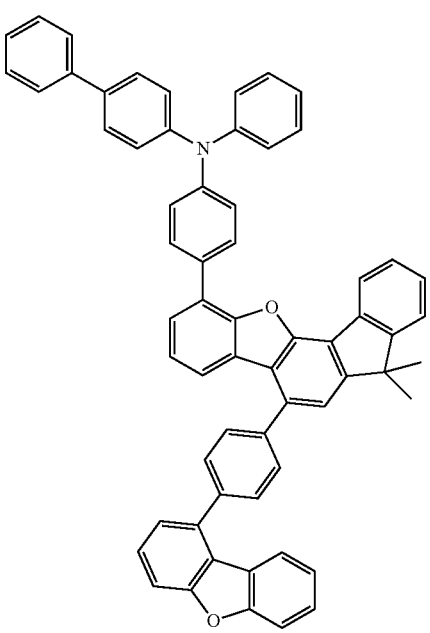

[Compound 18]
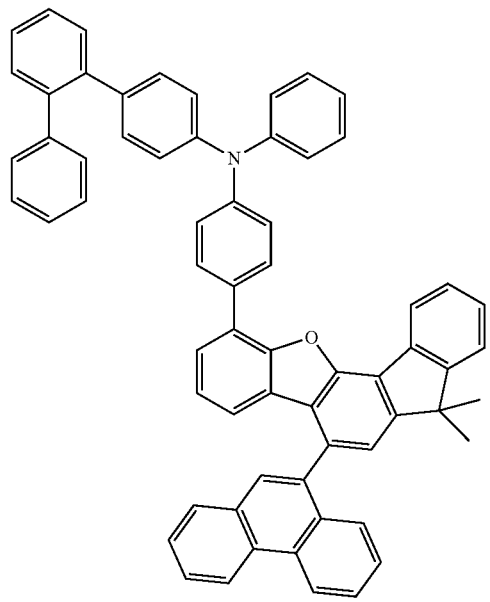
[Compound 20]
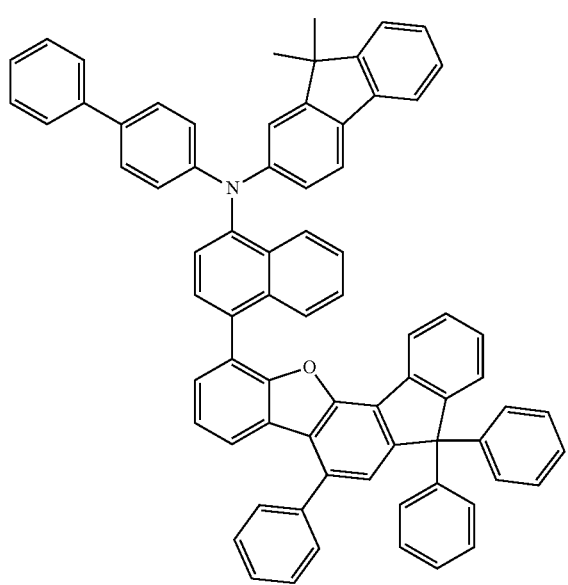
[Compound 21]
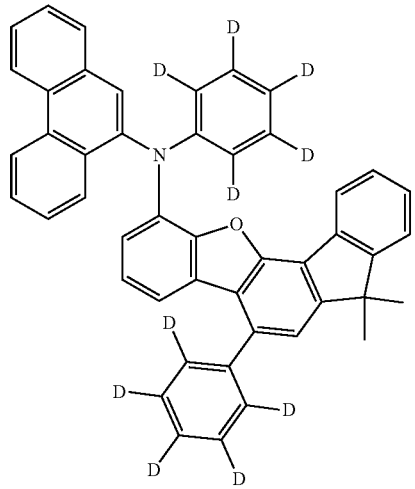
[Compound 22]
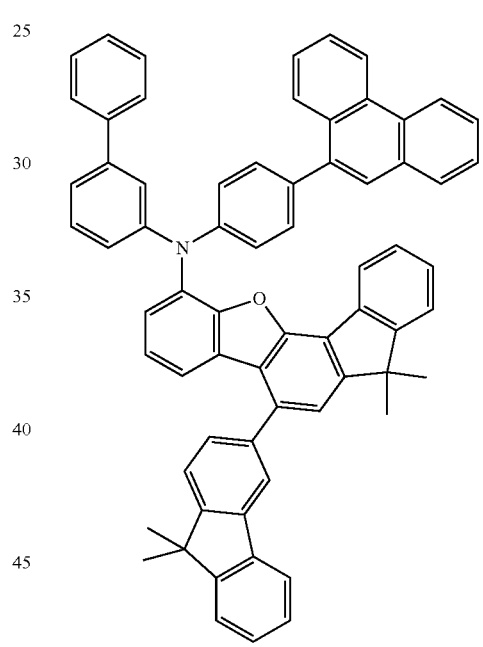
[Compound 23]
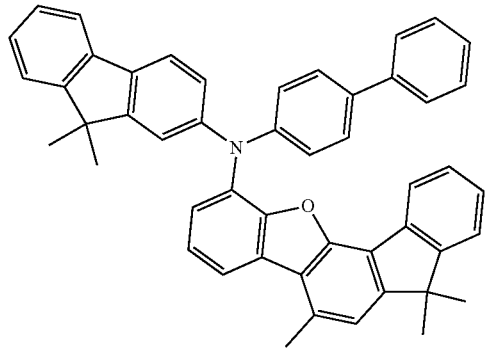

[Compound 27]
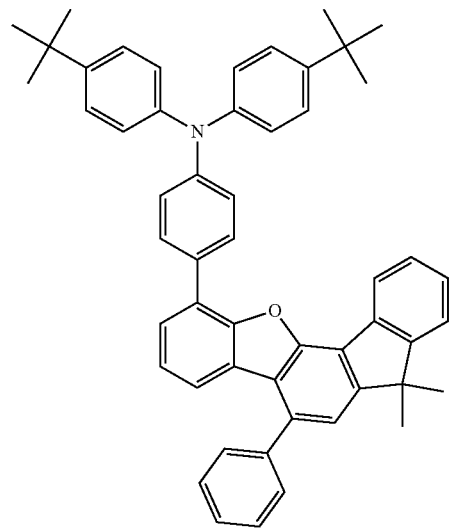
[Compound 30]
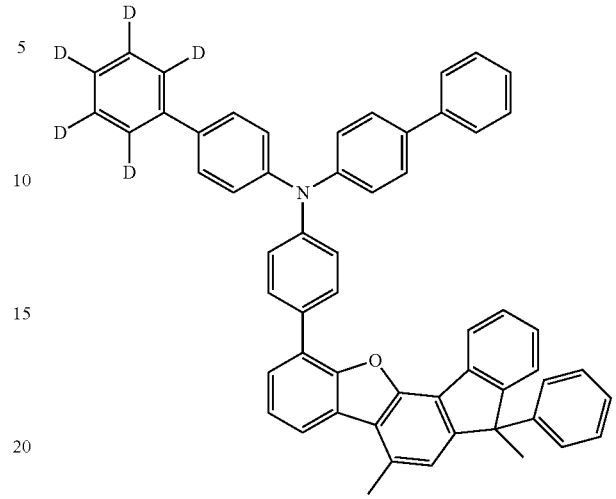
[Compound 31]
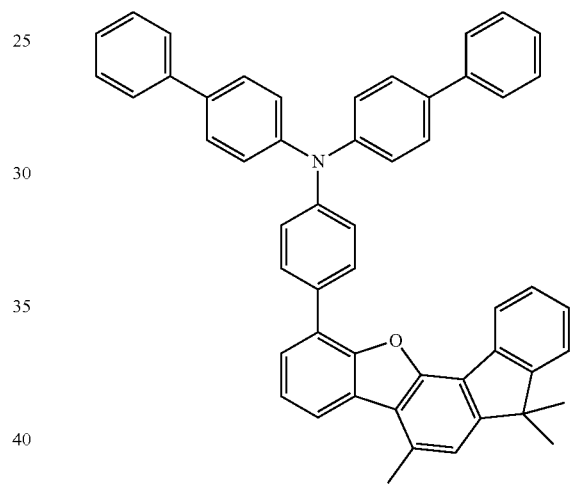
[Compound 28]
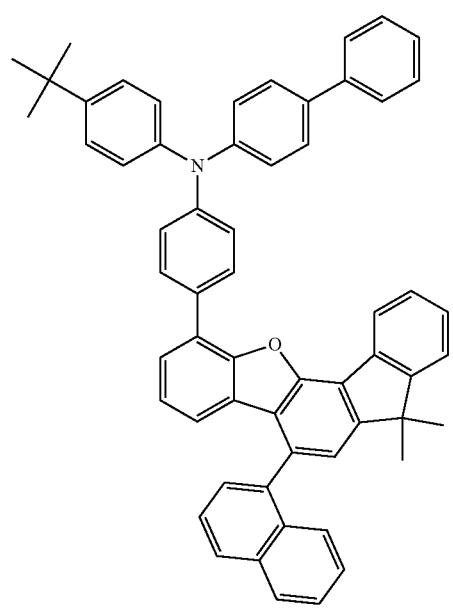
[Compound 32]
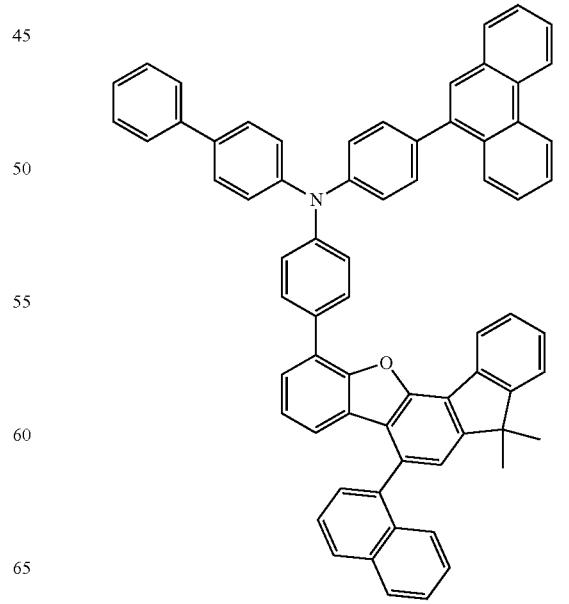

[Compound 33]
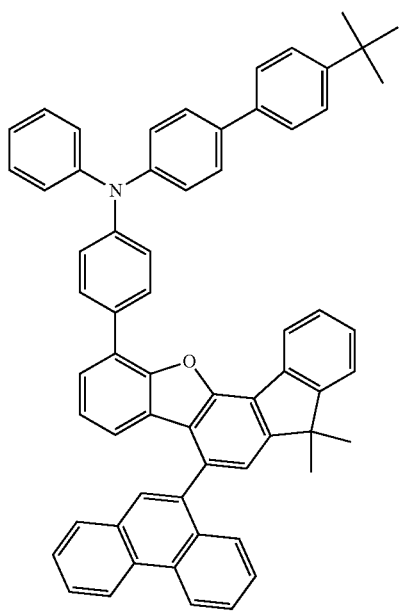
[Compound 40]
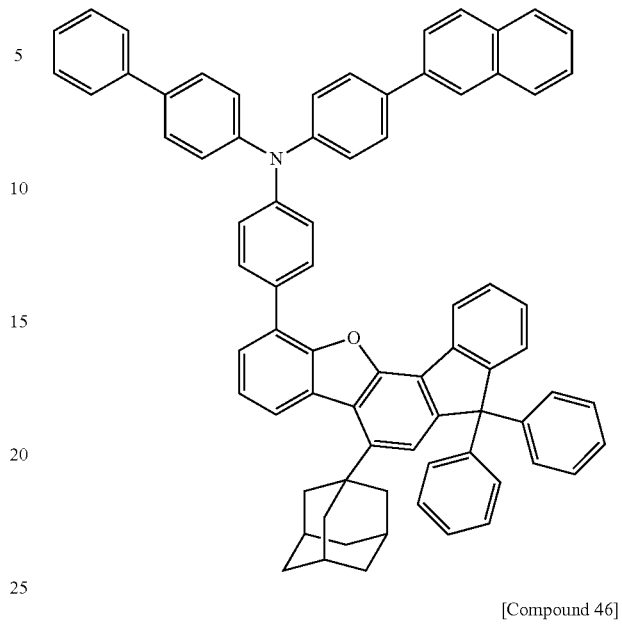
[Compound 46]
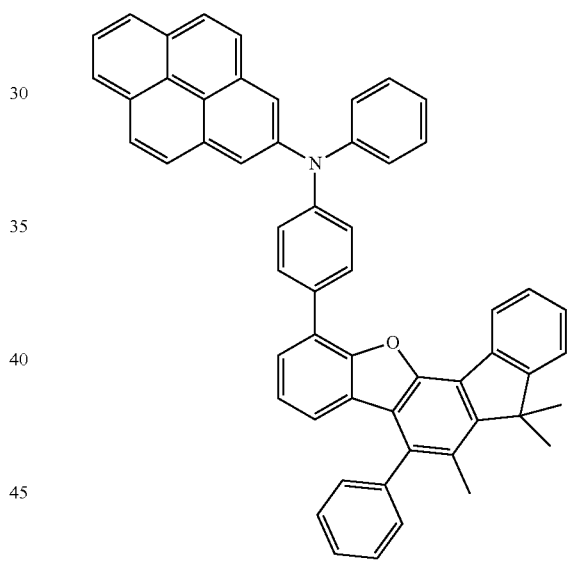
[Compound 36]
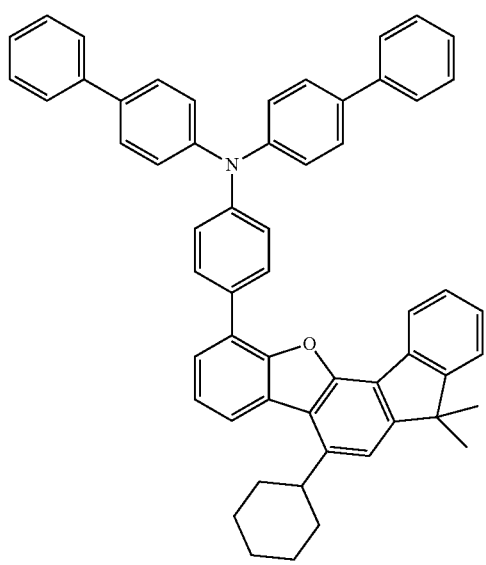
[Compound 53]
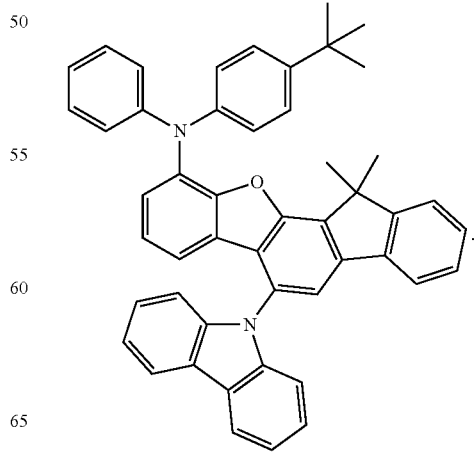

8. An organic light-emitting diode, comprising:
a first electrode;
a second electrode facing the first electrode;
an organic layer interposed between the first electrode and the second electrode, wherein the organic layer includes the compound of claim 1.

9. The organic light-emitting diode of claim 8, wherein the organic layer interposed between the first electrode and the second electrode includes a hole transport layer or a hole injection layer, and the compound is used in the hole transport layer or the hole injection layer.

10. The organic light-emitting diode of claim 9, wherein the hole transport layer includes a first hole transport layer and a second hole transport layer disposed between the first hole transport layer and the light-emitting layer, and the compound is used in the second hole transport layer.

11. The organic light-emitting diode of claim 9, wherein the organic layer further comprises at least one selected from among a light-emitting layer, a functional layer capable of both hole injection and hole transport, an electron transport layer, and an electron injection layer.

12. The organic light-emitting diode of claim 11, wherein the at least one selected from among the layers is formed using a deposition process or a solution process.

13. The organic light-emitting diode of claim 8, wherein the organic light-emitting diode is used for a device selected from among a flat display device, a flexible display device, a monochrome or grayscale flat illumination device, and a monochrome or grayscale flexible illumination device.

* * * * *